US007312050B2

(12) United States Patent
Hageman et al.

(10) Patent No.: US 7,312,050 B2
(45) Date of Patent: Dec. 25, 2007

(54) NUCLEIC ACIDS ENCODING INTERPHOTORECEPTOR MATRIX PROTEINS

(75) Inventors: Gregory S. Hageman, Coralville, IA (US); Markus H. Kuehn, Amana, IA (US)

(73) Assignee: University of Iowa Research Foundation, Iowa City, IA (US)

(*) Notice: Subject to any disclaimer, the term of this patent is extended or adjusted under 35 U.S.C. 154(b) by 42 days.

(21) Appl. No.: 10/007,270

(22) Filed: Nov. 8, 2001

(65) Prior Publication Data

US 2002/0160954 A1    Oct. 31, 2002

Related U.S. Application Data

(63) Continuation-in-part of application No. 09/430,195, filed on Oct. 29, 1999, now abandoned, which is a continuation-in-part of application No. 09/183,972, filed on Oct. 29, 1998, now abandoned.

(51) Int. Cl.
*C12P 21/06* (2006.01)
*C07H 21/02* (2006.01)

(52) U.S. Cl. ..................... 435/69.1; 536/23.1
(58) Field of Classification Search ............... 435/69.1, 435/320.1; 536/23.1, 24.1, 24.3, 24.31
See application file for complete search history.

(56) References Cited

U.S. PATENT DOCUMENTS 5,466,591 A * 11/1995 Abramson et al. .......... 435/194

OTHER PUBLICATIONS

Kuehn et al. Expression and characterization of the IPM 150 gene (IMPG1) product, novel human photoreceptor cell-associated chondroitin-sulfate proteoglycan. (1999), Matrix Biology 18(5) p. 509-518.*
Bonaldo et al. Normalization and subtraction: two approaches to facilitate gene discovery (1996). Genome Res. 6(9), 791-806.*
Kuehn et al. Molecular characterization of the murine orthologue of the human retinal proteoglycan IPM 150 (2000), Molecular Vision, 6: pp. 148-56.*
Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Acharya, S. et al. SPACR, "A novel interphotoreceptor matrix glycoprotein in human retina that interacts with hyaluronan," J Biol Chem 273, 31599-31606 (1998).
Acharya, S., Rayborn, M. & Hollyfield, J. "Characterization of SPACR, a sialoprotein associated with cones and rods present in the interphotoreceptor matrix of the human retina: immunological and lectin binding analysis." Glycobiology 8, 997-1006 (1998).
Alberdi, E., C.C. & Becerra, S.P. "Pigment epithelium-derived factor (PEDF) binds to glycosaminoglycans: analysis of the binding site." Biochemistry 37, 10643-10652 (1998).

Alignments HSIMIPG3, HSIMPG17 Felbor w/ SEQ ID Nos. 1.3.5.
Anderson et al., "Vitronectin Receptor Expression and Distribution at the Photoreceptor-Retinal Pigment Epithelial Interface", J. Comp. Neurol. 360:1-16 (1995).
Blanks, J.C., Johnson, L.V. & Hageman, G.S. "Stage-specific binding of peanut agglutinin to aggregates of degenerating photoreceptor cells in the rd mouse retina." Exp. Eye Res., 265-273 (1993).
Chaitin, M.H., Wortham, H.S. & Brun-Zinkernagel, A.M. "Immunocytochemical localization of CD44 in the mouse retina." Exp. Eye Res. 58, 359-365 (1994).
Chu, Y. et al. "Development study of chondroitin-6-sulphate in normal and dystrophic rat retina." Graefes Archive Clin. & Exp. Ophthalmol. 230, 476-482 (1992).
Felbor et al. "Mapping, genomic organization and mutational analyses of a novel interphotoreceptor matrix gene (IPM150): a candidate for 6q-linked maculopathies." Am. J. Human Genetics Suppl. A333:1947 (1997).
Felbor et al. "Genomic organization and chromostomal localization of the interphotoreceptor matrix proteogycan-1 (IMPG1) gene: a candidate for 6q-linked retinopathies" *Cytogenet. Cell Genet.*, 1998, pp. 12-17, vol 81.
Gehrig, A. et al. "Assessment of the interphotoreceptor matrix proteoglycan-1 (IMPG1) gene localized to 6q13-q15 in autosomal dominant Stardgardt-like disease (ADSTGD), progressive bifocal chorioretinal atrophy (PBCRA) and North Carolina macular dystophy (MCDR1)" *J. Med. Genetics*, Aug. 1998, pp. 641-654, vol. 35, No. 8.
Genbank Accession No. AA721009 (1998).
Genbank Accession No. AA815118 (1998).
Genbank Accession No. AF01772 (1998).
Genbank Accession No. AF047491, Feb. 24, 1998 (Kuehn, M.H).
Genbank Accession No. AF047492, Feb. 24, 1998 (Kuehn, M.H.).
Genbank Accession No. H38604 (1995).
Genbank Accession No. U76717(1996).
Hageman and Johnson, "Structure, Composition and Funtion of the Retinal Interphotoreceptor Matrix", Progress in Retinal Research, vol. 10, pp. 207-249, Osborne and Chader, eds., Pergamon Press (1991).
Hageman et al., "The Interphotoreceptor Matrix Mediates Primate Retinal Adhesion", Archi. of Ophthalmology 113:655-660 (1995).
Hageman, G.S. & Johnson, L.V. "Chondroitin 6-sulfate glycosaminoglycan is a major constituent of primate cone photoreceptor matrix sheaths." Curr. Eye Res. 6, 639-646 (1987).
Hageman, G.S. & Kuehn, M.H. "Biology of the Interphotoreceptor Matrix-RPE-Retina Interface." The Pigmented Retinal Epithelium: Current Aspects of Funtion and Disease (eds. Marmor, M. & Wolfensberger, T.) 417-454 (Oxford University Press, New York, 1998).

(Continued)

*Primary Examiner*—Christine J. Saoud
*Assistant Examiner*—Jegatheesan Seharaseyon
(74) *Attorney, Agent, or Firm*—Townsend and Townsend and Crew LLP

(57) ABSTRACT

Methods and compositions for treating ocular disorders such as retinal detachment and macular degeneration and methods and compositions for prognosing or diagnosing retinal detachment or macular degeneration in a subject are disclosed.

4 Claims, 4 Drawing Sheets

OTHER PUBLICATIONS

Hageman, G.S., Kirchoff-Rempe, M.A., Lewis, G.P., Fisher, S.K. & Anderson, D.H. "Sequestration of basic fibroblast growth factor in the primate retinal interphotoreceptor matrix." Proc. Natl. Acad. Sci. U.S.A 88, 6706-6710 (1991).

Hageman, G.S., Marmor, M.F., Yao, X.Y. & Johnson, L.V. "The interphotoreceptor matrix mediates primate retinal adhesion." Arch. Ophthalmol. 113, 655-660 (1995).

Hewitt and Adler, "The retinal pigment epithelium and interphotoreceptor matrix: structure and specialized functions", Retina, Ryan et al., eds., pp. 57-64, The C. V. Mosby Company (1989).

Hollyfield et al., "Retinal Attachment to the Pigment Epithelium", Retina 9:1:59-68 (1989).

Hollyfield, J.G., Rayborn, M.E., Landers, R.A. & Myers, K.M. "Insoluble interphotoreceptor matrix domains surround rod photoreceptors in the human retina." Exp. Eye Res. 51, 107-110 (1990).

Hollyfield, J.G., Rayborn, M.E., Tammi, M. & Tammi, R. "Hyaluronan in the Interphotoreceptor Matrix of the Eye: Species Differences in Content, Distribution, Ligand Binding and degradation." Exp Eye Res 66, 241-248 (1998).

Iwasaki, M., Rayborn, M.E., Tawara, A. & Hollyfield, J.G. "Proteoglycans in the mouse interphotoreceptor matrix. V. Distribution at the apical surface of the pigment epithelium before and after retinal separation." Exp. Eye Res. 54, 415-432 (1992).

Johnson and Hageman, "Structural and Compositional Analyses of Isolated Cone Matrix Sheaths", Invest. Ophthalmol. Vis. Sci. 32:7:1951-1957 (1991).

Johnson et al., "Effects of Retinal Degenerations on the Cone Matrix Sheath", Inherited and Environmentally Induced Retinal Degenerations, pp. 217-232, Alan R. Liss, Inc. (1989).

Kelsell et al., "Localization of a Gene (CORD7) for a Dominant Cone-Rod Dystrophy to Chromosome 6q", Am. J. Hum. Genet. 63:274-279 (1998).

Korte et al., "Hyaluronate Distribution in the Regenerating Retinal Pigment Epithelium of the Rabbit: A Study Using Confocal Laser Scanning Microscopy", Microscopy Res. Tech. 29:344-349 (1994).

Kuehn, M.H. et al., "H. sapiens interphotoreceptor matric porteoglycan 150 (IMPG1)", Database Genbank [Online] Accession No. AF047492 (Feb. 24, 1998).

Kuehn, M.H. et al., "M. fascicularis interphotoreceptor matrix porteoglycan 150", Database Genbank [Online] Accession No. AF047491 (Feb. 24, 1998).

Kuehn, M., Stone, E. & Hageman, G. "Molecular analysis of IPM 150, a photoreceptor cell-specific proteoglycan," Invest. Opthalmol. Vis. Sci. Suppl. 38, S599 (1997).

Kuehn, M.H. & Hageman G.S. "Characterization of a cDNA encoding IPM150, a novel human interphotoreceptor matrix chondroitin 6-sulfate proteoglycan" *Invest. Ophthalmol. & Vis. Sci.*, Mar. 15, 1995, p. S510, vol. 36, No. 4.

Kuehn, M.H., Mullins, R.F. & Hageman, G.S. "Retinal Interphotoreceptor matrix proteoglycan core protein sequences are unique and highly conserved." Invest. Ophthamol. Vis. Sci. Suppl. 34, 1201 (1993).

Lazarus and Hageman, "Xyloside-Induced Disruption of Interphotoreceptor Matrix Proteoglycans Results in Retinal Detachment", Invest. Ophthalmol. Vis. Sci. 33:2:364-376 (1992).

Lazarus et al., "Photoreceptor Degeneration and Altered Distribution of Interphotoreceptor Matrix Proteoglycans in the Mucopolysaccharidosis VII Mouse", Exp. Eye Res. 56:531-541 (1993).

Lewin, Benjamin *Genes IV*, 1990, p. 810, Oxford University Press.

Marmor et al., "Retinal Adhesiveness in Surgically Enucleated Human Eyes", Retina 14:181-186 (1994).

Miezlewska, "The Interphotoreceptor Matrix, a Space in Sight", Microsc. Res. Tech. 35:463-471 (1996).

Mieziewska, K.E., van Veen, T., Murray, J.M. & Aguirre, G.D. "Rod and cone specific domains in the interphotoreceptor matrix," J. Comp. Neurol. 308, 371-380 (1991).

Porrello and LaVail, "Immunocytochemical localization of chondroitin sulfates in the interphotoreceptor matrix of the normal and dystrophic rat retina", Curr. Eye Res. 5:12:981-993 (1986).

Prysiecki, Craig et al. "Occurrence of β-hydroxylated asparagines residues in non-vitamin K-dependent proteins containing epidermal growth factor-like domains" *Proc. Natl. Acad. Sci.*, Nov. 1987, pp. 7856-7860, vol. 84.

Russell and Hageman, "Insoluble Interphotoreceptor Matrix in Human Vitreous After Rhegmatogenous Retinal Detachment", Amer. J. Ophthalmol. 23:386-391 (1997).

Sambrook, J. et al. *Molecular Cloning: A Laboratory Manual, Second Edition,* 1989, pp. 9.47-9.50 & 11.48-11.49, Cold Spring Harbor Laboratory Press.

Skolnick, Jeffrey & Fetrow, Jacquelyn "From genes to protein structure and function: novel applications of computational approaches in the genomic era" *Trends in Biotech*, 2000, pp. 34-39, Vol. 18, No. 1.

Stone, E. et al. "Clinical features of a Stargardt-like dominant progressive macular dystrophy with genetic linkage to chromosome 6q," Arch. Ophthalmol. 112, 765-772 (1994).

Tate et al., "Age-Dependent Change in the Hyaluronic Acid Content of the Human Chorioretinal Complex", Arch. Ophthalmol. 111:963-967 (1993).

Wang, Xin et al. "Sequence analysis of PG10.2, a gene expressed in the pineal gland and the outer nuclear layer of the retina" *Mol. Brain Res.*, 1996, pp. 269-278, vol. 41, Elsevier.

Yao et al. "Recovery of Retinal Adhesion After Enzymatic Perturbation of the Interphotoreceptor Matrix", Invest. Ophthalmol. Vis. Sci. 33:3:498-503 (1992).

Yao et al., "Retinal Adhesiveness in the Monkey", Invest. Ophthalmol. Vis. Sci. 35:2:744-748 (1994).

Yao et al., "Retinal Adhesiveness is Weakened by Enzymatic Modification of the Interphotoreceptor Matrix in Vivo", Invest. Ophthalmol. Vis. Sci. 31:2051-2058 (1994).

\* cited by examiner

|             |   |   |   |   |   |   |   |   |   |   |   |   |   |   |   |   |   |   |   |
|-------------|---|---|---|---|---|---|---|---|---|---|---|---|---|---|---|---|---|---|---|
| Rat PG10.2  | S | I | L | F | P | N | G | V | R | I | C | P | S | D | T | A | E | A | V |
| Human 200   | X | A | L | F | P | N | G | V | L | I | X | P | X | E | V |   |   |   |   |
| Monkey 200  | X | I | L | F | P | N | G | V | L | I | X | P | D | E | V | X | K | E | I |
| Pig 200     | X | V | L | F | P | N | G | V | K | I | X | P |   |   |   |   |   |   |   |
| Human 150   | S | A | F | F | P | T | G | V | K | V | C | P | Q | E | E | S | M | K | Q | I | L |
| Monkey 150  | X | I | F | F | P | T | G | V | K | V | X | P | Q | E | E | S | M | K | Q | I | L |
| Pig 150     | X | V | F | F | P | T | G | V | K | V | X | P | Q | E | E | S | M | K | Q | I | L |

```
 14 IFLQVQGT.KDISINIYHSETKDIDNP........PRNETTESTEKMYKMSTMRRIFDLAKH...RTKRSAPPPTGVKVCPQESMKQILDSLQAYYRLRV 101
    ||.::|    :.  ||  .:| |          |   |  |   |  ||  : :   |:||  || |||:|| ||. : ..   |::.||
 16 IFVLIEGDFPSLTAQTYLS.IEEIQEPKSAVSFLLPEESTDLSLATKKKQPLDRR..ETERQWLIRRRRSILPPNGVKICPDESVAEAVANHVKYFKVRV 112

102 CQEAVWEAYRIFLDRIPDTGEYQDWVSICQQEFPCLFDIGKNFSNSQEHLDLLQQRIKQRSFPDRKDEISAEKTLGEP...GETIVISTDVANVSLGPFP 198
    |||||||:|  |  ||:|    ||   |..:|:     :|:.| ||| | ||  |: .::      |: :|.. |   |:| :    .| ||
113 CQEAVWEAFRTFWDRLPGREEYHYWMNLCEDGVTSIPEMGTNFSESVEHRSLIMKKLTY.....AKETVSSSE.LSSPVPVGDTSTLGDTTLSV...PHP 203

199 LT.............PDDTLLNEILDNTLNDTKNPTTERETEFAVLEEQRVELSVSLVNQKFKAELADSQSPYYQELAGKSQLQMQKIFKKLPGFKKIHV 285
                  |::..:  |||  :|  : :    |  |-  ||           |: |.  ..::  || ||| ::|    |   .  :.:   |  |||:|-|  |
204 EVDAYEGASESSLERPEESISNEI.ENVIEEATKPAGEQIAEF..........SIHLLGKQYREELQDSSSFHHQHLEEEFISEVENAFTGLPGYKEIRV 292

286 LGFRPKKEKDGSSSTEMQLTAIFKRHSAEAKSPAS.DLLSFDSNKIESEEVYHGTMEEDKQPEIYLTATDLKRLISKALEE.................. 365
    | ||  ||| | |:      |  -  || |  .||:| |||:|.   ||  .|| .|  :   | ..  |.. |::
293 LEFRSPKEND..SGVDVYYAVTF...NGEAISNTTWDLISLHSNKVEN....HGLVELDDKPTVVYTISNFRDYIAETLQQNFLLGNSSLNPDPDSLQLI 383

366 .......EQSLDV......GTIQFT................DE.IAGSLP..........AFGPDTQSELPTSFAVITEDATL.........SPE..... 411
           |.|.       .:||              |||  ||         |  :  |||   ||              |||
384 NVRGVLREQTEDLVWNTQSSSLQATPSSIILDNTFQAAWPSADESITSSIPPLDFSSGPPSATGRELWSESPLGDLVSTHKLAPPSKMGLSSSPEVLEVSS 483

412 ...........LPP............VEPQLETVDGAE.-..HGLPDTSWSPPAMAST..........SLSEAPPFMASSI.F...SLT....DQGT 464
               ||              : .|            ||. .|..|    :    |||  |     ||
484 LTLHSVTPAVLQTGLPVASEERTSGSHLVEDGLANVEESEDFLSIDSLPSSSFTQPVPKETIPSMEDSDVSLTSSP..YLTSSIPPGLDSLTSKVKDQLK 581

465 TDTMATDQTM..........LVPG.......LTIPTSDYSAISQLALGISHP..........PA.............SSD..........DSRSSAGGED. 514
    | .|          ||         :||| |: |.  . | :|  ||                  .|                |  ||            :  |||
582 VSPFLPDASMEKELIFDGGLGSGSGQKVDLITHPWSETSS.EKSAEPLSKPWLEDDDSLLPAEIEDKKLVLVDKMDSTDQISKHSKYEHDDRSTHFPEEE 680

515 ...........MVRHLDEM....DLSDTPAP...................SEVPELSEY.......VSV..PD........... 544
               : :|: |.    || ||                                          :: |||      ||. ||
681 PLSGPAVPIFADTAAESASLTLPKHISEVPGVDDCSVTKAPLILTSVAISASTDKSDQADAILREDMEQITESSNYEWFDSEVSMVKPDMQTLWTILPES 780

545 .......HFLE....D...TTPVSA.......................................................LQ........YI.......TTSSMTI 566
            ||       |    -|| ||                                                                                    .|      |:        .|  ..:
781 ERVWTRTSSLEKLSRDILASTPQSADRLWLSVTQSTKLPPTTISTLLEDEVIMGVQDISLELDRIGTDYYQPEQVQEQNGKVGSYVEMSTSVHSTEMVSV 880

567 A.P.KGRE..........LVVFPSLRVANMAPSNDLFNKSSLEYRALEQQFTQLLVPYLRSNLTGFKQLEILNFRNGSVIVNSKMKFAKSVPYNLTKAVH 654
    | | .| :          ||||||||| || || |||||-||||:|||-| :||||||.||||||.  ||||||||||::|||:|||| ||| |.  ||:
881 AWPTEGGDDLSYTQTSGALVVFFSLRVTNMMFSEDLFNKNSLEYKALEQRFLELLVPYLQSNLTGFQNLEILNFRNGSIVVNSRMKFANSVPPNVNNAVY 980

655 GVLEDFRSAAAQQLHLEIDSYSLNIEPADQADPCKFLACGEFAQCVKNERTEEAESCRCKPGYDSQGSLDGLEPGLCGPGTKE......CEVLQGKGAPCR 748
    :||||  . |   :.| || |||.:|  |:|.||||  ||  ||.:|. |   .  ||.||| |||  |              ||                |:::.|-|| ||
981 MILEDFCTTAYNTMNLAIDKYSLDVESGDEANPCKFQACNEFSECLVNPWSGEAKCRCFPGYLSVEERPCQS..LCDLQPDFCLNDGKCDIMPGHGAICR 1078
```

Fig. 3

NUCLEIC ACIDS ENCODING INTERPHOTORECEPTOR MATRIX PROTEINS

CROSS-REFERENCES TO RELATED APPLICATIONS

This patent application is a continuation-in-part of U.S. application Ser. No. 09/430,195, abandoned, filed Oct. 29, 1999, which is a continuation-in-part of U.S. application Ser. No. 09/183,972, abandoned, filed Oct. 29, 1998. The disclosures of these previously filed applications are hereby incorporated by reference in their entirety for all purposes.

STATEMENT AS TO RIGHTS TO INVENTIONS MADE UNDER FEDERALLY SPONSORED RESEARCH AND DEVELOPMENT

Work described herein has been supported, in part, by NIH grants EY06463 and EY11515. The U.S. Government can therefore have certain rights in the invention.

FIELD OF THE INVENTION

This invention relates to therapeutics and diagnostics for ocular abnormalities.

BACKGROUND OF THE INVENTION

The normal anatomic relationship between the retina and the choroid is crucial to eye function. In many ocular diseases or abnormalities such as, for example, chorioretinal degenerations, retinal degenerations, macular degenerations and retinal detachment, the integrity of this relationship is compromised. One of the most common ocular disorders is macular degeneration (MD), a clinical term that is used to describe a variety of diseases that are all characterized by a progressive loss of central vision associated with abnormalities of Bruch's membrane and the retinal pigment epithelium (RPE) (See FIG. 1). These disorders include very common conditions that affect older patients (age-related macular degeneration, or AMD), as well as rarer, earlier-onset dystrophies.

AMD is a significant cause of irreversible blindness worldwide. There is strong evidence that a significant proportion of AMD has a genetic foundation (Gorin et al., MB, Mol Vis. 1999,5:29; Heiba et al., Genet. Epidemiol. 1994; 1:51-67; Seddon et al., Am. J. Ophthalmol. 1997;123:199-206; and Klein et al., Arch. Ophthalmol. 1994;1 12:932-7). Several AMD loci have been identified (Weeks et al., Hum. Mol. Genet. 20009:1329-49; and Klein et al., Arch. Ophthalmol. 1998;116:1082-8). In addition, the ApoE4 allele has been shown to be protective for the disease (Klaver et al., Am J Hum Genet 1998;63:200-6).

The interphotoreceptor matrix (IPM) is an extracellular matrix comprised of an array of proteins, glycoproteins, and proteoglycans, occupying the space between the apical surfaces of the neural retina and the RPE. Hageman and Kuehn (1998), The Pigmented Retinal Epithelium: Current Aspects of Function and Disease, pp. 417-454; Hageman and Johnson (1991), Progr. in Ret. Res. 10:207-209; Hewitt and Adler (1989), Retina 1:57-64; Mieziewska (1996), Microsc. Res. Tech. 15;35:463-471. The IPM is crucial for normal function and viability of retinal photoreceptor cells. It can participates in the exchange of metabolites and catabolic byproducts between the retinal pigment epithelium and photoreceptor cells, the regulation of the subretinal ionic milieu, and the orientation, polarization, and turnover of photoreceptor outer segments (Marmor et al., Arch. Ophthalmol. 1995; 113:232-8; Bok et al., Arch. Ophthalmol. 1993;111:463-71; Hageman et al., Proc. Natl. Acad. Sci. U.S.A 1991;88:6706-6710; Hewitt et al., The retinal pigment epithelium and interphotoreceptor matrix: Structure and specialized function, In: T. Ogden, Editor Retina, St. Louis, Mo., C. V. Mosby Co., 1989, 57-64; and Lazarus et al., Invest. Ophthal. Vis. Sci. 1992,33:364-375). IPM proteoglycans have been shown to mediate photoreceptor cell adhesion (Yao et al., Invest. Ophth. Vis. Sci. 1990,31:2051-2058; Hageman et al., Arch. Ophthalmol. 1995;113:655-660; Marmor et al., Retina 1994;14:181-186; and Hollyfield et al., Retina 1989,9:59-68). IPM 200 and IPM 150 may also mediate photoreceptor cell survival by sequestration of growth factors (Hageman et al., Proc. Natl. Acad. Sci. U.S.A, 1991, 88:6706-6710; and Alberdi et al., Biochem. 1998, 37:10643-52) or through the EGF-like domains contained within their core proteins (Kuehn and Hageman, Mol. Cell Biol. Res. Commun. 1999; 2:103-110; Kuehn and Hageman, Matrix Biology 1999;18:509-518; and Kuehn et al., Mol. Vis. 2000;6:148-56).

Photoreceptor cells are highly vulnerable to dysfunction and/or death in various heritable retinal dystrophies and degenerations (Stone et al., Prog. Retin. Eye Res. 1999;18: 689-735). Nucleotide sequence variations in the genes encoding a number of retinal proteins are associated with the etiology of various retinal degenerations. For example, mutations in the genes encoding retinal rhodopsin, beta-phosphodiesterase, rab geranylgeranyl transferase, rim protein, and the RP1 gene product cause retinal degeneration (Dryja et al., Nature 1990;343:364-6; McLaughlin et al., Nat. Genet. 1993;4:130-4; Guillonneau et al., Hum. Mol. Genet. 19998:1541-6; Allikmets, Nat. Genet. 1997;17:122; and Seabra et al., Science 1993;259:377-81).

Cone matrix sheaths (CMSs), distinct domains of the IPM that contain chondroitin 6-sulfate proteoglycan and surround cone photoreceptor cells, have firm attachments to both RPE cells and the neural retina. This adhesive system is sufficiently strong to detach the RPE or tear the CMS following manual separation of the neural retina from the RPE. Hageman et al.(1995), Arch. Ophthalmol. 113:655-660. The role of IPM constituents in mediating retinal adhesion has been investigated following subretinal or intravitreal injections of various enzymes into rabbit eyes and examination of the consequent morphological, biochemical and physiological changes in retinal structure and function. Chondroitinase ABC, neuraminidase and testicular hyaluronidase, three enzymes that degrade oligosaccharides known to be constituents of the IPM, caused diffuse loss of adhesion that is associated with changes in peanut agglutinin (PNA)-binding to CMSs, without affecting photoreceptor function (based on ERG recordings). Yao et al (1990), Invest. Ophthalmol. Vis. Sci. 31:2051-2058; Yao et al. (1992), Invest. Ophthalmol. Vis. Sci. 33:498-503. Enzymatic cleavage of IPM-associated chondroitin sulfate glycosaminoglycans leads to a rapid decrease of retinal adhesiveness in both rabbits and primates in vivo. Yao et al (1990), Invest. Ophthalmol. Vis. Sci. 31:2051-2058; Yao et al. (1994), Invest. Ophthalmol. Vis. Sci. 35:744-748. In addition, disruption of proteoglycan synthesis in vivo leads to loss of CMS-associated chondroitin 6-sulfate proteoglycans, IPM disruption, localized retinal detachments and photoreceptor outer segment degeneration. Lazarus and Hageman (1992), Invest. Ophthalmol. Vis. Sci. 33:364-376. Restoration of retinal adhesion, which recovers steadily between 5 and 20 days following exposure to chondroitinase and neuraminidase, correlates closely with the re-establishment of the normal distribution of PNA-binding glycoconjugates in the IPM. Restoration of impaired adhesion is concomitant with the de novo biosynthesis of IPM chondroitin sulfate proteoglycans. Yao et al. (1992), *Invest. Ophthalmol. Vis. Sci*. 33:498-503. Thus, it is likely that specific components of the IPM act as major adhesive elements bridging the RPE-retina interface, and that these elements are critically dependent on the metabolic function of RPE and neural retina cells in the microenvironment of the IPM.

Studies in which monkey and human eyes are removed immediately following euthanasia or optic crossclamp, respectively, and the retinas partially "peeled" from the RPE reveal that CMSs remain firmly attached to both the apical RPE and neural retina and elongate up to 4-6 times their normal length in eyes peeled within 45 seconds of enucleation. Additional peeling separation results in separation of the entire RPE from Bruch's membrane, or splitting of the CMSs. These results suggest that adhesion between CMS constituents and the RPE or photoreceptors is stronger than that of the integrity of the CMSs themselves and, as such, provide evidence that CMSs have characteristics consistent with their participation in the establishment and maintenance of retinal attachment. Hageman et al. (1995), *Arch. Ophthalmol*. 113:655-660; Yao et al. (1990), *Invest. Ophthamol. Vis. Sci*. 33:498-503.

IPM proteoglycans can be involved in the differentiation and maintenance of specific retinal cells and/or with the establishment of physical interactions between photoreceptor and RPE cells. Recent studies have demonstrated that chondroitin sulfate-containing proteoglycans are first detectable in the mouse IPM a few days prior to the elaboration of photoreceptor outer segments. In human retinas, CMS constituents bound by PNA and the chondroitin 6-sulfate antibody (AC6S) are expressed at a time during development when rudimentary cone outer segments first differentiate. Concentrated accumulations of PNA-binding constituents are observed at 17 to 18 weeks. Chondroitin 6-sulfate is first detected in the IPM between 20 and 23 weeks, when rudimentary cone outer segments begin to differentiate and is solely associated with cone outer segments. At this time, cone photoreceptors are well-polarized and enlarged domes of IPM are associated with them. These studies suggest that there is a staggered expression of PNA- and AC6S-containing IPM constituents, and that the CMSs and IPM constituents can be necessary for subsequent cone outer segment differentiation and survival. This contention is further supported by observations that photoreceptors exhibit some degree of polarity but are unable to maintain differentiated outer segments in culture. In addition, RPE-conditioned medium causes a significant increase in the number of embryonic chick photoreceptor cells forming outer segment-like structures in vitro and stimulate their survival and differentiation.

A number of studies suggest a correlation between changes in IPM composition and the etiology of photoreceptor demise in some degenerations. In the "Royal College of Surgeons" (RCS) rat, or mucopolysaccharidosis VII (MPS VII) mouse, for example, alterations in the distribution of IPM chondroitin 6-sulfate proteoglycan occur prior to photoreceptor degeneration. Chu et al. (1992), *Graefes Arch. Clin. Exp. Ophthalmol*. 230:476-482; Johnson et al. (1989), *Inherited and Environmentally Induced Retinal Degenerations*, pp. 217-232; Lazarus et al. (1993), *Exp. Eye Res*. 54:531-541; Porello and LaVail (1986), *Curr. Eye Res*. 5:981-993. Similarly, intravitreal injection of β-D-xylopyranoside, a sugar that inhibits GAG chain addition to proteoglycan core proteins, results in cone outer segment degeneration following loss of CMS-associated chondroitin 6-sulfate. These studies strongly indicate that disruption of the normal synthesis or turnover of chondroitin sulfate proteoglycans can lead to cone outer segment degeneration.

The density of rods with abnormal IPM has been shown to increase in correlation with increasing quantities of macular drusen, extracellular deposits in Bruch's membrane associated with AMD. Preliminary analyses of neutral and amino sugars from the IPM of retinas with and without significant numbers of these "PNA-binding rods" show a decrease in IPM sialic acid concentration. In addition, the densities of PNA-binding rods correlate with drusen grade. The incidence of cone degeneration in these same eyes can be as high as 30-40%, in contrast to age-matched controls without significant macular drusen, where cone photoreceptor loss is approximately 12-15%. These studies provide direct evidence that changes in IPM proteoglycan composition are associated with drusen, and that these changes can be related to photoreceptor dysfunction and visual loss that occurs in individuals with AMD.

The vitronectin receptor (VnR) is associated with apical RPE and cone photoreceptor outer and inner segment plasma membranes. VnR co-localizes with components of apposed CMSs at these cell surfaces, and with actin cables within apical RPE microvilli and cone photoreceptor inner segments. Based on the known functions of VnR, it is likely that its interaction with IPM ligands can modulate other cellular activities, such as translation of external cues into signals that affect cytoskeletal organization or modification of other IPM ligands.

Discovery of novel IPM components allows identification of novel therapeutic and diagnostic agents for diseases or conditions associated with abnormal IPM, such as retinal detachment, chorioretinal degenerations, retinal degenerations and macular degenerations such as AMD, or other dystrophies or degenerations involving IPM, cones or rods.

SUMMARY OF THE INVENTION

In one aspect, the invention provides isolated or recombinant IPMC (e.g., IPM 150 or IPM 200) polynucleotides. The IPMC polynucleotides comprise a nucleotide sequence or its complement, wherein said nucleotide sequence hybridizes under stringent conditions to (i) at least 540 contiguous nucleotide residues of SEQ ID NO: 1, 3, 5, or 27; (ii) at least 216 contiguous nucleotide residues of SEQ ID NO: 16, 18, or 20; or (iii) at least 100 contiguous nucleotide residues of SEQ ID NO: 8, 10, 12, 14, 23, or 25. Some of the IPMC polynucleotides comprise, or are complementary to, (i) at least 540 contiguous nucleotide residues of SEQ ID NO: 1, 3, 5, or 27; (ii) at least 216 contiguous nucleotide residues of SEQ ID NO: 16, 18, or 20; or (iii) at least 100 contiguous nucleotide residues of SEQ ID NO: 8, 10, 12, 14, 23, or 25. Some of the IPMC polynucleotides comprise, or are complementary to, the sequence set forth in any one of SEQ ID NOs: 1, 3, 5, 8, 10, 12, 14, 16, 18, 20, 23, 25, and 27.

Some of the IPMC polynucleotides comprise a nucleotide sequence or its complement, wherein the nucleotide sequence encodes a IPMC polypeptide comprising (i) at least 180 contiguous amino acid residues of SEQ ID NO: 2, 4, 6, or 28; (ii) at least 72 contiguous amino acid residues of SEQ ID NO: 17, 19, or 21; or (iii) at least 33 contiguous amino acid residues of SEQ ID NO: 9, 11, 13, 15, 24, or 26. Some of the IPMC polynucleotides comprise a nucleotide sequence encoding the amino acid sequence of SEQ ID NO: 2, 4, 6, 9, 11, 13, 15, 17, 19, 21, 24, 26, or 28.

In other aspects, the invention also provides vectors comprising a promoter of an IPMC gene operatively linked to one of the above-described IPMC polynucleotides. Some of the vectors comprise a promoter that is obtained from the sequence set forth in SEQ ID NO: 7 or 22.

In another aspect, the present invention provides isolated or recombinant IPMC polypeptides which comprise an amino acid sequence that is substantially identical to (i) at least 180 contiguous amino acid residues of SEQ ID NO: 2, 4, 6, or 28; (ii) at least 72 contiguous amino acid residues of SEQ ID NO: 17, 19, or 21; or (iii) at least 33 contiguous amino acid residues of SEQ ID NO: 9, 11, 13, 15, 24, or 26. Some of the IPMC polypeptides comprise (i) at least 180 contiguous amino acid residues of SEQ ID NO: 2, 4, 6, or 28; (ii) at least 72 contiguous amino acid residues of SEQ ID NO: 17, 19, or 21; or (iii) at least 33 contiguous amino acid residues of SEQ ID NO: 9, 11, 13, 15, 24, or 26. Some of the IPMC polypeptides comprise the amino acid sequence set forth in any one of SEQ ID NOs: 2, 4, 6, 9, 11, 13, 15, 17, 19, 21, 24, 26, and 28. In other aspects, the invention also provides anti-IPMC antibodies that specifically bind to IPMC polypeptides.

In still another aspect, the invention provides methods for treating or preventing the development of a disease or condition in a subject by administering to the subject an effective amount of an IPMC therapeutic. In some methods, the disease or condition to be treated is photoreceptor death. In other methods, the disease or condition to be treated is retinal detachment. In some methods, the IPMC therapeutic administered is a IPMC polynucleotide. In some methods, the IPMC therapeutic administered is a IPMC polypeptide. In some methods, the IPMC therapeutic is an antibody that specifically binds to an IPMC polypeptide.

The present invention further provides methods for identifying a compound capable of modulating IPMC gene expression in a cell. The methods comprise (i) incubating a cell with a test compound under conditions that permit the compound to exert a detectable regulatory influence over an IPMC gene, thereby altering the IPMC gene expression; and (ii) detecting an alteration in said IPMC gene expression. In some methods, the IPMC gene to be modulated is human IPM 150 gene or human IPM 200 gene.

BRIEF DESCRIPTION OF THE FIGURES

FIG. 2 is an alignment of the N-terminal amino acid sequences of rat IPMC 200 protein (SEQ ID NO: 29), human IPM 200 (SEQ ID NO: 17), monkey IPM 200 (SEQ ID NO: 24), pig IPM 200 (SEQ ID NO: 30), human IPM 150 (SEQ ID NO: 28), monkey IPM 150 (SEQ ID NO: 15), and pig IPM 150 (SEQ ID NO: 31).

FIG. 3 is an alignment of the human IPM 150 and IPM 200 amino acid sequences (amino acid 14-748 of SEQ ID NO: 28 and amino acid 16-1078 of SEQ ID NO: 17, respectively).

DETAILED DESCRIPTION OF THE INVENTION

Overview

Figure 1:
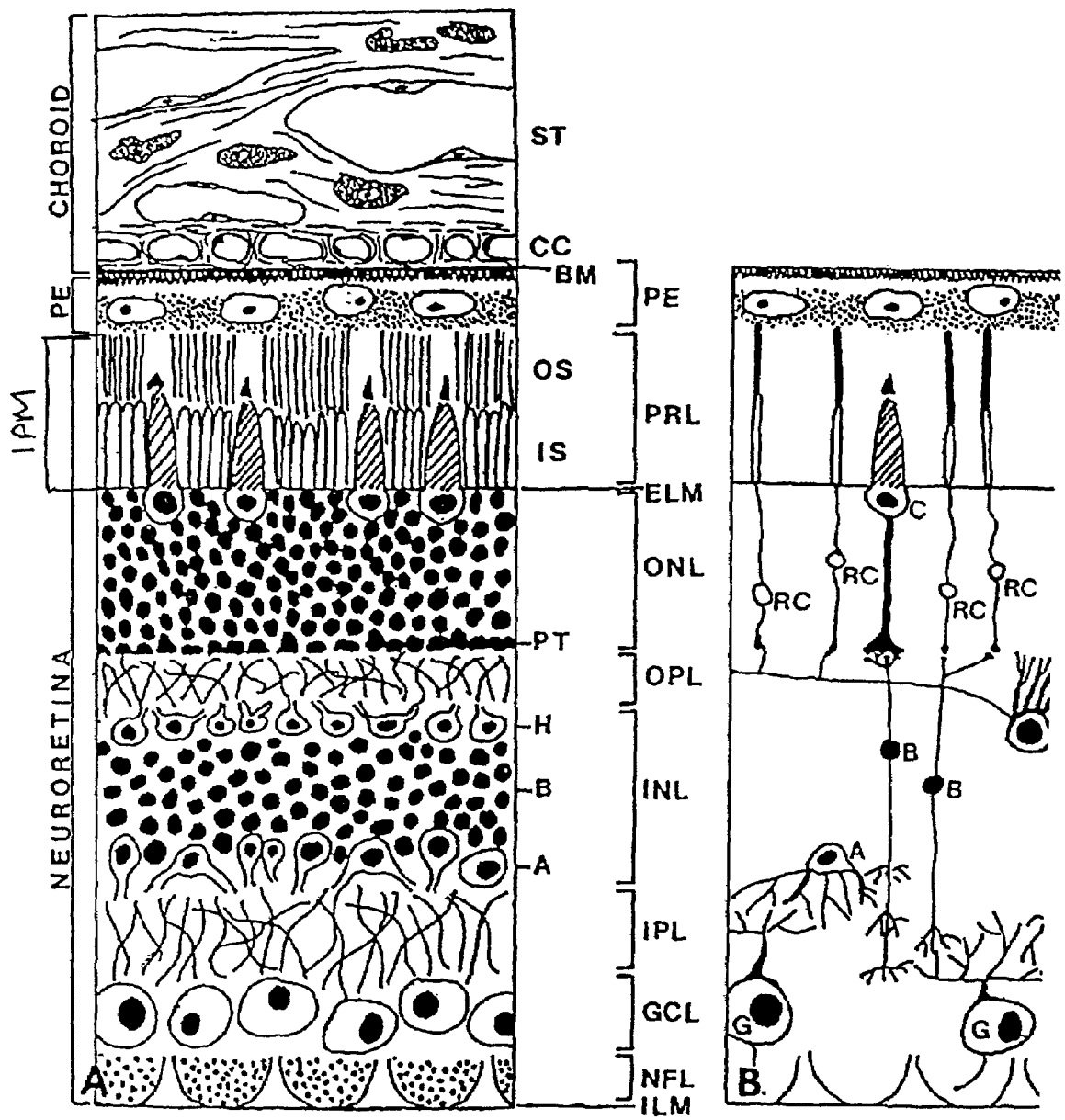
FIG. 1 is a schematic representation of retina and choroid. (A) As seen in histological section, (B) Retinal neurons shown diagrammatically. A, amacrine cells; B, bipolar cells; BM, Bruch's membrane; C, cone cells; CC, choroidocapillaris; ELM, external limiting membrane; G, ganglion cells; GCL, ganglion cell layer; H, horizontal cells; ILM, inner limiting membrane; INL, internal nuclear layer; IPM, interphotoreceptor matrix; IS, inner segments of rods and cones; IPL, internal plexiform layer; NFL, nerve fiber layer; ONL, outer nuclear layer; OPL, outer plexiform layer; OS, outer segments of rods and cones; PE, pigment epithelium; PRL, photoreceptor layer; PT, photorecptor cell terminals; RC, rod cells; ST, stroma vascularis of choroid.

The present invention is based, at least in part, on the discovery of a novel family of mammalian polynucleotides and proteins isolated from the interphotoreceptor matrix (IPM). This newly identified gene family is referred to as the interphotoreceptor matrix component or "IPMC" gene family. Members of the IPMC gene family have been identified in humans, monkey, cow, goat, rabbit, dog, cat, pig, mouse and rat IPM. Two subfamilies of IPMCs are designated the IPM 150 (also termed "IMPG1") family and the IPM 200 (also termed "IMPG2") family, respectively, based upon sequence similarity and homology of the various mammalian cDNAs, genes and proteins to human IPM 150 or human IPM 200 cDNAs, genes and proteins, respectively. The core proteins of primate IPM 150 and IPM 200 proteins are unique, based on partial amino acid sequences obtained from the N-terminal and internal peptides, and on deduced amino acid sequences obtained from a PCR product derived from monkey and human retinal cDNA encoding portions of IPM 150 and IPM 200. Partial amino acid sequences of the N-termini of IPM 150 and IPM 200 are similar, but exhibit specific inter- and intra-species differences.

A. IPMC Sequences

1 Human IPM 150

The IPM 150 gene is located on chromosome 6q13-q15, between markers CHLC.GATA11F10 and D6S284, which region also contains loci for progressive bifocal chorioretinal atrophy, autosomal dominant Stargardt's-like macular dystrophy, North Carolina macular dystrophy and Salla disease. Kelsell et al. (1998), *Am. J. Hum. Genet.* 53:274-279; Felbor et al. (1998), *Cytogenet. Cell Genet.* 81:12-17; Gehrig et al. (1998), *J. Med. Genet.* 35:641-645.

SEQ ID NO: 1 shows cDNA sequence of human IPM 150, isoform A. It encodes 17 exons with boundaries as follows: exon 1 (1-195), exon 2 (196-431), exon 3 (432-595), exon 4 (596-627), exon 5 (628-688), exon 6 (689-797), exon 7 (798-934), exon 8 (935-996), exon 9 (997-1015), exon 10 (1016-1265), exon 11 (1266-1340), exon 12 (1341-1421), exon 13 (1422-1953), exon 14 (1954-2174), exon 15 (2175-2373), exon 16 (2374-2449), and exon 17 (2450-3268). The corresponding amino acid sequence of human IPM 150 isoform A is shown in SEQ ID NO. 2. It contains a signal peptide (residues 1-20), a NH-terminal domain (71-88), conserved domain 1 (95-115), conserved domain 2 (575-646), and an EGF-like domain (688-731).

SEQ ID NOs: 27 and 28 are the cDNA sequence and amino acid sequence encoding a variant of human IPM 150 isoform A. Compared to SEQ ID NO: 2 (full length human IPM 150 protein sequence), SEQ ID NO: 28 lacks the last 25 amino acids but has nine residues at the C-terminal that are not present in SEQ ID NO: 2.

Two human IPM 150 cDNA splicing isoform sequences, IPM 150 isoform B and isoform C have also been identified. The cDNA sequence of isoform B is shown in SEQ ID NO. 3. The open reading frame corresponds to residues 2-2140. Compared to isoform A, Isoform B has a deletion of exon 2 (at residue 50). It encodes a 719 amino acids human IPM 150 isoform B protein (SEQ ID NO. 4). The amino acid sequence has a signal sequence (residues 1-20), a conserved domain (residues 497-568), and an EGF-like domain (residues 586-628).

IPM 150 isoform C contains an insertion after exon 5 and a stop codon at nucleotide 744, creating a truncated protein with a hydrophobic carboxyl terminus. The cDNA and amino acid sequences encoding human IPM 150 isoform C are shown in SEQ ID NOs. 5 and 6. SEQ ID NO. 5 has an ORF from residue 94 to residue 744. Compared to isoform A, IPM 150 isoform C has an insertion of exon 5B (residues 713 to 774). SEQ ID NO. 6 has a signal sequence (1-20), a N-terminal domain (residues 71 to 88), and a conserved domain (95-115).

The regulatory region of human IPM 150 gene is shown in SEQ ID NO. 7. Residues 1-1069 of SEQ ID NO. 7 are the upstream IPM 150 promoter sequence. Residues 1070 to 1268 in SEQ ID NO. 7 correspond to exon 1.

2. Mouse IPM 150

The mouse IPM 150 gene is located on chromosome 9, between markers D9Mit264 and D9Mit265. SEQ ID NOs. 8 and 9 are cDNA and amino acid sequences of mouse IPM 150 isoform A, respectively. Residues 196-2589 of SEQ ID NO. 8 correspond to the open reading frame. The 798 amino acid residues of SEQ ID NO. 9 contain a NH-terminal domain (71-80), conserved domain 1 (95-125), a mucin-like domain (405 to 577), conserved domain 2 (576-657), and an EGF-like domain (697-740).

The cDNA and amino acid sequences of mouse IPM 150 cDNA isoform D are shown in SEQ ID NOs. 10 and 11. Mouse IPM isoform D cDNA sequence (SEQ ID NO. 10) does not contain nucleotides 264-493 and 1487-2251 of mouse IPM 150 isoform A cDNA sequence (SEQ ID NO. 8). SEQ ID NO. 10 has an ORF from residue 140 to residue 1537. The deletions are located at residues 205 and 1198 of SEQ ID NO. 10, respectively. The mouse IPM 150 isoform D protein has a signal sequence (1-20), a conserved domain (21-49), and an EGF-like domain (360-408).

SEQ ID NOs. 12 and 13 are cDNA and amino acid sequences encoding mouse IPM 150 isoform E. Compared to isoform A (SEQ ID NO. 8), SEQ ID NO. 12 has a deletion at position 325 that corresponds to residues 372-1788 of SEQ ID NO. 8. Residues 1-20 of SEQ ID NO. 13 encode a signal peptide.

3. Monkey IPM 150

SEQ ID NO. 14 is a cDNA sequence encoding monkey IPM 150. It encodes a 185 amino acid sequence (SEQ ID NO. 15). The monkey IPM 150 protein sequence (SEQ ID NO. 15) has a NH-terminus domain (residues 1-18) and a conserved domain (residues 24-244).

4. Human IPM 200

The human IPM 200 gene is located on chromosome 3, 5.76cR from the marker WI-3277 in the region of 3q12.2-12.3. Human IPM 200 appears to be a homolog of PG10.2 and mouse IPM 200. SEQ ID NO. 16 is the cDNA sequence of human IPM 200 (isoform A). The human IPM 200 cDNA sequence has O- and N-linked glycosylation consensus sequences, as well as glycosaminoglycan attachment sites, two EGF-like domains, a transmembrane domain and clustered cysteine residues. It encodes 19 exons; exon 1 (1-274), exon 2 (277-525), exon 3 (526-692), exon 4 (693-724), exon 5 (725-774), exon 6 (775-857), exon 7 (858-1019), exon 8 (1020-1078), exon 9 (1079-1099), exon 10 (1100-1344), exon 11 (1345-1430), exon 12 (1431-1734), exon 13 (1735-2993), exon 14 (2994-3213), exon 15 (3216-3426), exon 16 (3427-3613), exon 17 (3615 3825), exon 18 (3826-3906), and exon 19 (3906-4166).

The human IPM 200 cDNA encodes a membrane bound isoform of human IPM 200. SEQ ID NO. 17 shows the amino acid sequence of human IPM 200. It has a signal peptide (residues 1-29), a N-terminus domain (82-92), conserved domain 1 (106-130), conserved domain 2 (898-979), an EGF-like domain (1050-1092), a transmembrane domain (1097-1127), and a cytoplasmic domain (residues 1128-1241). In addition, residues 154-156, 301-303, 320-322, 942-944, and 956-958 contain N-glycosylation sites, and residues 603-606 contain a GAG attachment site.

The cDNA and amino acid sequences encoding human IPM 200 isoform C are shown in SEQ ID NOs. 18 and 19. Residues 90-1385 of SEQ ID NO. 18 correspond to the open reading frame. Compared to isoform A cDNA sequence, SEQ ID NO. 18 has a deletion at position 1327 of residues 1431-1668 of SEQ ID NO. 16 (part of exon 12). SEQ ID NO. 19 has a signal sequence (residues 1-29), a NH-terminus domain (82-92), and a conserved domain 1 (106-130).

SEQ ID NOs. 20 and 21 are the cDNA and amino acid sequences encoding human IPM 200 isoform F. Compared to SEQ ID NO. 18 (isoform A), the cDNA sequence of isoform F has a deletion at residue 188 which corresponds to nucleotides 310-3461 of isoform A. Residues 1-29 of SEQ ID NO. 21 encode the signal peptide.

The upstream regulatory sequence of human IPM 200 is shown in SEQ ID NO. 22 (residues 1-1450). Residues 1451-1723 and 2177-2425 correspond to IPM exons 1 and 2, respectively.

5. Mouse IPM 200

Mouse IPM 200 cDNA and amino acid sequences are shown in SEQ ID NOs. 23 and 24. Residues 2-3208 of SEQ ID NO. 23 correspond to the open reading frame. This sequence encodes a partial mouse IPM 200 protein sequence (SEQ ID NO. 24) which lacks a N-terminal portion of the protein. The mouse IPM 200 protein sequence contains O- and N-linked glycosylation consensus sequences which correspond in position to those in the human sequence, with a hydrophobic domain which can constitute a transmembrane domain. Mouse IPM 200 appears to be a homolog of PG10.2, an uncharacterized sequence tag expressed in the pineal gland and retina of rats.

6. Monkey IPM 200

SEQ ID NO. 25 shows a partial cDNA sequence of monkey IPM 200. The open reading frame is from residue 188 to residue 546. It encodes a N-terminal fragment of monkey IPM 200 protein (SEQ ID NO. 26). Residues 82-114 of SEQ ID NO. 26 correspond to a native NH-terminus domain.

In addition to human, mouse, and monkey IPM sequences discussed above, partial amino acid sequences of rat IPM 200, pig IPM 200, and pig IPM 150 molecules are shown in SEQ ID NOs: 29, 30, and 31, respectively.

Figure 4:
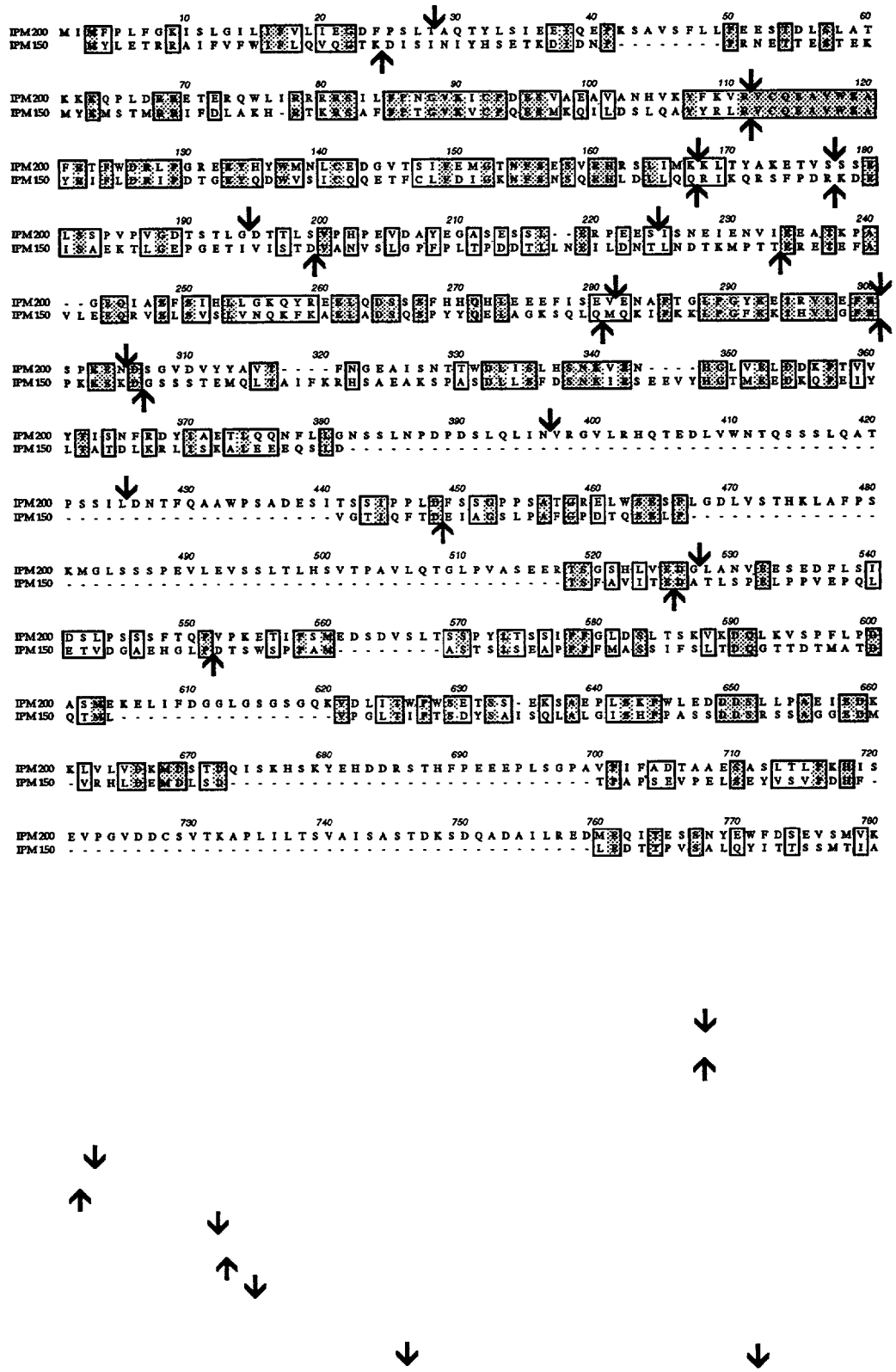
FIG. 4 shows organization and comparison of the IPM 200 (top) and IPM 150 (bottom) genes and their encoded proteins. Regions of high sequence homology are indicated by black boxes, regions of moderate homology are indicated by dark shaded boxes and regions displaying low sequence homology are represented by lightly shaded boxes. The borders between exons are marked by vertical lines. Thin horizontal lines indicate the insertion of gaps. EGF-like domains are represented by ovals and the hydrophobic, putative transmembrane domain of IPM 200 is depicted by a diamond.

IPMC sequence identity in different species has been found by sequence alignment. For example, an alignment of IPM 150 and IPM 200 N-terminal amino acid sequences from humans, monkeys and pigs reveals a high degree of sequence conservation between the species (FIG. 2). Sequence identity is also found between IPM 150 and IPM 200 molecules. FIGS. 3 and 4 show alignment between amino acid sequences of human IPM 150 and IPM 200.

B. Characterization and Functions of IPMC molecules

Unless otherwise noted, characterization of IPM 150 and IPM 200 molecules is described with reference to the sequences of human IPM 150 isoform A and human IPM 200 isoform A. The amino acid sequence of human IPM 150 isoform A revealed a novel protein that is generally hydrophilic except for the first 18 amino acids, which form a hydrophobic region flanked by charged amino acid residues. The amino acid sequence features O- and N-linked glycosylation consensus sequences, an EGF-like domain, a single glycosaminoglycan attachment consensus sequence, two clusters of cysteine residues, and two potential hyaluronan binding motifs.

There are four consensus sequences for N-linked glycosylation (Kornfield and Kornfield (1985), *Ann. Rev. of Biochem.* 54:631-664) sequestered in the amino-terminus (amino acid residues 42, 143, 191 and 215) and four probable consensus sequences in the carboxy-terminus (amino acid residues 592, 616, 630 and 648) portions of the human IPM 150 core protein. In contrast, the central domain of IPM 150 (between amino acid residues 221 and 565) contains 16 sites which are suitable for O-linked glycosylation, as predicted by a proposed algorithm for the activity of polypeptide N-acetylgalactosaminyl-transferase (amino acid residues 221, 222, 407, 433, 435, 441, 442, 443, 445, 470, 497, 527, 531, 537, 561 and 565). Hansen et al. (1995), *Biochem. J.* 308:801-813. There is almost no overlap between the regions containing potential O- and N-linked glycosylation sites. Further, a glycosaminogycan (GAG) attachment site is located at amino acid residue 296.

Several cysteine residues are also present in the amino- and carboxy-terminal regions of the IPM 150 core protein. The distribution of the carboxy-terminal cysteine residues closely resembles that of EGF-like domains (Rees et al. (1988), *EMBO J.* 7:2053-2061) (amino acid residues 688-731), motifs that are present in many extracellular matrix proteins. One reported function of the domain is to promote the survival of neighboring cells. Thus, this region of IPM 150 can have a role in promoting photoreceptor viability in vivo. This contention is supported by previous studies indicating that the IPM, and more specifically its proteoglycans, are important in maintaining photoreceptor cell viability. Lazarus and Hageman (1992), *Invest. Ophthalmol. Vis. Sci.* 33:364-376; Blanks et al (1993), *Exp. Eye Res.* 57:265-273.

Hyaluronan is an IPM component (see, Hageman and Kuehn (1998), The Pigmented Retinal Epithelium: Current Aspects of Function and Disease, pp. 417-454; and Korte et al. (1994), *Microscopy Res. Tech.* 29:344-349). It is also known that hyaluronidase disrupts CMSs in vitro and weakens retinal adhesion in vivo. On the other hand, the N-terminus of IPM 150 possesses hyaluronan binding domains. Thus, IPM 150 can play a role in retinal adhesion through interaction with hyaluronan. For example, hyaluronan can play a role in stabilizing the IPM through interactions with CD44, IPM 150, IPM 200 and perhaps other insoluble IPM constituents.

With the exception of the amino-terminal signal sequence, which appears to be removed during the maturation of IPM 150, the core protein does not possess any other hydrophobic regions that would constitute transmembrane domains. This indicates that IPM 150 is secreted into the interphotoreceptor space and is not membrane intercalated. Based on previous studies indicating a role for IPM proteoglycans in adhesion of the neural retina to the RPE (Hageman et at. (1995), *Arch. Ophthalmol.* 113:655-660; Hollyfield et al. (1989), *Retina* 9:59-68; Yao et al. (1992), *Invest. Ophthalmol. Vis. Sci.* 33:498-503; Yao et al. (1994), *Invest. Ophthalmol. Vis. Sci.* 35:744-748), IPM 150 can act as a bridging element between membrane-associated molecules on the photoreceptor and RPE cell surfaces to effect retinal adhesion. For example, IPM 150 can bind to the vitronectin receptor, which is localized to the surfaces of photoreceptor outer segments and the apical microvilli of RPE cells. The chondroitin-sulfate glycosaminoglycans of IPM 150 might also participate in retinal adhesion, through receptors like CD44 (Toyama-Sorimachi et al. (1995), *J. Biol. Chem.* 270:7437-7444), an adhesion molecule associated with Muiller cell apical microvilli in mice and humans (Hageman and Kuehn (1998), The Pigmented Retinal Epithelium: Current Aspects of Function and Disease, pp. 417-454).

Human IPM 150 cDNA probes hybridize to a 3.9 kb transcript that is present in relatively high abundance in retinal RNA. A larger transcript of approximately 6.5 kb is also detected, albeit at a much reduced signal strength. Distinct hybridization of IPM 150 antisense riboprobes to the human retinal outer nuclear layer (ONL) was observed on sections of human retina, RPE and choroid. IPM 150 transcripts are present within both rod and cone photoreceptor cells. In addition, IPM 150 (or a related molecule) is transcribed in non-ocular tissues. Dot-blot analyses of mRNA derived from a variety of human tissues indicate that IPM 150-derived probes hybridize to human adult and fetal lung and thymus, as well as to adult kidney and small intestine. In addition, ESTs partially homologous to the IPM 150 cDNA sequence have been identified from human endothelial cell and brain cDNA libraries.

The mouse IPM 150 amino acid sequence also has O- and N-linked glycosylation consensus sequences, an EGF-like domain, five glycosaminoglycan attachment consensus sequence, one cluster of cysteine residues, and several potential hyaluronan binding motifs, which correspond in position to those in the human sequence. Northern blot analysis suggests that IPM 150 mRNA is expressed in retinal tissue.

The human IPM 200 cDNA sequence encodes nineteen O-linked glycosylation sites (amino acid residues 183, 191, 400, 408, 430, 439, 482, 496, 533, 537, 556, 624, 718, 730, 801, 813, 815, 822, and 870) and six N-linked glycosylation sites (amino acid residues 154, 301, 320, 370, 942 and 956). The IPM 200 cDNA encodes a GAG attachment site at amino acid residue 604. IPM 200 may also be expressed in non-ocular tissues (Wang et al., Molec. Brain Res. 1996; 41:269-278; and Acharya et al., J Biol Chem 2000;275: 6945-55).

The above data indicate that IPMC molecules function generally as extracellular matrix proteins in a number of tissues, and in particular play a role in retinal adhesion (e.g., by interacting with hyaluronan). The evidence also indicate that abnormal IPMC activities can be involved in diseases or conditions such as retinal detachment or chorioretinal degeneration.

C. The subject invention

In accordance with the above-described discovery, the present invention provides IPMC polynucleotides, IPMC polypeptides encoded by the IPMC polynucleotides, and antibodies that are specific for the IPMC polypeptides.

The present invention provides methods for diagnosing the presence or a predisposition to the development of an ocular disorder associated with abnormal IPMC activities (e.g., retinal detachment or macular degeneration). The invention also provides methods for treating or preventing the development of ocular disease or disorders related to abnormal IPMC activities using IPMC therapeutics. IPMC therapeutics include, but are not limited to, IPMC polynucleotides, IPMC polypeptides, and IPMC polypeptide specific antibodies. The present invention also provides methods for establishing IPMC expression profiles for ocular diseases or disorders, and methods for diagnosing and treating an ocular disease or disorder using such expression profiles.

Polynucleotide arrays comprising IPMC polynucleotides are also provided. IPMC nucleic acids or polynucleotides of the invention are useful for inclusion on a GeneChip™ array or the like for use in expression monitoring (see U.S. Pat. No. 6,040,138, . EP 853, 679 and WO97/27317). Such arrays typically contain oligonucleotide or cDNA probes to allow detection of large numbers of mRNAs within a mixture. Many of the nucleic acids included in such arrays are from genes or ESTs that have not been well characterized. Such arrays are often used to compare expression profiles between different tissues or between different conditions of the same tissue (healthy vs. diseased or drug-treated vs. control) to identify differentially expressed transcripts. The differentially expressed transcripts are then useful e.g., for diagnosis of disease states, or to characterize responses of drugs. The IPMC nucleic acids of the invention can be included on GeneChip™ arrays or the like together with probes containing a variety of other genes. The IPMC nucleic acids are particularly useful for inclusion in GeneChip™ arrays for analyzing ocular tissues or cells. The IPMC nucleic acids can be combined with nucleic acids from other genes having roles in ocular diseases or disorders (as described above). Such arrays are useful for analyzing and diagnosing cells in ocular diseases such as retinal detachment. Such arrays are also useful for analyzing candidate drugs for roles in modulation of a disease state.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). Although any methods and materials similar or equivalent to those described herein can be used in the practice or testing of the present invention, the preferred methods and materials are described. For convenience, the meaning of certain terms and phrases employed in the specification, examples, and appended claims are provided below to assist the reader in the practice of the invention.

The term "an aberrant activity", as applied to an activity of a polypeptide such as an IPMC protein, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity or in its binding characteristics. For example an aberrant polypeptide can interact with a different target peptide. A cell can have an aberrant IPMC protein activity due to overexpression or underexpression of the gene encoding an IPMC protein.

The terms "abnormal" or "abnormality" refers to a condition which differs from that found normally. Such abnormality when referring to a sequence means a change in the sequence such as an addition, deletion or change (e.g., substitution of nucleic acid or amino acid for another nucleic acid or amino acid, respectively). For example, such abnormality when referring to protein activity means a change in the expression level of RNA or protein, RNA or protein turnover, activity or binding characteristics. Such abnormality when referring to a medical condition means a difference in the structure, function or composition of an organ, system, cell or organism.

The term "agonist" refers to an agent that mimics or upregulates (e.g. potentiates or supplements) or otherwise increases an IPMC bioactivity. An IPMC agonist can be a wild-type IPMC protein or derivative thereof having at least one bioactivity of a wild-type IPMC protein. An agonist can also be a compound which increases the interaction of an IPMC polypeptide with another molecule, e.g., an upstream region of a gene, which is regulated by an IPMC transcription factor.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation. The term "allelic variant of a polymorphic region of an IPMC gene" refers to a region of an IPMC gene having one or several nucleotide sequences found in that region of the gene in other individuals.

The term "antagonist" refers to an agent that downregulates (e.g. suppresses or inhibits) at least one IPMC bioactivity. An IPMC antagonist can be a compound which inhibits or decreases the interaction between an IPMC protein and another molecule, e.g., an upstream region of a gene, which is regulated by an IPMC transcription factor. Accordingly, a preferred antagonist is a compound which inhibits or decreases binding to an upstream region of a gene, which is regulated by an IPMC transcription factor and thereby blocks subsequent activation of the IPMC protein. An antagonist can also be a compound that downregulates expression of an IPMC gene or which reduces the amount of IPMC protein present, e.g., by decreasing protein synthesis or increasing protein turnover. The IPMC antagonist can be a dominant negative form of an IPMC polypeptide, e.g., a form of an IPMC polypeptide which is capable of interacting with an upstream region of a gene, which is regulated by an IPMC transcription factor, but which is not capable of regulating transcription. The IPMC antagonist can also be a nucleic acid encoding a dominant negative form of an IPMC polypeptide, an IPMC antisense nucleic acid, or a ribozyme capable of interacting specifically with an IPMC RNA. Yet other IPMC antagonists are molecules which bind to an IPMC polypeptide or its receptor and inhibit its action. Such molecules include peptides, antibodies and small molecules.

The term "antisense sequences" refers to polynucleotides having sequence complementary to a RNA sequence. These terms specifically encompass nucleic acid sequences that bind to mRNA or portions thereof to block transcription of mRNA by ribosomes. Antisense methods are generally well known in the art (see, e.g., PCT publication WO 94/12633, and Nielsen et al., 1991, Science 254:1497; OLIGONUCLEOTIDES AND ANALOGUES, A PRACTICAL APPROACH, edited by F. Eckstein, IRL Press at Oxford University Press (1991); ANTISENSE RESEARCH AND APPLICATIONS (1993, CRC Press)).

"Biological activity" or "bioactivity" or "activity" or "biological function", which are used interchangeably, for the purposes herein means an effector or antigenic function that is directly or indirectly performed by an IPMC polypeptide (whether in its native or denatured conformation), or by any subsequence thereof. Biological activities include binding to a target nucleic acid e.g., an upstream region of a gene, which is regulated by an IPMC transcription factor. An IPMC bioactivity can be modulated by directly affecting an IPMC polypeptide. Alternatively, an IPMC bioactivity can be modulated by modulating the level of an IPMC polypeptide, such as by modulating expression of an IPMC gene or by modulating the turnover of the IPMC protein.

The term "bioactive fragment of an IPMC polypeptide" refers to a fragment of a full-length IPMC polypeptide, wherein the fragment specifically mimics or antagonizes the activity of a wild-type IPMC polypeptide. The bioactive fragment preferably is a fragment capable of interacting with e.g., an upstream region of a gene, which is regulated by an IPMC transcription factor.

A "chimeric polypeptide" or "fusion polypeptide" is a fusion of a first amino acid sequence encoding one of the subject IPMC polypeptides with a second amino acid sequence defining a domain (e.g. polypeptide portion) foreign to and not substantially homologous with any domain of an IPMC polypeptide. A chimeric polypeptide can present a foreign domain which is found (albeit in a different polypeptide) in an organism which also expresses the first polypeptide, or it can be an "interspecies", "intergenic", etc. fusion of polypeptide structures expressed by different kinds of organisms.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

The term "disease or condition associated with abnormal IPMC activity" is a condition in which an IPMC molecule is abnormally expressed. The IPMC molecule can abnormally be overexpressed or underexpressed, for example. The activity of the IPMC molecule can be abnormal in that its functional activity can be increased or decreased. The activity of the IPMC molecule can be abnormal by having changed its function. Such a change in function can be a consequence of a change in the nucleic acid sequence or a change in its protein sequence.

The term "extracellular matrix" ("ECM") refers to the collagens, proteoglycans, non-collagenous glycoproteins and elastins that can surround cells and provide structural support for cells as well as maintain various functions of cells, such as cell adhesion, proliferation and differentiation. See, for example, Aszódi et al. (1998), J. Mol. Med. 76:238-252; Bruckner-Tuderman et al. (1998), J. Mol. Med. 76:226-237; Aumailley et al. (1998), J. Mol. Med. 76:253-265. A skilled artisan will appreciate that the precise composition and physical properties of ECM, as well as its function, varies between various cell types and between various organs.

The term "hybridizes" refers to the annealing of one nucleic acid sequence to another. Appropriate stringency conditions which promote DNA hybridization, for example, 2 to 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. The salt concentration in the wash step can be selected from a low stringency of about 6.0×SSC to a high stringency of about 0.1×SSC. In addition, the temperature in the wash step can be increased from low stringency conditions at room temperature, about 22° C., to high stringency conditions at about 65° C. Formamide can be added to the hybridization steps and washing steps in order to decrease the temperature requirement by 1° C. per 1% formamide added. The term "specifically hybridizes" or "specifically detects" refers to the ability of a nucleic acid molecule of the invention to hybridize to at least approximately 6, 12, 20, 30, 50, 100, 150, 200, 250, 300, 350, 400, 450, 500, 1000, 1500, 2000, 2500, 3000, 4000, or 4165 consecutive nucleotides of a vertebrate gene, preferably an IPMC gene.

The terms "IPMC polypeptide" and "IPMC protein" are interchangeable and refer to the family comprising polypeptides or proteins having the amino acid sequences shown as SEQ ID NO: 2, 4, 6, 9, 11, 13, 15, 17, 19, 21, 24, 26, or 28, or fragments thereof, mutant and allelic variants, and homologs thereof.

The term "IPMC nucleic acid" and "IPMC polynucleotides" are interchangeable and refer to a nucleic acid encoding an IPM 150 or an IPM 200 protein, such as nucleic acids having SEQ ID NO: 1, 3, 5, 8, 10, 12, 14, 16, 18, 20, 23, 25, or 27, as well as fragments thereof, complements thereof, mutant and allelic variants, homologs, and derivatives thereof.

The term "IPMC therapeutic" refers to various forms of IPMC polypeptides, as well as peptidomimetics, nucleic acids, or small molecules, which can modulate at least one activity of an IPMC polypeptide, e.g., binding to and/or otherwise regulating expression of a gene, by mimicking or potentiating (agonizing) or inhibiting (antagonizing) the effects of a naturally-occurring IPMC polypeptide. An IPMC therapeutic which mimics or potentiates the activity of a wild-type IPMC polypeptide is an "IPMC agonist". Conversely, an IPMC therapeutic which inhibits the activity of a wild-type IPMC polypeptide is an "IPMC antagonist".

"Homology" or "identity" or "similarity" refers to sequence similarity between two peptides or between two nucleic acid molecules and can be determined by comparing a position in each sequence which can be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. An "unrelated" or "non-homologous" sequence shares less than about 40% identity, though preferably less than about 25% identity, with one of the IPM protein sequences of the present invention. Percentage identity, homology or similarity are determined using a sequence alignment software as described herein. Alternatively percentage identity, homology or similarity are determined by the number of nucleotide or amino acid differences in a sequence of a certain length. For example, a 100 residue sequence with 20 residue differences is defined as 80% identical, wherein a difference means a different residue or lack of residue. "Homologous" refers to the evolutionary relatedness of two nucleic acid or protein sequences. "Identity" refers to the degree to which nucleic acids or amino acids are the same between two sequences. "Similarity" refers to the degree to which nucleic acids or amino acids are the same, but includes neutral amino acid substitutions that do not significantly change the function of the protein as is well known in the art. Similarity also refers to neutral degenerate nucleic acids that can be substituted within a codon without changing the amino acid identity of the codon, as is well known in the art.

The term "macular degeneration" refers to a condition in which the macula degenerates, e.g., as a consequence of decreased growth of cells of the macula, increased death or rearrangement of the cells of the macula, or a combination of these events. Macular degeneration results in the loss of integrity of the histoarchitecture of the cells of the normal macula and/or the loss of function of the cells of the macula. Any condition which alters or damages the integrity or function of the macula can be considered to fall within the definition of macular degeneration. Other examples of diseases in which cellular degeneration has been implicated include retinal detachment, chorioretinal degenerations, retinal degenerations, photoreceptor degenerations, RPE degenerations, mucopolysaccharidoses VII, rod-cone dystrophies, cone-rod dystrophies and cone degenerations.

The term "modulation" refers to both upregulation (i.e., activation or stimulation (e.g., by agonizing or potentiating)) and downregulation (i.e. inhibition or suppression (e.g., by antagonizing, decreasing or inhibiting)).

"Small molecule" refers to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate an IPMC bioactivity.

The term "substantially sequence identity," refers to two or more sequences or subsequences that have at least 60%, preferably 80%, most preferably 90%, 95%, 98%, or 99% nucleotide or amino acid residue identity, when compared and aligned for maximum correspondence, as measured using one of the following sequence comparison algorithms or by visual inspection. Two sequence (amino acid or nucleotide) can be compared over their full-length (e.g., the length of the shorter of the two, if they are of substantially different lengths) or over a subsequence such as at least about 50, about 100, about 200, about 500 or about 1000 contiguous nucleotides or at least about 10, about 20, about 30, about 50 or about 100 contiguous amino acid residues.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols In Molecular Biology, Greene Publishing and Wiley-Interscience, New York (supplemented through 1999). Each of these references and algorithms is incorporated by reference herein in its entirety. When using any of the aforementioned algorithms, the default parameters for "Window" length. gap penalty, etc., are used.

One example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Alignments may also be carried out using CLUSTAL (Higgins et al., CLUSTAL V: multiple alignment of DNA and protein sequences. Methods Mol Biol 1994;25:307-18) using the default parameters.

A further indication that two nucleic acid sequences or polypeptides are substantially identical is that the polypeptide encoded by the first nucleic acid is immunologically cross reactive with the polypeptide encoded by the second nucleic acid. Thus, a polypeptide is typically substantially identical to a second polypeptide, for example, where the two peptides differ only by conservative substitutions.

Another indication that two nucleic acid sequences are substantially identical is that the two molecules hybridize to each other under stringent conditions. Substantial identity exists when the segments will hybridize under stringent hybridization conditions to a strand, or its complement, typically using a sequence of at least about 50 contiguous nucleotides derived from the probe nucleotide sequences. "Stringent hybridization conditions" refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel (1987) Methods In Enzymology, Vol. 152: Guide To Molecular Cloning Techniques, San Diego: Academic Press, Inc. and Sambrook et al., et al., 1989, MOLECULAR CLONING: A LABORATORY MANUAL, (2nd ed.) Vols. 1-3, Cold Spring Harbor Laboratory. As indicated by standard references, a simple estimate of the Tm value may be calculated by the equation: $Tm=81.5+0.41(\% G+C)$, when a nucleic acid is in aqueous solution at 1 M NaCl (see e.g., Anderson and Young, "Quantitative Filter Hybridization" in Nucleic Acid Hybridization (1985)). Other references include more sophisticated computations which take structural as well as sequence characteristics into account for the calculation of Tm. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel, supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 60° C. for long probes (e.g., greater than 50 nucleotides). As noted, stringent conditions may also be achieved with the addition of destabilizing agents such as formamide, in which case lower temperatures may be employed.

The terms "substantially pure" or "isolated," when referring to proteins and polypeptides, e.g., IPMC polypeptides, denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition. When referring to polynucleotides, the terms "substantially pure" or "isolated" generally refer to the polynucleotide separated from contaminants with which it is generally associated, e.g., lipids, proteins and other polynucleotides. The substantially pure or isolated polynucleotides of the present invention will be greater than about 50% pure. Typically, these polynucleotides will be more than about 60% pure, more typically, from about 75% to about 90% pure and preferably from about 95% to about 98% pure.

The following sections provide guidance for making and using the compositions of the invention, and carrying out the methods of the invention.

III. IPMC polypeptides and Variants

A. IPMC polypeptides

The invention provides substantially pure, isolated, or recombinant IPMC polypeptides. Some IPMC polypeptide have an amino acid sequence identical or substantially identical to the amino acid sequence shown in SEQ ID NO: 2, 4, 6, 9, 11, 13, 15, 17, 19, 21, 24, 26, or 28. The polypeptide of the invention can be full-length or can encode a fragment of the full-length protein. Some of the IPMC polypeptide fragments comprise an amino acid sequence that is substantially identical to at least about 8, 10, 11, 12, 14, 16, 25, 35, 50, 60, 70, 72, 74, 76, 100, 150, 175, 177, 179, 180, 182, 184, 190, 200, 250, or 500 contiguous amino acid residues of SEQ ID NO: 2, 4, 6, 9, 11, 13, 15, 17, 19, 21, 24, 26, or 28. Some of the IPMC polypeptides share greater than 50%, 60%, 70%, 80%, 90%, 95%, or 99% sequence identity to SEQ ID NO: 2, 4, 6, 9, 11, 13, 15, 17, 19, 21, 24, 26, or 28. Some of the IPMC polypeptides are encoded by all or a portion of a sequence shown in any of SEQ ID NOs: 1, 3, 5, 8, 10, 12, 14, 16, 18, 20, 23, 25, and 27.

Also provided by the invention are IPMC polypeptides that are modified, relative to the amino acid sequence of SEQ ID NO: 2, 4, 6, 9, 11, 13, 15, 17, 19, 21, 24, 26, or 28, in some manner, e.g., truncated, mutated, derivatized, or fused to other sequences (e.g., to form a fusion protein). Some IPMC polypeptides comprise insertions, deletions or substitutions of amino acid residues relative to SEQ ID NO: 2, 4, 6, 9, 11, 13, 15, 17, 19, 21, 24, 26, or 28. For example, some conservative amino acid substitutions can be made, i.e., substitution of selected amino acids with different amino acids having similar structural characteristics, e.g., net charge or hydrophobicity.

The IPMC polypeptides of the present invention can be glycosylated, or conversely, by choice of the expression system or by modification of the protein sequence to preclude glycosylation, reduced carbohydrate analogs can also be provided. Glycosylated forms can be obtained, for example, based on derivitization with glycosaminoglycan chains.

The modified IPMC polypeptides of the invention can have some or all of the biological activities of naturally-occurring, full-length IPMC polypeptide (e.g., IPM 150 or IPM 200). Some of the IPMC polypeptides preferably are capable of functioning as either an agonist or antagonist of at least one biological activity of a wild-type ("authentic") IPMC protein. The modified polypeptides proteins can also be resistant to post-translational modification, e.g., due to mutations which alter modification sites (such as tyrosine, threonine, serine or asparagine residues), or which prevent glycosylation of the protein, or which prevent interaction of the protein with intracellular proteins involved in signal transduction.

Some IPMC polypeptides contain one or more of the conserved domains of IPM 150 or IPM 200. They can contain at least one of the EGF-like domains or the conserved domains of SEQ ID NO. 2, 4, 6, 9, 11, 15, 17, 19, 26, or 28 that are defined in the previous sections. For example, the IPMC polypeptides can contain one or more of the NH-terminal domain (71-88), conserved domain 1 (95-115), conserved domain 2 (575-646), and an EGF-like domain (688-731) of SEQ ID NO: 2. Some other IPMC polypeptides contain one or more of the four main domains of the IPM 150 protein, namely domain A, B, C or D. Domain A is located in the amino terminus of the protein, from residue 42 to 215 of SEQ ID NO: 28, containing four possible glycosylation sites (amino acids 42, 143, 191 and 215). Domain B is a central domain containing 17 possible O-linked glycosylation sites from residue 221 to 565 of SEQ ID NO: 28 (amino acids 221, 222, 406, 433, 435, 441, 442, 443, 445, 470, 497, 527, 529, 537, 561 and 565). Domain C is located in the carboxy terminus of the protein, from residue 591 to 630 of SEQ ID NO: 28 and contains four probable N-linked glycosylation sites (amino acids 591, 592, 616 and 630). Domain D is located in the carboxy-terminus of the protein and contains a hyaluronan binding consensus sequence at residues 735 to 743 of SEQ ID NO: 28 and an EGF-like domain between amino acids 688 to 731 of SEQ ID NO: 28.

Some IPMC polypeptides or fragments can be used as an immunogen to produce anti-IPMC antibodies. Typically, the immunogenic IPMC fragments of the invention comprise at least about 6 contiguous residues of the IPMC sequence, e.g., SEQ ID NO: 2, 4, 6, 9, 11, 13, 15, 17, 19, 21, 24, 26, or 28, more often at least about 8, about 15, or about 20, or about 25 contiguous residues. Some of the immunogenic IPMC fragments comprise at least 35, 50, 72, 177, or more contiguous amino acid residues of SEQ ID NO: 2, 4, 6, 9, 11, 13, 15, 17, 19, 21, 24, 26, or 28.

Some of the IPMC polypeptides can bind to antibodies that are specifically immunoreactive with a polypeptide having the sequence shown in SEQ ID NO: 2, 4, 6, 9, 11, 13, 15, 17, 19, 21, 24, 26, or 28. Specific immunoreactivity is usually characterized by a specific binding affinity of an antibody for its ligand of at least $10^7$, $10^8$, $10^9$, or $10^{10}$ M$^{-1}$.

B. Production and Isolation of IPMC polypeptides

The IPMC polypeptides of the present invention can be prepared using recombinant or synthetic methods, or can be isolated from natural cellular sources. Suitable recombinant techniques for expressing IPMC polypeptides from the IPMC polynucleotides are disclosed infra. See also, Sambrook et al., 1989, MOLECULAR CLONING: A LABORATORY MANUAL, (2nd ed.) Vols. 1-3, Cold Spring Harbor Laboratory, and in Ausubel, supra. Synthetic methods for synthesizing polypeptides such as IPMC polypeptides, variants, or fragments are described in Merrifield, 1963, *Amer. Chem. Soc.* 85:2149-2456, Atherton et al., 1989, SOLID PHASE PEPTIDE SYNTHESIS: A PRACTICAL APPROACH, IRL Press, and Merrifield, 1986, Science 232:341-347.

Isolation and purification of the IPMC polypeptides of the present invention can be carried out by methods that are generally well known in the art. These methods include, but are not limited to, ion exchange, hydrophobic interaction, HPLC or affinity chromatography, to achieve the desired purity. The IPMC polypeptides can be purified using immunoaffinity chromatography. For example, antibodies raised against a IPMC polypeptide or immunogenic fragment thereof (e.g., having a sequence or subsequence of SEQ ID NO: 2, 4, 6, 17, 19, 21, or 28) are coupled to a suitable solid support and contacted with a mixture of polypeptides containing the IPMC polypeptide (e.g., a homogenate of brain tissue) under conditions conducive to the association of this polypeptide with the antibody. Once the IPMC polypeptide is bound to the immobilized antibody, the solid support is washed to remove unbound material and/or nonspecifically bound polypeptides. The desired polypeptide can then be eluted from the solid support in substantially pure form by, e.g., a change in pH or salt concentration of the buffer.

C. IPMC Polypeptide Analogs and Mimetics

Although primarily described in terms of "proteins" or "polypeptides," structural analogs and derivatives of the above-described polypeptides, e.g., peptidomimetics, and the like can be used as substitutes for IPMC, e.g., as IPMC activity agonists, or, alternatively, as IPMC activity antagonists. Peptidomimetics, or peptide mimetics, are peptide analogs commonly used in the pharmaceutical industry as non-peptide drugs with properties (e.g., a biological activity) analogous to those of the template peptide. (Fauchere, 1986, *Adv. Drug Res.* 15:29; Evans et al., 1987, *J. Med. Chem.* 30:1229). They are usually developed with the aid of computerized molecular modeling. Peptide mimetics that are structurally similar to therapeutically useful peptides can be used to produce an equivalent therapeutic effect. Peptide mimetics can have significant advantages over polypeptide embodiments, including, for example, more economical production and greater chemical stability.

IV. IPMC Polynucleotides

The invention provides a polynucleotide having a sequence or subsequence of a mammalian (e.g., rat or human) IPMC gene or RNA. The polynucleotides of the invention (e.g., RNA, DNA, PNA or chimeras), and may be single-stranded, double stranded, or a mixed hybrid. The IPMC polynucleotides can have various number of bases or base pairs in length. Some of the polynucleotides have a sequence of SEQ. ID NO: 1, 3, 5, 7, 8, 10, 12, 14, 16, 18, 20, 22, 23, 25, or 27, or subsequences thereof. Some of the IPMC polynucleotides comprise a nucleotide sequence that is substantially identical to a number of contiguous nucleotides of SEQ ID NOs: 1, 3, 5, 7, 8, 10, 12, 14, 16, 18, 20, 22, 23, 25, or 27. The number can be at least 15, 20, 25, 29, 30, 31, 35, 50, 75, 100, 150, 200, 215, 216, 217, 218, 250, 300, 350, 400, 450, 500, 539, 540, 541, 542, 550, 750, 1000, 1500, 2000, or more.

The invention also provides polynucleotides with substantial sequence identity to the IPMC polynucleotides disclosed herein. Thus, the invention provides IPMC polynucleotide sequences having one or more nucleotide deletions, insertions or substitutions relative to a IPMC nucleic acid sequence of SEQ ID NO: 1, 3, 5, 7, 8, 10, 12, 14, 16, 18, 20, 22, 23, 25, or 27.

Some of the polynucleotides encode a polypeptide with substantial sequence identity to SEQ. ID NO: 2, 4, 6, 9, 11, 13, 15, 17, 19, 21, 24, or 26, or encodes a fragment of such a polypeptide (e.g., a fusion protein). Some of the IPMC polynucleotides comprise a nucleotide sequence that is not substantially identical to SEQ ID NO: 1, 3, 5, 8, 10, 12, 14, 16, 18, 20, 23, or 25. Rather, due to the degeneracy of the genetic code, they encode the polypeptide of SEQ. ID NO: 2, 4, 6, 9, 11, 13, 15, 17, 19, 21, 24, or 26 or a fragment thereof. Some IPMC polynucleotides that do not necessarily encode IPMC polypeptide but are useful as e.g., probes, primers, antisense, triplex, or ribozyme reagents The invention also provides expression vectors, cell lines, and transgenic animals or organisms comprising the IPMC polynucleotides. Some of the vectors, cells, or transgenic animals or organisms are capable of expressing the encoded IPMC polypeptides.

Using the guidance of this disclosure, the IPMC polynucleotides of the invention can be produced by recombinant means. See, e.g., Sambrook et al., (1989) Molecular Cloning: A Laboratory Manual, 2nd Ed., Vols. 1-3, Cold Spring Harbor Laboratory; Berger and Kimmel, (1987) Methods In Enzymology, Vol. 152: Guide To Molecular Cloning Techniques, San Diego: Academic Press, Inc.; Ausubel et al., Current Protocols In Molecular Biology, Greene Publishing and Wiley-Interscience, New York (1999). Alternatively, IPMC polynucleotides or fragments can be chemically synthesized using routine methods well known in the art (see, e.g., Narang et al., 1979, Meth. Enzymol. 68:90; Brown et al., 1979, Meth. Enzymol. 68:109; Beaucage et al., 1981, Tetra. Lett., 22:1859). Some IPMC polynucleotides of the invention contain non-naturally occurring bases (e.g., deoxyinosine) or modified backbone residues or linkages that are prepared using methods as described in, e.g., Batzer et al., 1991, Nucleic Acid Res. 19:5081; Ohtsuka et al., 1985, J. Biol. Chem. 260:2605-2608; Rossolini et al., 1994, Mol. Cell. Probes 8:91-98.

A. Polynucleotides Encoding IPMC Polypeptides

In one aspect, the invention provides polynucleotides encoding IPMC polypeptides such as an IPMC polypeptide comprising the sequence of SEQ ID NO: 2, 4, 6, 9, 11, 13, 15, 17, 19, 21, 24, 26, or 28, a fragment thereof, a variant thereof (e.g., a conservative or allelic variant), or a IPMC fusion polypeptide. In one embodiment, the polynucleotide of the invention comprises the sequence of SEQ ID NO: 1, 3, 5, 8, 10, 12, 14, 16, 18, 20, 23, 25, or 27, or a fragment thereof. Some of the polynucleotides encode a naturally occurring IPMC polypeptide or fragment, but has a sequence that differs from SEQ. ID NO: 1, 3, 5, 8, 10, 12, 14, 16, 18, 20, 23, 25, or 27 (e.g., as a result of the degeneracy of the genetic code).

Some of the IPMC polynucleotides encode at least one of the domains (e.g., EGF-like domain or conserved domain) of SEQ ID NO. 2, 4, 6, 9, 11, 15, 17, 19, 26, or 28. They can also encode one of the four main domains of human IPM 150 (i.e., domains A, B, C, and D, as described above).

The polynucleotides of invention are useful for expression of IPMC polynucleotides (e.g., sense or antisense RNAs) and polypeptides. Methods for recombinant expression of polynucleotides and proteins are well known in the art. Typically, the IPMC polynucleotides of the invention are used in expression vectors for the preparation of IPMC polypeptides and polynucleotides. Expression vectors typically include transcriptional and/or translational control signals (e.g., the promoter, ribosome-binding site, and ATG initiation codon). In addition, the efficiency of expression can be enhanced by the inclusion of enhancers appropriate to the cell system in use. For example, the SV40 enhancer or CMV enhancer can be used to increase expression in mammalian host cells.

To produce IPMC polypeptides, the IPMC polynucleotides encoding an IPMC polypeptide is inserted into DNA constructs capable of introduction into and expression in an in vitro host cell, such as a bacterial (e.g., *E. coli, Bacillus subtilus*), yeast (e.g., Saccharomyces), insect (e.g., *Spodoptera frugiperda*), or mammalian cell culture systems. Examples of mammalian cell culture systems useful for expression and production of the polypeptides of the present invention include human embryonic kidney line (293; Graham et al., 1977, J. Gen. Virol. 36:59); CHO (ATCC CCL 61 and CRL 9618); human cervical carcinoma cells (HeLa, ATCC CCL 2); and others known in the art. The use of mammalian tissue cell culture to express polypeptides is discussed generally in Winnacker, FROM GENES TO CLONES (VCH Publishers, New York, N.Y., 1987) and Ausubel, supra.

To produce IPMC polypeptides, promoters from mammalian genes or from mammalian viruses can be used, e.g., for expression in mammalian cell lines. Suitable promoters can be constitutive, cell type-specific, stage-specific, and/or modulatable or regulatable (e.g., by hormones such as glucocorticoids). Useful promoters include the metallothionein promoter, the constitutive adenovirus major late promoter, the dexamethasone-inducible MMTV promoter, the SV40 promoter, and promoter-enhancer combinations known in the art.

IPMC polypeptides or fragments can also be expressed in transgenic animals (mouse, sheep, cow, etc.) and plants (tobacco, arabidopsis, etc.) using appropriate expression vectors which integrate into the host cell chromosome.

B. IPMC Polynucleotide or Oligonucleotide Probes and Primers

The invention provides oligonucleotide or polynucleotide probes and/or primers for detecting or amplifying IPMC polynucleotides. Some of the polynucleotides (e.g., probes and primers) comprise at least 10 contiguous bases identical or exactly complementary to SEQ ID NO: 1, 3, 5, 7, 8, 10, 12, 14, 16, 18, 20, 22, 23, 25, or 27, usually at least 12 bases, typically at least 15 bases, generally at least 18 bases and often at least 25, at least 50, or at least 100 bases When the IPMC polynucleotides of the invention are used as probes or primers, they are generally less than about 3000 bases in length; typically they contain between about 12 and about 100 contiguous nucleotides identical or exactly complementary to SEQ. ID NO: 1, 3, 5, 7, 8, 10, 12, 14, 16, 18, 20, 22, 23, 25, or 27, more often between about 12 and about 50 contiguous nucleotides, even more often between about 15 and about 25 contiguous nucleotides. Some of the probes and primers having a sequence of SEQ ID NO: 1, 3, 5, 16, 18, 20, or 27, or a fragment thereof, are used in the methods (e.g., diagnostic, therapeutic methods, and screening methods) of the invention or in preparation of pharmaceutical compositions.

Some of the probes and primers are modified, e.g., by adding restriction sites to the probes or primers. Some primers or probes of the invention comprise additional sequences, such as linkers. Some primers or probes of the invention are modified with detectable labels. For example, the primers and probes are chemically modified, e.g., derivatized, incorporating modified nucleotide bases, or containing a ligand capable of being bound by an anti-ligand (e.g., biotin).

The IPMC primers of the invention can be used for a number of purposes, e.g., for amplifying an IPMC polynucleotide in a biological sample for detection, or for cloning IPMC genes from a variety of species. Using the guidance of the present disclosure, primers can be designed for amplification of an IPMC gene or isolation of other IPMC homologs.

C. IPMC Inhibitory Polynucleotides

The invention provides inhibitory polynucleotides such as antisense, triplex, and ribozyme reagents that target or hybridize to IPMC polynucleotides. These polynucleotides can be used to treat disease states which are associated with elevated activity of IPMC bioactivities.

1. Antisense Polynucleotides

The present invention provides antisense oligonucleotides and polynucleotides that can be used to inhibit expression of the IPMC gene. Some therapeutic methods of the invention, described in additional detail infra, involve the administration of an oligonucleotide that functions to inhibit or stimulate IPMC activity under in vivo physiological conditions, and is relatively stable under those conditions for a period of time sufficient for a therapeutic effect. Polynucleotides can be modified to impart such stability and to facilitate targeting delivery of the oligonucleotide to the desired tissue, organ, or cell.

The antisense polynucleotides of the invention comprise an antisense sequence of at least about 10 bases, typically at least 20, at least about 50, or at least about 100, and up to at least about 1000 to at least about 3000 contiguous nucleotides that specifically hybridize to a sequence from mRNA encoding IPMC polypeptides or mRNA transcribed from an IPMC gene. More often, the antisense polynucleotide of the invention is from about 12 to about 50 nucleotides in length or from about 15 to about 25 nucleotides in length. In general, the antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, peptide nucleic acid, phosphorothioate), among other factors.

Generally, to assure specific hybridization, the antisense sequence is substantially complementary to the target IPMC mRNA sequence. Some antisense sequences are exactly complementary to the target sequences. The antisense polynucleotides can also include, however, nucleotide substitutions, additions, deletions, transitions, transpositions, or modifications, or other nucleic acid sequences or non-nucleic acid moieties so long as specific binding to the relevant target sequence corresponding to IPMC RNA or its gene is retained as a functional property of the polynucleotide.

Some of the antisense sequences are complementary to relatively accessible sequences of the IPMC mRNA (e.g., relatively devoid of secondary structure). This can be determined by analyzing predicted RNA secondary structures using, for example, the MFOLD program (Genetics Computer Group, Madison Wis.) and testing in vitro or in vivo as is known in the art. Another useful method for identifying effective antisense compositions uses combinatorial arrays of oligonucleotides (see, e.g., Milner et al., 1997, Nature Biotechnology 15:537).

Some of the antisense polynucleotides consists essentially of, or is, the antisense sequence. Some other antisense polynucleotides of the invention have sequences in addition to the antisense sequence (i.e., in addition to anti-IPM-sense sequence). In this case, the antisense sequence is contained within a polynucleotide of longer sequence.

The antisense nucleic acids (DNA, RNA, modified, analogues) can be made using any suitable method for producing a nucleic acid, such as the chemical synthesis and recombinant methods disclosed herein. Some antisense RNA molecules of the invention are prepared by de novo chemical synthesis or by cloning. For example, an antisense RNA that hybridizes to IPMC mRNA can be made by inserting (ligating) an IPMC DNA sequence (e.g., SEQ. ID No; 1, 3, 5, 8, 10, 12, 14, 16, 18, 20, 23, 25, or 27, or fragment thereof) in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

The antisense oligonucleotides of the invention can be used to inhibit IPMC activity in cell-free extracts, cells, and animals, including mammals and humans. For general methods relating to antisense polynucleotides, see ANTISENSE RNA AND DNA, (1988), D. A. Melton, Ed., Cold Spring Harbor Laboratory, Cold Spring Harbor, N.Y.). See also, Dagle et al., 1991, Nucleic Acids Research, 19:1805. For a review of antisense therapy, see, e.g., Uhlmann et al., Chem. Reviews, 90:543-584 (1990).

2. Triplex Oligo- and Polynucleotides

The present invention provides oligo- and polynucleotides (e.g., DNA, RNA, PNA or the like) that bind to double-stranded or duplex IPMC nucleic acids (e.g., in a folded region of the IPMC RNA or in the IPMC gene), forming a triple helix-containing, or a triplex nucleic acid. Triple helix formation results in inhibition of IPMC expression by, for example, preventing transcription of the IPMC gene, thus reducing or eliminating IPMC activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides of the invention are constructed using the base-pairing rules of triple helix formation (see, e.g., Cheng et al., 1988, J. Biol. Chem. 263: 15110; Ferrin and Camerini-Otero, 1991, Science 354:1494; Ramdas et al., 1989, J. Biol. Chem. 264:17395; Strobel et al., 1991, Science 254:1639; and Rigas et al., 1986, Proc. Natl. Acad. Sci. U.S.A. 83: 9591; each of which is incorporated herein by reference) and the IPMC mRNA and/or gene sequence. Typically, the triplex-forming oligonucleotides of the invention comprise a specific sequence of from about 10 to at least about 25 nucleotides or longer complementary to a specific sequence in the IPMC RNA or gene (i.e., large enough to form a stable triple helix, but small enough, depending on the mode of delivery, to administer in vivo, if desired). In this context, "complementary" means being able to form a stable triple helix. Some of the oligonucleotides are designed to bind specifically to the regulatory regions of the IPMC gene (e.g., the IPMC 5'-flanking sequence, promoters, and enhancers) or to the transcription initiation site, (e.g., between −10 and +10 from the transcription initiation site). For a review of recent therapeutic advances using triplex DNA, see Gee et al., in Huber and Carr, 1994, MOLECULAR AND IMMUNOLOGIC APPROACHES, Futura Publishing Co, Mt Kisco N.Y. and Rininsland et al., 1997, Proc. Natl. Acad. Sci. USA 94:5854, which are both incorporated herein by reference.

3. Ribozymes

The present invention also provides ribozymes useful for inhibition of IPMC activity. The ribozymes of the invention bind and specifically cleave and inactivate IPMC mRNA. Useful ribozymes can comprise 5'- and 3'-terminal sequences complementary to the IPMC mRNA and can be engineered by one of skill on the basis of the IPMC mRNA sequence disclosed herein (see PCT publication WO 93/23572, supra). Ribozymes of the invention include those having characteristics of group I intron ribozymes (Cech, 1995, Biotechnology 13:323) and others of hammerhead ribozymes (Edgington, 1992, Biotechnology 10:256).

Ribozymes of the invention include those having cleavage sites such as GUA, GWU and GUC. Other optimum cleavage sites for ribozyme-mediated inhibition of IPMC activity in accordance with the present invention include those described in PCT publications WO 94/02595 and WO 93/23569, both incorporated herein by reference. Short RNA oligonucleotides between 15 and 20 ribonucleotides in length corresponding to the region of the target IPMC gene containing the cleavage site can be evaluated for secondary structural features that may render the oligonucleotide more desirable. The suitability of cleavage sites can also be evaluated by testing accessibility to hybridization with complementary oligonucleotides using ribonuclease protection assays, or by testing for in vitro ribozyme activity in accordance with standard procedures known in the art.

As described by Hu et al., PCT publication WO 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention.

Some of the ribozymes of the invention are generated in vitro and introduced into a cell or patient. In some cases, gene therapy methods are used for expression of ribozymes in a target cell ex vivo or in vivo.

C. Allelic Variants and Homologs of IPMC polynucleotides

The invention also provides allelic variants of the IPMC polynucleotides of SEQ ID NOs: 1, 3, 5, 7, 8, 10, 12, 14, 16, 18, 20, 22, 23, 25, or 27, and homologs of IPMC. The polynucleotide probes of the invention are used for isolating and expressing IPMC from other organisms, using well known methods, e.g., Sambrook, supra, and Ausubel, supra. For example, a polynucleotide probe comprising all or some of an IPMC cDNA sequence is labeled and used to screen a genomic or cDNA library of an organism by hybridization at moderate stringency (e.g., hybridization in 5×SSC/50% formamide at 42° C. for 16 h, and wash in 0.1×SSC/0.1% SDS at 50 C. for 30 min.). The cDNA library can be oligo-dT or random primed. The cDNA or genomic clones that hybridize with the probe are isolated and analyzed by restriction mapping, Southern hybridization, and DNA sequencing using methods that are well known in the art. Depending on the starting library used, a polynucleotide comprising human or mouse IPMC gene, allelic cDNAs, or IPMC homologs from other species or organisms can be isolated.

Another method for generating IPMC variants having a desired activity is by directed evolution or "gene shuffling," as described, for example in Patten et al., 1997, Curr. Opin. Biotech. 8:724-733; PCT publications WO95/22625; WO97/20078; WO97/35957; WO97/35966; WO98/13487; WO98/13485; PCT 98/00852; PCT 97/24239, and U.S. Pat. No. 5,605,793.

V. Anti-IPMC Antibodies

The present invention provides antibodies that are specifically immunoreactive with human IPMC polypeptide. Accordingly, the invention provides or makes use of antibodies that specifically recognize and bind polypeptides which have an amino acid sequence identical, or substantially identical, to the amino acid sequence of SEQ ID NO: 2, 4, 6, 9, 11, 13, 15, 17, 19, 21, 24, 26, or 28, or an immunogenic fragment thereof. The antibodies of the invention usually exhibit a specific binding affinity for an IPMC polypeptide of at least about $10^7$, $10^8$, $10^9$, or $10^{10}$ M$^{-1}$.

The anti-IPMC antibodies of the invention have a variety of uses, e.g., isolation of IPMC polypeptides (e.g., by immunoaffinity chromatography), detection of IPMC polypeptides, and for inhibition of IPMC activity (e.g., in vivo or in vitro).

A. Production of Anti-IPMC Antibodies

Anti-IPMC antibodies of the present invention can be made by a variety of means well known to those of skill in the art, e.g., as described supra. Antibodies are broadly defined and specifically include fragments, chimeras and the like, that specifically binds an IPMC polypeptide or epitope.

Methods for production of polyclonal or monoclonal antibodies are well known in the art. See, e.g., Coligan, CURRENT PROTOCOLS IN IMMUNOLOGY, Wiley/Greene, New York (1991); Stites et al. (eds.) BASIC AND CLINICAL IMMUNOLOGY (7th ed.) Lange Medical Publications, Los Altos, Calif., and references cited therein ("Stites"); Goding, MONOCLONAL ANTIBODIES: PRINCIPLES AND PRACTICE (2d ed.) Academic Press, New York, N.Y. (1986); Kohler and Milstein, Nature 256: 495-497 (1975) ("Kohler and Milstein"); and Harlow and Lane. These techniques include antibody preparation by selection of antibodies from libraries of recombinant antibodies in phage or similar vectors. See, Huse et al., Science 246:1275-1281 (1989) ("Huse"); and Ward et al., Nature 341:544-546 (1989).

For production of polyclonal antibodies, an appropriate target immune system is selected, typically a mouse or rabbit, but also including goats, sheep, cows, chickens, guinea pigs, monkeys and rats. The immunoglobulins produced by the host can be precipitated, isolated and purified by routine methods, including affinity purification. Substantially monospecific antibody populations can be produced by chromatographic purification of polyclonal sera.

For monoclonal antibodies, appropriate animals will be selected and the desired immunization protocol followed. The antibodies of the invention may be of any isotype, e.g., IgM, IgD, IgG, IgA, and IgE, with IgG, IgA and IgM most referred. Preferred monoclonal anti-IPMC antibodies neutralize (i.e., inhibit or block) one or more biological activities of IPMC. Such antibodies may be obtained by screening hybridoma supernatants for the desired inhibitory activity. Monoclonal antibodies with affinities of $10^8$ liters/mole, preferably $10^9$ to $10^{10}$ or stronger, can be produced by the methods described below. The production of non-human monoclonal antibodies, e.g., murine, lagomorpha, or equine, is well known and can be accomplished by, e.g., immunizing a host animal with a preparation containing IPMC or fragments thereof. Antibody-producing cells obtained from the immunized animals are immortalized and screened, or screened first for the production of antibody which binds to the IPMC polypeptide and then immortalized.

Some anti-IPMC monoclonal antibodies of the present invention are humanized, human or chimeric, in order to reduce their potential antigenicity, without reducing their affinity for their target. Humanized antibodies have been described in the art. See, e.g., Queen, et al., 1989, Proc. Nat'l Acad. Sci. USA 86:10029; U.S. Pat. Nos. 5,563,762; 5,693, 761; 5,585,089 and 5,530,101. The human antibody sequences used for humanization can be the sequences of naturally occurring human antibodies or can be consensus sequences of several human antibodies. See Kettleborough et al., *Protein Engineering* 4:773 (1991); Kolbinger et al., *Protein Engineering* 6:971 (1993).

Humanized monoclonal antibodies against IPMC can also be produced using transgenic animals having elements of a human immune system (see, e.g., U.S. Pat. Nos. 5,569,825; 5,545,806; 5,693,762; 5,693,761; and 5,7124,350).

Useful anti-IPMC binding compositions can also be produced using phage display technology (see, e.g., Dower et al., WO 91/17271 and McCafferty et al., WO 92/01047). In these methods, libraries of phage are produced in which members display different antibodies on their outer surfaces. Antibodies are usually displayed as Fv or Fab fragments. Phage displaying antibodies with a desired specificity are selected by affinity enrichment to an IPMC polypeptide.

Once expressed, the whole antibodies, their dimers, individual light and heavy chains, or other immunoglobulin forms of the present invention can be purified according to standard procedures of the art, including ammonium sulfate precipitation, affinity chromatography, gel electrophoresis and the like (see generally PROTEIN PURIFICATION: PRINCIPLES AND PRACTICE 3RD EDITION (Springer-Verlag, N.Y., 1994)).

An antibody (e.g. an anti-IPMC antibody), is substantially pure when at least about 80%, more often at least about 90%, even more often at least about 95%, most often at least about 99% or more of the polypeptide molecules present in a preparation specifically bind the same antigen (e.g., an IPMC polypeptide). For pharmaceutical uses, anti-IPMC immunoglobulins of at least about 90 to 95% homogeneity are preferred, and 98 to 99% or more homogeneity are most preferred.

B. Modification of IPMC Antibodies

The antibodies of the present invention can be used with or without modification. Frequently, the antibodies will be labeled by joining, either covalently or non-covalently, a substance which provides for a detectable signal. Such labels include those that are well known in the art, e.g., radioactive, fluorescent, or bioactive (e.g., enzymatic) labels. As labeled binding entities, the antibodies of the invention may be particularly useful in diagnostic applications.

Also encompassed by the invention are hybrid antibodies that share the specificity of antibodies against a IPMC polypeptide but are also capable of specific binding to a second moiety. In hybrid antibodies, one heavy and light chain pair is from one antibody and the other pair from an antibody raised against another epitope. This results in the property of multi-functional valency, i.e., ability to bind at least two different epitopes simultaneously. Such hybrids can be formed by fusion of hybridomas producing the respective component antibodies, or by recombinant techniques.

VI. Prognostic and Diagnostic Assays

The present methods provide means for determining if a subject has (diagnostic) or is at risk of developing (prognostic) a disease, condition or disorder that is associated with an aberrant IPMC activity, e.g., an aberrant level of IPMC protein or an aberrant bioactivity, such as results in the development of macular degeneration. The aberrant IPMC activity to be detected include an abnormal level of an IPMC gene or protein, abnormality in an IPMC bioactivity, and the presence of a mutation or particular polymorphic variant in the IPMC gene.

Any cell type or tissue can be utilized in the diagnostics described below. Preferably, a bodily fluid, e.g., blood, is obtained from the subject to determine the presence of a mutation or the identity of the allelic variant of a polymorphic region of an IPMC gene. A bodily fluid, e.g., blood, can be obtained by known techniques (e.g. venipuncture). Alternatively, nucleic acid tests can be performed on dry samples (e.g. hair or skin). For prenatal diagnosis, fetal nucleic acid samples can be obtained from maternal blood as described in WO91/07660. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, e.g., van der Luijt et al. (1994), *Genomics* 20:1-4).

A. Detecting Abnormal Expression or Activity of IPMC

In some methods, abnormal mRNA and/or protein level of IPMC protein are detected by means such as Northern blot analysis, reverse transcription-polymerase chain reaction (RT-PCR), in situ hybridization, immunoprecipitation, Western blot hybridization, or immunohistochemistry. In some methods, cells are obtained from a subject and the IPMC protein or mRNA level is determined and compared to the level of IPMC protein or mRNA level in a healthy subject. An abnormal level of an IPMC polypeptide or mRNA is likely to be indicative of an aberrant IPMC activity.

In some methods, at least one activity of IPMC protein is measured. For example, maintenance of attachment of the RPE to the retina by an IPMC protein can be determined, e.g., as described herein. Comparison of the results obtained with results from similar analysis performed on IPMC proteins from healthy subjects is indicative of whether a subject has an abnormal IPMC activity.

In some methods, the presence of genetic alteration in at least one of the IPMC genes is detected. The genetic alteration to be detected include, e.g., deletion, insertion, substitution of one or more nucleotides, a gross chromosomal rearrangement of an IPMC gene, an alteration in the level of a messenger RNA transcript of an IPMC gene, or inappropriate post-translational modification of an IPMC polypeptide. The genetic alteration can be detected with various methods routinely performed in the art, such as sequence analysis, Southern blot hybridization, restriction enzyme site mapping, and methods involving detection of the absence of nucleotide pairing between the nucleic acid to be analyzed and a probe. In such methods, polynucleotides isolated from a sample from a subject can be amplified first with an amplification procedure such as self sustained sequence replication (Guatelli et al. (1990), *Proc. Natl. Acad. Sci.* USA 87:1874-1878); transcriptional amplification system (Kwoh et al. (1989), *Proc. Natl. Acad. Sci.* USA 86:1173-1177); or Q-Beta Replicase (Lizardi et al. (1988), *Bio/Technology* 6:1197).

In some methods, the alteration in a IPMC gene is detected by mutation detection analysis using chips comprising oligonucleotides ("DNA probe arrays") as described, e.g., in Cronin et al. (1996), *Human Mutation* 7:244. Detection of the alteration can also utilize the probe/primer in a polymerase chain reaction (PCR). See U.S. Pat. No. 4,683, 195; U.S. Pat. No. 4,683,202); Landegran et al. (1988), *Science* 241:1077-1080; and Nakazawa et al. (1994), *Proc. Natl. Acad. Sci.* USA 91:360-364). In some methods, the genetic alteration is detected by direct sequencing using variour sequencing scheme including automated sequencing procedures such as sequencing by mass spectrometry (See, e.g., PCT publication WO 94/16101; Cohen et al. (1996), *Adv. Chromatogr*. 36:127-162; Griffin et al. (1993), *Appl. Biochem. Biotechnol*. 38:147-159).

B. Detecting Single Polynucleotide Polymorphism

Specific diseases or disorders can be associated with specific allelic variants of polymorphic regions of certain genes which do not necessarily encode a mutated protein. Thus, the presence of a specific allelic variant of a polymorphic region of an IPMC gene, such as a single nucleotide polymorphism ("SNP"), in a subject can render the subject susceptible to developing a specific disease or disorder. Polymorphic regions in genes, e.g., IPMC genes, can be identified, by determining the nucleotide sequence of genes in populations of individuals. If a polymorphic region, e.g., SNP is identified, then the link with a specific disease can be determined by studying specific populations of individuals, e.g., individuals which developed a specific disease, such as retinal detachment or macular degeneration.

Many methods have been developed to facilitate the analysis of such single nucleotide polymorphisms. For example, single nucleotide polymorphism can be detected using a specialized exonuclease-resistant nucleotide, as disclosed, e.g., in Mundy, C. R. (U.S. Pat. No. 4,656,127). A Genetic Bit Analysis or GBA™ is described by Goelet (PCT Appln. No. 92/15712). Several primer-guided nucleotide incorporation procedures for assaying polymorphic sites in DNA have been described in Komher et al. (1989), *Nucl. Acids Res*. 17:7779-7784; Sokolov (1990), *Nucl. Acids Res*.18:3671; Syvanen et al. (1990), *Genomics* 8:684-692; Kuppuswamy et al. (1991), *Proc. Natl. Acad. Sci.* USA 88:1143-1147; Prezant et al. (1992), *Hum. Mutat*. 1:159-164; Ugozzoli et al. (1992), *GATA* 9:107-112; Nyren et al. (1993), *Anal. Biochem*. 208:171-175. Other methods for determining the identity of the nucleotide of a polymorphic site have also been described in, e.g., French Patent 2,650, 840; PCT Appln. No. WO91/02087.

C. Detection of IPMC Autoantibodies and Degradation Products

The presence of degradation fragments of IPMC polypeptides or autoantibodies against IPMC polypeptides can also be indicative of the presence of, or a predisposition to the development of, a disease or disorder associated with IPMC bioactivities.

IPMC degradation products can be detected, e.g., examining a sample for the presence of polypeptides that bind to an IPMC antibody using various immunological methods described below, followed by analyzing size and/or structure of the polypeptides. A number of routine techniques can be used to analyze the IPMC polypeptides, e.g., polyacrylamide electrophoresis. Similarly, the presence of autoantibodies against IPMC polypeptides in a biological sample can be detected, e.g., with a IPMC polypeptide antigen using one of the immunological methods described herein.

Methods for detecting an IPMC autoantibody or IPMC degradation fragments in a biological sample can be readily carried out with a number of methods. See generally, E. Maggio, Enzyme-Immunoassay, (1980)(CRC Press, Inc., Boca Raton, Fla.); R. Nakamura et al., Enzyme Immunoassays: Heterogeneous and Homogeneous Systems, In Handbook of Experimental Immunology, Vol. 1, chap. 27 (D. M. Weir ed. 1986)(Blackwell Scientific Publications); and U.S. Pat. Nos. 5,814,461, 5,846,740, 5,993,818, 6,121,004, and 6,225,442. Other methods described in the art for detecting autoantibodies in AMD subjects can also be used in the present invention, e.g., as described in Guerne et al., Ophthalmology, 1991. 98: 602-7; Penfold et al., Clin. Exp. Ophthalmol., 1990. 228: 270-4.

In some methods, purified IPMC polypeptides (or IPMC antibodies) are absorbed onto the solid phase (e.g., a bead, plate or slide as described, e.g., in U.S. Pat. No. 5,801,064), to which is added a biological sample to allow reaction to occur. Bound IPMC autoantibodies (or IPMC degradation fragments) can be detected and quantified with any of the following assays: ELISA (enzyme linked immunoabsorbent assay: with a secondary antibody conjugated to an enzyme), FIA (fluorescent immunosorbent assay: with a secondary antibody conjugated to a fluorescent label), CLIA (chemical linked immunosorbent assay, e.g., utilizing a secondary antibody conjugated to a chemiluminescent label), and RIA (radioimmuno assay; second antibodies labeled with a radio-isotope).

VII. IPMC Therapeutics

IPMC proteins (e.g., IPM 200) can represent a retinal anchor in the IPM adhesive complex. IPMC molecules can also serve as a receptor for growth factors and/or function as a growth factor itself. The present invention provides for both prophylactic and therapeutic methods of treating a subject having a disease or condition associated with abnormal IPMC bioactivity such as retinal detachment or macular degeneration. Subjects at risk for such a disease can be identified by a diagnostic or prognostic assay, e.g., as described herein. Administration of a prophylactic agent can occur prior to the manifestation of symptoms characteristic of the IPMC abnormality, e.g., such that development of the retinal detachment or macular degeneration is prevented or, alternatively, delayed in its progression.

In general, the prophylactic or therapeutic methods comprise administering to the subject an effective amount of a compound which is capable of agonizing a wildtype IPMC activity or antagonizing a mutant (defective) IPMC activity. For example, an IPMC compound can be administered as a prophylactic, e.g., to act as an adhesive in cases of retinal detachment.

A. Screening for IPMC therapeutics

The invention further provides screening methods for identifying IPMC therapeutics, e.g., for treating and/or preventing the development of a disease or condition associated with abnormal IPMC activity such as, e.g., retinal detachment or other macular degeneration-related diseases. An IPMC therapeutic can be any type of compound, including a native or synthetic protein, peptide, peptidomimetic, small molecule, nucleic acid, carbohydrate or lipid. Proteoglycan-associated oligosaccharides, functioning alone or in concert with their core proteins, mediate important biological events, including many that are crucial for the development, growth, function and/or survival of organisms.

The IPMC therapeutics can be identified using various assays depending on the type of compound and activity of the compound that is desired. In some methods, IPMC agonist or antagonist compounds are identified by selecting compounds which are capable of interacting with an IPMC protein or with a molecule capable of interacting with an IPMC protein. In general, a molecule which is capable of interacting with an IPMC protein is referred to as an "IPMC binding partner." In some methods, compounds are screened to identify agents which modulate the amount of IPMC protein produced by a cell.

In cell-free assays, IPMC therapeutics are identified using a reaction mixture containing an IPMC polypeptide and a test compound or a library of test compounds in the presence or absence of a binding partner. A test compound can be, e.g., a derivative of an IPMC binding partner, e.g., a biologically inactive target peptide, or a small molecule. The IPMC polypeptide can be labeled with a specific marker and the test compound or library of test compounds labeled with a different marker. Interaction of a test compound with an IPMC protein or fragment thereof or IPMC binding partner can then be detected by determining the level of the two labels after an incubation step and a washing step. Interaction can also be identified using, e.g., real-time BIA (Biomolecular Interaction Analysis, Pharmacia Biosensor AB) as described, e.g., in BIAtechnology Handbook by Pharmacia. In such methods, detection depends on changes in the mass concentration of macromolecules at the biospecific interface, and does not require any labeling of interactants. In some methods, a library of test compounds can be immobilized on a sensor surface, e.g., which forms one wall of a micro-flow cell. A solution containing the IPMC protein, functional fragment thereof, IPMC analog or IPMC binding partner is then flown continuously over the sensor surface. A change in the resonance angle as shown on a signal recording, indicates that an interaction has occurred.

Cell-free assays can also be used to identify compounds which interact with an IPMC protein and modulate an activity of an IPMC protein. For example, an IPMC polypeptide is contacted with a test compound and the catalytic activity of IPMC protein is monitored. In one embodiment, the ability of the IPMC protein to bind a target molecule is determined. The binding affinity of the IPMC protein to a target molecule can be determined according to methods known in the art, e.g., as described in Holmquist et al. (1979) *Anal. Biochem.* 95:540; and U.S. Pat. No. 5,259,045.

In cell based assays, a cell which is capable of producing IPMC protein is incubated with a test compound and the amount of IPMC polypeptide produced in the cell medium is measured and compared to that produced from a cell which has not been contacted with the test compound. For example, cells transfected with a reporter gene operably linked to an IPMC promoter, such as IPM 150 or IPM 200 promoter (as shown in SEQ ID NO: 7 or 22), can be used. The reporter gene can encode, e.g., a gene product that gives rise to a detectable signal or marker such as color change or fluorescence (e.g., chloramphenicol acetyl transferase, luciferase, β-galactosidase and alkaline phosphatase). The cells are then contacted with a test compound and determining the level of expression of the reporter gene. The specificity of the compound on the level of expression can be confirmed by various control analysis, e.g., measuring the expression of one or more control promoters. Compounds that can be tested with these methods include small molecules, proteins, and nucleic acids. In particular, this assay can be used to determine the efficacy of IPMC antisense molecules or ribozymes.

B. IPMC Polynucleotide Therapeutics and Gene Therapy

The therapeutic methods of the invention involve the administration of an IPMC polynucleotide that finctions to inhibit or stimulate IPMC activity under in vivo physiological conditions, and is relatively stable under those conditions for a period of time sufficient for a therapeutic effect. As noted above, modified nucleic acids can be useful in imparting such stability, as well as for targeting delivery of the oligonucleotide to the desired tissue, organ, or cell.

Oligo- and poly-nucleotides can be delivered directly as a drug in a suitable pharmaceutical formulation, or indirectly by means of introducing a nucleic acid into a cell, including liposomes, immunoliposomes, ballistics, direct uptake into cells, and the like as described herein. For treatment of disease, the oligonucleotides of the invention will be administered to a patient in a therapeutically effective amount. A therapeutically effective amount is an amount sufficient to ameliorate the symptoms of the disease or modulate IPMC activity in the target cell, e.g., as can be measured using a using a cell based assay, e.g., as described in §III(A), supra. Methods useful for delivery of oligonucleotides for therapeutic purposes are described in U.S. Pat. No. 5,272,065, incorporated herein by reference. Other details of administration of pharmaceutically active compounds are provided below. In another embodiment, oligo- and poly-nucleotides can be delivered using gene therapy and recombinant DNA expression plasmids of the invention. It will be recognized to those of skill that, to administer antibodies or therapeutic oligonucleotides to the brain, it is sometime necessary administer via intracerebroventricular injections or other direct administration mode.

In some methods, a gene delivery system for an IPMC polynucleotide therapeutic can be introduced into a patient by any of a number of methods. For example, the gene delivery vehicle can be introduced by catheter (See U.S. Pat. No. 5,328,470) or by stereotactic injection (Chen et al. (1994), *Proc. Natl. Acad. Sci.* USA 91:3054-3057. An IPMC gene or cDNA, such as any one of the sequences represented in the group consisting of SEQ ID NOs: 1, 3, 5, 7, 8, 10, 12, 14, 16, 18, 20, 22, 23, 25, and 27, or a sequence homologous thereto can be delivered in a gene therapy construct by electroporation using techniques described. Dev. et al. (1994), *Cancer Treat. Rev.* 20:105-115. Gene therapy refers to the introduction of an otherwise exogenous polynucleotide which produces a medically useful phenotypic effect upon the (typically) mammalian cell(s) into which it is transferred.

In some methods, gene therapy involves introducing into a cell a vector that expresses an IPMC gene product (such as an IPMC polypeptide substantially similar to the IPMC polypeptide having a sequence of SEQUENCE ID NO: 2, 4, 6, 17, 19, 21, or 27 to increase IPMC activity, or an inhibitory IPMC polypeptide to reduce activity), expresses a nucleic acid having an IPMC gene or mRNA sequence (such as an antisense RNA, e.g., to reduce IPMC activity), expresses a polypeptide or polynucleotide that otherwise affects expression of IPMC gene products (e.g., a ribozyme directed to IPMC mRNA to reduce IPMC activity), or replaces or disrupts an endogenous IPMC sequence (e.g., gene replacement and gene knockout, respectively). Numerous other embodiments will be evident to one of skill upon review of the disclosure herein.

Vectors useful in IPMC gene therapy can be viral or nonviral, and include those described supra in relation to the IPMC expression systems of the invention. It will be understood by those of skill in the art that gene therapy vectors may comprise promoters and other regulatory or processing sequences, such as are described in this disclosure. Usually the vector will comprise a promoter and, optionally, an enhancer (separate from any contained within the promoter sequences) that serve to drive transcription of an oligoribonucleotide, as well as other regulatory elements that provide for episomal maintenance or chromosomal integration and for high-level transcription, if desired. A plasmid useful for gene therapy can comprise other functional elements, such as selectable markers, identification regions, and other sequences. The additional sequences can have roles in conferring stability both outside and within a cell, targeting delivery of IPMC nucleotide sequences (sense or antisense) to a specified organ, tissue, or cell population, mediating entry into a cell, mediating entry into the nucleus of a cell and/or mediating integration within nuclear DNA. For example, aptamer-like DNA structures, or other protein binding moieties sites can be used to mediate binding of a vector to cell surface receptors or to serum proteins that bind to a receptor thereby increasing the efficiency of DNA transfer into the cell. Other DNA sites and structures can directly or indirectly bind to receptors in the nuclear membrane or to other proteins that go into the nucleus, thereby facilitating nuclear uptake of a vector. Other DNA sequences can directly or indirectly affect the efficiency of integration.

Suitable gene therapy vectors may, or may not, have an origin of replication. For example, it is useful to include an origin of replication in a vector for propagation of the vector prior to administration to a patient. However, the origin of replication can often be removed before administration if the vector is designed to integrate into host chromosomal DNA or bind to host mRNA or DNA.

As noted, the present invention also provides methods and reagents for gene replacement therapy (i.e., replacement by homologous recombination of an endogenous IPMC gene with a recombinant gene). Vectors specifically designed for integration by homologous recombination may be used. Important factors for optimizing homologous recombination include the degree of sequence identity and length of homology to chromosomal sequences. The specific sequence mediating homologous recombination is also important, because integration occurs much more easily in transcriptionally active DNA. Methods and materials for constructing homologous targeting constructs are described by e.g., Mansour et al., 1988, Nature 336: 348; Bradley et al., 1992, Bio/Technology 10: 534. See also, U.S. Pat. Nos. 5,627,059; 5,487,992; 5,631,153; and 5,464,764. In one embodiment, gene replacement therapy involves altering or replacing all or a portion of the regulatory sequences controlling expression of the IPMC gene that is to be regulated. For example, the IPMC promoter sequences (e.g., such as are found in SEQUENCE ID NO: 6) may be disrupted (to decrease IPMC expression or to abolish a transcriptional control site) or an exogenous promoter (e.g., to increase IPMC expression) substituted.

The invention also provides methods and reagents for IPMC gene knockout (i.e., deletion or disruption by homologous recombination of an endogenous IPMC gene using a recombinantly produced vector). In gene knockout, the targeted sequences can be regulatory sequences (e.g., the IPMC promoter), or RNA or protein coding sequences. The use of homologous recombination to alter expression of endogenous genes is described in detail in U.S. Pat. No. 5,272,071 (and the U.S. Patents cited supra), WO 91/09955, WO 93/09222, WO 96/29411, WO 95/31560, and WO 91/12650. See also, Moynahan et al., 1996, Hum. Mol. Genet. 5:875.

Gene therapy vectors can be introduced into cells or tissues in vivo, in vitro or ex vivo. For ex vivo therapy, vectors may be introduced into cells, e.g., stem cells, taken from the patient and clonally propagated for autologous transplant back into the same patient (see, e.g., U.S. Pat. Nos. 5,399,493 and 5,437,994, the disclosures of which are herein incorporated by reference).

C. Formulation and Dosages

The IPMC therapeutics of the present invention (e.g., IPMC polypeptides or fragments thereof, sense and antisense IPMC polynucleotides, anti-IPMC antibodies or binding fragments thereof, and antagonists or agonists (e.g. small molecule modulators) can be directly administered under sterile conditions to the host to be treated. For example, methods useful for delivery of oligonucleotides for therapeutic purposes are described in the art, e.g., in U.S. Pat. No. 5,272,065. However, while it is possible for the active ingredient to be administered alone, it is often preferable to present it as a pharmaceutical formulation. Formulations typically comprise at least one active ingredient together with one or more acceptable carriers thereof. Each carrier should be both pharmaceutically and physiologically acceptable in the sense of being compatible with the other ingredients and not injurious to the subject. For example, the bioactive agent can be complexed with carrier proteins such as ovalbumin or serum albumin prior to their administration in order to enhance stability or pharmacological properties such as half-life.

Pharmaceutical compositions for use in accordance with the present invention can be formulated in a conventional manner using one or more physiologically acceptable carriers or excipients. They can be prepared by any methods well known in the art of pharmacy. See, e.g., Gilman et al (eds.) (1990) Goodman and Gilman's: The Pharmacological Bases of Therapeutics (8th ed.) Pergamon Press; and (1990) Remington's Pharmaceutical Sciences (17th ed.) Mack Publishing Co., Easton, Pa.; Avis et al (eds.) (1993) Pharmaceutical Dosage Forms: Parenteral Medications Dekker, N.Y.; Lieberman et al. (eds.) (1990) Pharmaceutical Dosage Forms: Tablets Dekker, N.Y.; and Lieberman et al (eds.) (1990) Pharmaceutical Dosage Forms: Disperse Systems Dekker, N.Y.

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

Thus, the compounds and their physiologically acceptable salts and solvates can be formulated for administration by, for example, eye drops, injection, inhalation or insufflation (either through the mouth or the nose) or oral, buccal, parenteral or rectal administration.

A preferred method of administration is an eye drop. Preferred methods of administration also include choroidal injection, transscleral injection or placing a scleral patch, and selective arterial catheterization. Other preferred deliveries are intraocular, including transretinal, subconjunctival bulbar, scleral pocket and scleral cutdown injections. The agent can be alternatively administered intravascularly, such as intravenously (IV) or intraarterially.

The IPMC therapeutics can be administered alone or in combination with other molecules known to have a beneficial effect on retinal attachment or damaged retinal tissue, including molecules capable of tissue repair and regeneration and/or inhibiting inflammation. Examples of useful cofactors include basic fibroblast growth factor (bFGF), ciliary neurotrophic factor (CNTF), axokine (a mutein of CNTF), leukemia inhibitory factor (LIF), neutrotrophin 3 (NT-3), neurotrophin-4 (NT-4), nerve growth factor (NGF), insulin-like growth factor II (LaVail et al. (1998), *Invest. Ophthalmol. Vis. Sci.* 39:592-602), prostaglandin E2 (LaVail et al. (1998), *Invest. Ophthalmol. Vis. Sci.* 39:581-591), 30 kD survival factor, taurine, and vitamin A.

VIII. Kits

The invention further provides kits for use in diagnostics or prognostic methods for diseases or conditions associated with abnormal IPMC activity, such as retinal detachment, chorioretinal degeneration, retinal degeneration or macular degeneration or for determining which IPMC therapeutic should be administered to a subject, for example, by detecting the presence of IPMC mRNA or protein in a biological sample. The kit can detect abnormal levels or an abnormal activity of IPMC protein, RNA or a degradation product of an IPMC protein or RNA. Some of the kit detect autoantibodies against an IPMC polypeptide.

The kits can contain at least one probe nucleic acid, primer set; and/or antibody reagent. For example, some kits contain a labeled compound or agent capable of detecting IPMC protein or mRNA in a biological sample; means for determining the amount of IPMC protein in the sample; and means for comparing the amount of IPMC protein in the sample with a standard. The compound or agent can be packaged in a suitable container. The kit can further comprise instructions for using the kit to detect IPMC mRNA or protein.

Some kits contain one or more nucleic acid probes capable of hybridizing specifically to at least a portion of an IPMC gene or allelic variant thereof, or mutated form thereof. Preferably the kit comprises at least one oligonucleotide primer capable of differentiating between a normal IPMC gene and an IPMC gene with one or more nucleotide differences.

\*\*\*

The practice of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature. Molecular Cloning A Laboratory Manual (1989), 2nd Ed., ed. by Sambrook, Fritsch and Maniatis, eds., Cold Spring Harbor Laboratory Press; Hogan et al. (Manipulating the Mouse Embryo: A Laboratory Manual (1986), Cold Spring Harbor Laboratory Press; Current Protocols in Molecular Biology, Ausubel et al., John Wiley & Sons, N.Y., 1992; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

Many modifications and variations of this invention can be made without departing from its spirit and scope. The specific examples described herein are for illustration only and are not intended to limit the invention in any way.

All publications, figures, patents and patent applications cited herein are hereby expressly incorporated by reference for all purposes to the same extent as if each was so individually denoted.

EXAMPLES

Example 1

Characterization of IPM 150 and IPM 200 Sequences

The present inventors have identified the nucleotide and amino acid sequences of IPM 150 and IPM 200 molecules in various species, as shown in the attached sequence listing. Characterization of these molecules has been performed in part as described below. Unless otherwise indicated, IPM 150 molecule discussed in the Examples relates to the human IPM 150 isoform A variant that is encoded by the cDNA and amino acid sequences shown respectively in SEQ ID NOs: 27 and 28.

a. Tissues: Human eyes were obtained from MidAmerica Transplant Services (St. Louis, Mo.) and the University of Iowa Lion's Eye Bank (Iowa City, Iowa) and processed within three hours of cardiac cessation under approved Institutional Review Board protocols. Human eyes were obtained from donors less than 60 years of age and without any known ocular disorder. Monkey eyes and other organs were obtained from cynomolgus macaque monkeys (*Macaca fascicularis*) immediately after barbiturate-induced euthanasia. All animals were treated in conformity with the NIH "Guide for the Care and Use of Laboratory Animals", the ARVO "Resolution for the Use of Animals in Research" and the established guidelines of St. Louis University and the University of Iowa.

b. Isolation of IPM: Human and monkey neural retinas were separated from the RPE and incubated in 10 mM phosphate buffered saline (PBS), pH 7.4, containing a cocktail of protease inhibitors (2 mM phenylmethylsulfonylfluoride, 10 mM N-ethylmaleimide, 1 μg/ml pepstatin A, 1 μg/ml leupeptin, 0.02% sodium azide, 100 KIU/ml aprotinin, 100 mM 6-amino-n-caproic acid, 5 mM benzamidine-HCl and 0.04% EDTA) for 5-10 min, with slight agitation, to remove soluble IPM constituents (15). The isolated retinas were then placed in (1) 4 M urea in 10 mM PBS containing 0.5% NP-40 and protease inhibitors or (2) distilled water for 7-10 minutes at 4° C., with slight agitation, until the IPMC protein dissociated from the photoreceptor cells. The resulting sheets of insoluble IPMC proteins were isolated, dialyzed against 10 mM PBS pH 7.4, their protein content determined using a micro BCA assay (Pierce), pelleted by centrifugation and frozen at 80° C., or lyophilized for subsequent analyses. Alternatively, pellets were resuspended in PBS and repelleted 7-10 times.

c. Identification of IPM 150 and IPM 200 Proteins: Aqueous-insoluble human and monkey IPMC protein preparations were homogenized and digested with protease-free chondroitin ABC lyase (E.C. 4.2.2.4) (Seikagaku Ltd., Rockville, Md.) at a concentration of 2 U/ml, in the presence of protease inhibitors, for 2 hrs. at 37° C. Western blot analyses of chondroitinase-treated IPMC preparations from pig, monkey and human retinas demonstrated bands of approximately 150 kDa and 200 kDa (and minor bands of 180 kDa and 220 kDa in pig and monkey, respectively) that were labeled by AC6S antibody and PNA. The 150 kDa bond was designated IPM 150, and the 200 kDa band was designated IPM 200. The 150 kDa band appears to contain two glycoproteins; one that binds PNA and migrates to a lower molecular weight following exposure to neuraminidase and O-glycanase, and a second neuraminidase-insensitive component that binds PHA-L. Following complete deglycosylation, AC6S binds to a band of approximately 55-58 kDa. These studies indicate that at least two distinct chondroitin 6-sulfate-containing proteoglycans are associated with CMSs.

Proteins were separated on one- or two-dimensional SDS-polyacrylamide gels under denaturing conditions, transferred to sequencing grade PVDF membranes (Immobilon P, Millipore Corp., Bedford, Mass.) and briefly stained with 0.1% Coomassie blue. IPM 150 bands were identified by comparison to adjacent blot strips and incubated with PNA or AC6S antibody. To identify bands of interest, some lanes were blocked in 50 mM Tris buffer, pH 7.4, containing 1 mM $MgCl_2$, 1 mM $CaCl_2$ (TMC) and 0.2% Tween 20, with or without 2% BSA for 45 minutes, and subsequently rinsed in TMC. The blot strips were exposed to HRP-conjugated lectins or antibodies (followed by HRP-conjugated secondary antibodies) diluted in TMC (1/50-1/500), for one hour, and rinsed in TMC and the HRP-conjugated probes visualized using 4-chloro-1-naphthol and hydrogen peroxide. Some blot strips can also be stained for total protein using India ink (1 µl/ml) in TMC with 0.2% Tween 20. Identified bands, especially IPM 150 and IPM 200 were used for direct amino acid sequencing or eluted in the presence of CNBr.

For direct amino acid sequence, bands containing IPM 150 protein and IPM 200 protein were excised and the proteoglycans eluted in 25 mM Tris containing 192 mM glycine and 0.1% SDS using a BioRad electro-eluter. The $NH_2$-terminal amino acid sequence for IPM 150 was determined by Edman degradation. Sequence for every region was obtained at least twice.

Two strategies for generating and isolating CNBR peptides from SDS-PAGE-purified IPM 150 and IPM 200 proteins can be utilized. A blotting procedure allows one to easily remove SDS from PVDF and allows for reliable elution of PVDF-blotted proteins in high yield. As an alternative approach or when tryptic peptides are required, an "in-gel" digestion procedure was used to generate IPM 150 and IPM 200 peptides.

CNBr Peptides from Blotted Proteins. PVDF blots were washed with HPLC grade water and stained with 0.05% Coomassie blue in 50% methanol for five minutes. Individual protein bands were cut into 1×2 mm pieces and submerged in 500 µl of ice-cold 95% acetone for one hour. The supernatant was removed and the PVDF-bound protein washed with another 500 µl of acetone. The membrane was air-dried, submerged in 100 µl of 70% formic acid, and 10 µl of 70 mg/ml CNBR per 10 µg of blotted protein added. Blots were incubated in the dark for 24 hours, at room temperature, the supernatant removed, the membranes dried, and 100 µl of 40% acetonitrile added to the membranes. Following incubation at 37° C., for 3 hours, the supernatant was removed and pooled with the previous supernatant. Finally, the PVDF pieces were extracted again at 50° C. with 100 µl of 0.05% TFA in 40% acetonitrile, the supernatant combined with the two prior extracts, and collectively dried under vacuum. Chromatographically isolated IPM 150 and IPM 200 were digested by redissolving dried samples in 70% formic acid (v/v) and adding a 20- to 100-fold molar excess (over the methionyl residues) of CNBR, for 24 hours. The reaction was stopped by drying the sample under vacuum.

CNBr Peptides From "In-gel" Tryptic Digestion: Other amino acid sequences were obtained from fragments of IPM 150 generated by an "in-gel" trypsin digestion protocol. Briefly, chondroitinase ABC-treated IPMC protein preparations were separated by SDS-PAGE, the gels were stained with 0.1% Coomassie and IPM 150 was identified and excised. Gel strips were incubated, at 37° C., for 24 hours, in a 1:25 (weight-to-weight) ratio of trypsin (Boehringer Mannheim, Indianapolis, Ind.) to protein. Following incubation, the gel pieces were shaken at room temperature for 8 hours to extract peptides. The resulting fragments were fractionated using reverse phase HPLC in 0.2 ml of a 2 M urea solution. Separated peptides were detected by absorbance at 210 nm and collected using a peak detector. Selected peptides were subjected to amino acid sequencing at the W. K. Keck Foundation (New Haven, Conn.).

Alternatively, IPM 150, IPM 200, and homolog proteoglycans of the invention can be selectively isolated from other insoluble IPMC glycoproteins based on their high concentration of carboxyl and sulfate ester groups and high negative charge. Insoluble IPMC protein preparations are dialyzed against 8 M urea in 50 mM Tris-HCl, pH 6.8, and subsequently applied to a HPLC TSK DEAE-5PW analytical ion exchange column. Bound proteoglycans are eluted by a linear salt gradient of 0.15-1.0 M sodium chloride. IPM 150 and IPM 200 elute between 0.4-0.5 M sodium chloride. IPM 150- and IPM 200-containing fractions are pooled, dialyzed against distilled water, and lyophilized. Lyophilized samples are chondroitinase ABC-treated and separated by HPLC size exclusion chromatography on a TSK 4000PW-3000PW column in the presence of 4 M guanidine hydrochloride in 10 mM Tris-HCl, pH 7.0, containing protease inhibitors. The two peaks containing IPM 150 and IPM 200 are collected and the presence of IPM 150 and IPM 200 in the fractions verified by Western blot analysis. These fractions can be utilized for analysis of core proteins and carbohydrates of IPM 150 and IPM 200 and homologs, allelic variant and mutants thereof. Other fractions can be saved for analyses of additional IPMC protein constituents.

The predicted molecular weight of the "native" IPM 150 core protein, as deduced from its cDNA sequence, is about 77.8 kDa. The protein migrates at approximately 150 kDa on SDS-PAGE gels under denaturing conditions following digestion of native IPM with chondroitinase ABC. The discrepancy between the calculated and the observed molecular weights of IPM 150 is most likely due to the presence of N and/or O-glycosidically linked oligosaccharides that remain attached to the protein after chondroitinase treatment. This contention is supported by biochemical analyses demonstrating that IPM 150 migrates at 80 kDa and 105 kDa following enzymatic or chemical deglycosylation, respectively.

As an initial step in determining whether the difference in molecular weights of IPM 150 and IPM 200 is manifested by differences in their protein and/or their oligosaccharide compositions, CNBR and/or tryptic peptides derived from human IPM 150 and IPM 200 can be separated and the resultant profiles from the two proteoglycans compared for consistent differences in the numbers or sizes of resultant peptides. The resulting peptides are separated on a Vydac C-18 reverse phase HPLC column equilibrated in 0.05% TFA and 1.6% acetonitrile, and eluted with increasing concentrations of the same buffer. Peptides are collected by peak with the use of an ISCO peak detector. Samples are stored at 5° C. or applied directly onto polybrene coated GF-C filters and their amino acid sequences determined. This procedure provides "CNBR peptide maps" of IPM 150 and IPM 200. Differences in numbers of peptides might indicate variation in amino acid sequence, since CNBR cleaves at unoxidized methionine residues. Overall differences in apparent sizes of peptides indicate either a true difference in amino acid composition or the presence of glycanated variants of the same peptide.

The N-termini of CNBR- and/or tryptic-derived peptides can be subjected to amino acid sequencing using an Applied Biosystems sequencer equipped with on-line HPLC systems. Approximately 0.05-1.0 nm of protein/peptide is sufficient to sequence between 15 and 40 residues, respectively. Amino acid sequences obtained in this fashion are verified by sequencing the same peptide at least twice. Since greater than 80% of eukaryotic proteins have blocked amino termini that preclude direct amino acid sequencing, this strategy provides information pertaining to partial amino acid sequences of IPMC core proteins that might be unattainable otherwise. Results obtained from these analyses provide information about differences in amino acid sequences of IPMC core proteins in humans; similar analyses can be performed using monkey and pig IPMC protein if their CNBR profiles differ significantly from those observed in humans.

Direct amino-terminal amino acid sequencing resolved 31 and 20 amino acids of the amino termini of monkey and human IPM 150, respectively. Alignment of these two sequences reveals a high degree of sequence conservation between the two species. Comparison of these sequences to those in the NCBI database indicates that IPM 150 is not homologous to other proteins.

N-terminal amino acid sequences of eight core proteins from human, monkey and pig IPMC protein were determined. The sequences show that (1) the core proteins of the IPM 150, and IPM 200 proteins share a strongly conserved N-terminus; (2) that these proteins are conserved among higher mammalian species; and (3) that the amino acid sequences are unique. Specific conservative amino acid substitutions were observed, however, at both the intra- and inter-species levels.

d. Reverse Transcription-Polymerase Chain Reaction (RT-PCR): Total retinal RNA was isolated from monkey and human retinas using RNAStat-60 reagent (Tel-Test, Inc., Friendswood, Tex.) and 100 ng/tube were reverse-transcribed using random hexamer primers and the GeneAmp® RNA PCR Kit (Perkin Elmer Cetus, Foster City, Calif.). For the initial experiments, monkey retinal cDNA was PCR amplified. During the synthesis of these primers, inosine residues were used in positions of complete degeneracy. In the first step, 200 ng/tube total RNA is reverse transcribed with M-MLV reverse transcriptase using random hexamers or oligo (dT) primers for 5 minutes at room temperature, followed by incubation at 42° C. for 15 minutes. The enzyme is then denatured by heating at 95° C. for 15 minutes. cDNA is amplified at annealing temperatures 2° C. below the melting point of the primers or, in the case of degenerate primers, 2° C. below the lowest melting point possible for that primer, for 30 cycles. Ten percent of the reaction is analyzed by agarose gel electrophoresis. If no amplification product is observed, a small aliquot of the reaction is used as template in a second amplification reaction. If an amplification product is present, the experiment is repeated, at least twice, from a new stock of RNA; only those amplification products which occur consistently are used for subcloning. Following amplification, 10% of the reaction is analyzed by agarose gel electrophoresis. When an amplification product is obtained, the experiment is repeated, at least twice, from a new stock of RNA. A monkey amplification product of 580 bp was isolated and ligated into the SrfI site of the vector PCR-Script SK (Stratagene, La Jolla, Calif.). The resulting clone, designated 70-1, was sequenced and shown to encode 192 amino acids of monkey IPM 150, starting at the presumed amino terminus. The deduced amino acid sequence features two possible N-glycosylation sites, numerous potential glycosylation sites, four cysteine residues, and two hyaluronate-binding motifs.

Another clone, designated 9-5#3, was generated by RT-PCR. Human retinal RNA was reverse transcribed, using a primer complementary to nucleotides 2927 to 2943 of the human IPM 150 sequence. The resulting single-stranded cDNA was amplified by PCR. The resulting PCR fragment was ligated into the vector PCRII (InVitrogen, Carlsbad, Calif.) and subcloned according to standard art known methods.

e. cDNA Libraries. Five cDNA libraries, derived from poly $A^{(+)}$ RNA isolated from human and pig ocular tissues, were generated. They are: human retina—$1.6 \times 10^6$ independent clones (random primed; λgt11); pig retina—$0.5 \times 10^6$ independent clones (random- and oligo (dT)-primed; λgt11); and pig retina/RPE/choroid—$5.0 \times 10^6$ independent clones (random- and oligo (dT)-primed; λZapII).

Construction of λZapII phagemid libraries is performed as follows: Double-stranded cDNA with cohesive EcoR I ends are synthesized using the SuperScript™ Choice System (Gibco BRL). mRNA is reverse transcribed in a reaction primed by oligo(dT) and/or random hexamers catalyzed by SuperScript™ II out in the same tube to increase the yield of double-stranded cDNA. EcoR I adaptors are added without having to methylate or restriction enzyme digest the cDNA. The cDNA is made vector-ready by passage over a column that removes unincorporated adapter-arms (Pharmacia). The mixture is packaged with Gigapack packing extract (Stratagene) and transfected into E.coli XL-1 Blue cells (Stratagene). The number of independent clones is assessed prior to the screening of each library.

f. Screening cDNA Libraries with DNA Probes. Human and monkey cDNA libraries in λZapII are plated to a density of approximately 3000 pfu per 100 mm plate on E.coli XL-1 Blue host cells. Duplicate plaque lifts are prepared using Hybond N nylon filters (Amersham). cDNA probes are $^{32}$P-labeled in a random-primed reaction using a multi-primer DNA labeling kit (Amersham), purified over G-50 columns, heat denatured and added to the prehybridization mix. Hybridization can be performed for 8-20 hours at 65° C. After hybridization the filters are washed at room temperature for 3×5 minutes in 2X SSC containing 0.3% SDS and then 2×3 minutes in 0.2×SSC containing 0.3% SDS. Final wash stringencies can be decreased or increased depending on the source and sequence of the cDNA probe and level of background radiation detected on the autoradiograms. Autoradiograms are aligned with the filters and plates. Only plaques giving a signal on both filters are isolated, replated at a lower density (~500pfu/plate) and rescreened until well-isolated positive plaques are obtained. Lambda gt11 libraries are screened in a similar fashion, with the exception that E.coli Y1090 are used in place of XL-1 Blue cells as host.

g. Isolation and analysis of human IPM 150 cDNA sequence

A commercially available human retinal cDNA library in λgt11 (Clontech Laboratories Inc., Palo Alto, Calif.) was screened by plaque hybridization, using probes derived from clone 70-1. Plaques were plated to a density of approximately 10,000 pfu per 150 mm Petri dish on E. coli Y1090 host cells. Duplicate plaque lifts were prepared using nitrocellulose filters (Schleicher & Schuell, Keene, N.H.). cDNA probes were labeled with $^{32}$PdCTP in a random-primed reaction and hybridized to the plaques for 12-20 hrs at 65° C. After hybridization, the filters were washed at room temperature for 10 min in 2×SSC (0.3 M NaCl and 30 mM sodium citrate) containing 0.3% SDS, and two additional times, for 10 min each time in 0.2×SSC containing 0.1% SDS at 60° C. Plaques giving signals on autoradiograms derived from both filters were isolated, eluted in λ-buffer (10 mM Tris, pH 7.5 and 10 mM MgCl), replated at a lower density (~500 pfu/plate), and rescreened until isolated, positive plaques were obtained. cDNA inserts of purified λgt11 clones were PCR-amplified using primers to the flanking regions of λgt11 and ligated into pCRII using the TA cloning kit (InVitrogen, Carlsbad, Calif.).

Three cDNA clones, designated 8.1.2, 11.1.1 and 12.3.1, were isolated, sequenced and assembled into one contiguous sequence. The assembled nucleotide sequence of 3,261 bp (SEQ ID NO: 27) contains an uninterrupted open reading frame of 2,313 bp and several hundred bp of untranslated 5' and 3' regions. Verification that the assembled sequence encodes human IPM 150 is provided by the presence of the complete amino-terminal amino acid sequence, as well as all internal peptides, within the deduced amino acid sequence.

Clone 8.1.2 lacks a 234 bp segment within its 5' region that encodes the amino terminus of IPM 150. This clone can represent a cloning artifact or it can indicate the existence of IPM 150 isoforms. PCR product encompassing the entire open reading frame of IPM 150 was cloned. PCR amplification of reverse-transcribed human retinal RNA yields a 2579 bp fragment which has been subcloned and designated 9p#3. This clone is completely homologous to the assembled sequence and includes the 234 bp region that is absent in clone 8.1.2.

Clone 12.3.1 encodes a 809 bp fragment of human IPM 150, comprising 280 bp of the 5'UTR and 589 nucleotides of the coding region, and shares 94% homology to the 5' region of the monkey homolog between nucleotides 73 and 256 (human) and 2 and 185 (monkey), using BESTFIT analysis with a gap weight of 12 and a length weight of 4. Clone 12.3.1 appears to display the same features/motifs as p70-1 with the exception that an additional N-glycosylation site is present and a potential hyaluoronan-binding motif occurs in the leader sequence.

NCBI Database searches of the compiled nucleotide and amino acid sequences show that they are novel. A few expressed sequence tags (ESTs), derived from human retina, vein endothelial cells, and brain, however, share homology with IPM 150 (GenBank Accession numbers H38604, W26960, H38594, AA326863 and AA296278). Translation of the open reading frame of the assembled cDNA sequences encodes a protein of 771 amino acids with an isoelectric point of 4.70 and a predicted molecular weight of 86.36 kDa. The protein is generally hydrophilic (Kyte and Doolittle (1982), *J. Mol. Biol.* 157:105-132) except for the first 18 amino acids which form a hydrophobic region flanked by charged amino acid residues; this region can represent a signal sequence.

A distinct distribution of consensus sequence sites for N- and O-linked glycosylation are present in IPM 150. There are several consensus sequences for N-linked glycosylation (Komfeld and Kornfeld (1985), *Ann. Rev. Of Biochem.* 54:631-664) sequestered in the amino-terminal (amino acids 71 to 217 (SEQ ID NO: 28) and the carboxy-terminal (beginning at amino acid 591 (SEQ ID NO: 28) portions of the IPM 150 core protein. In contrast, the central domain of IPM 150 (between amino acids 220 and 565 (SEQ ID NO: 28) features 17 sites which are suitable for O-linked glycosylation, as predicted by a proposed algorithm for the activity of polypeptide N-acetylgalactosaminyl-transferase. Hansen et al. (1995), *Biochem. J.* 308:801-813. There is almost no overlap between the regions containing potential O- and N-linked glycosylation sites. Hyaluronan binding consensus sequences (Yang et al. (1994), *EMBO J.* 13:286-296) and several cysteine residues are also present in the amino- and carboxy-terminal regions of the core protein. The distribution of the carboxy-terminal cysteine residues closely resembles that of EGF-like domains (Rees et al, (1988), *EMBO J.* 7:2053-2061), motifs that are present in many extracellular matrix proteins. Consensus sequences for other domains that are commonly associated with extracellular matrix proteins, including immunoglobulin-like (Williams and Barclay (1988), *Ann. Rev. Immun.* 6:381-405) and lectin-like domains (Krusius et al. (1987), *J. Biol. Chem.* 262:13120-13125), are not present in IPM 150.

h. Subcloning cDNA Inserts. Positive plaques are picked and resuspended in 0.5 ml SM (0.1 M NaCl, 1 mM MgSO$_4$, 5 mM Tris, pH 7.5, and 2% gelatin). Inserts in λZapII phagemids are subcloned by in vivo excision as described by the manufacturer (Strategine). The resulting pBluescript SK(-) plasmids are transferred into *E.coli* XL-1 Blue. Inserts contained within λgt11 are isolated using the Wizard Lambda Prep kit (Promega), released by EcoR1 digestion and subsequently ligated into pBluescript. Plasmid DNA is isolated using Wizard miniprep resins (Promega) and assayed for insert size by restriction enzyme digest and size fractionation on 0.7-1.5% agarose gels.

i. Anchored PCR. cDNA amplification using one-sided, or "anchored," PCR can be used to obtain missing sequence information. Regions upstream (5') or downstream (3') of known sequence can be amplified by this method. To amplify unknown sequences downstream, anchored PCR is performed using 100-300 ng total poly (A)$^+$ retinal RNA and these primers: an oligo (dT) primer and two sequence-specific primers, one of the original amplification reaction (primer 1) and the second (primer 2; an internal sequence-specific primer, which can partially overlap primer 1) for the reamplification reaction. The mRNA is reverse-transcribed as described above, with an oligo (dT) primer. The resulting cDNA is amplified using oligo (dT) and sequence-specific primer 2. Analysis of an aliquot of the first amplification reaction by agarose gel electrophoresis should reveal a smear, whereas analysis of the reamplification reaction should appear as a single band which are subcloned into a plasmid vector, pCRII, using a TA cloning kit version 2.2 (Invitrogen) and sequenced. Amplification of unknown sequences upstream of known sequence by anchored PCR employs a slightly different strategy than for amplification of unknown downstream sequences. To obtain unknown upstream sequences, the reverse transcription reaction is anchored by one of the sequence-specific primers. The resulting cDNA is then modified or "tailed" in a terminal deoxynucleotidyltransferase catalyzed reaction at the 3' end by the addition of a poly (A)$^+$ tail. Two PCR reactions mediated by two sequence-specific primers and oligo (dT) complementary to the newly synthesized tail is carried out as above to yield the desired unique product.

Subcloned cDNA fragments were manually sequenced by dideoxy nucleotide chain termination using the Sequenase Version 2.0 DNA sequencing Kit (Amersham, Arlington Heights, Ill.) and α-$^{35}$S-dCTP. Both strands are analyzed at least twice using either vector-specific primers or custom oligonucleotide primers.

j. characterization of IPM 200 genomic and cDNA sequences

To identify bacterial artificial chromosome (BAC) clones containing the human IPM 200 gene, several PCR primer pair were generated in accordance with the human IPM 200 cDNA sequence. A commercially available BAC library (Genome Systems, St. Louis, Mo) was screened with the primers, and three positive clones, designated BAC 493P03, 366H7, and 325H22 were obtained. The human genomic DNA contained in these clones was then isolated and fragmented by digestion with either HindIII, SacI or EcoRI restriction endonucleases. The resulting fragments were ligated either into dephosphorylated vector pBluescript SK- or pClonesure without further purification.

Following transformation by electroporation into *E. coli* TOP 10, cells were grown overnight at 37 C. on LB-broth based agar plates containing carbencillin (50 µg/ml). From each restriction digest 48 subclones were selected at random from these plates and arrayed in a 96 well microtiter plates. In order to identify subclones containing specific regions of IPM 200 nitrocellulose membranes were placed on LB-agar plates containing carbencillin and a small number of cells from each subclone was transferred to establish colonies directly on the membranes. Colonies were grown overnight at 37° C. DNA bound to the filter was then denatured by incubation in 0.5 M NaOH, 1.5 M NaCl for 5 minutes, neutralized in 1 M Tris (pH 8.0), 1.5 M NaCl for 5 minutes, briefly rinsed in 2×SSC and crosslinked to the membranes by UV irradiation. The filters were incubated overnight with oligonucleotides, designed according to the IPM 200 cDNA sequence, which had been radiolabeled by incubation with T4 polynucleotide kinase in the presence of g32(P)ATP. Following removal of unbound probe, filters were exposed to x-ray film in order to identify subclones yielding hybridization signals.

Plasmids were isolated from these colonies and sequenced using either the primers used during the hybridization or additional, specifically designed primers. Alternatively, genomic sequences were derived by directly sequencing purified BAC DNA using specific oligonucleotide primers. Exonic sequences were determined by comparison of the obtained genomic sequences to the cDNA.

k. Comparisons Between Nucleotides or Amino Acid Sequence.

Alignment of the human IPM 150 and IPM 200 amino acid sequences reveal that the size, distribution and overall organization of exons is highly conserved between the two genes. Closer analysis indicates that regions of high amino acid sequence conservation correspond directly to regions in which the genomic organization is more stringently preserved. In regions of the genes that encode the more highly conserved amino- and carboxy-terminal regions of the IPM 150 and IPM 200 proteins, the intron/exon boundaries often occur precisely at the same amino acid (see, e.g., FIG. 4). The conservation of genomic structure is less stringent in the regions that encode the central domains of the IPM 150 and IPM 200 proteins. These are the same regions in which the primary structures of the proteins are also less conserved.

Example 2

Characterization of IPM 150 and IPM 200 Oligosaccharides

In order to characterize potential variations between IPM 150 and IPM 200 oligosaccharides, to determine the types of oligosaccharides present, and to determine the specific regions of the core glycoproteins that are glycosylated in normal and diseased tissue, CNBR peptides of normal human and monkey IPM 150 and IPM 200 proteins are generated and their oligosaccharides characterized.

a. CNBR Maps/Dot Blots. CNBR peptides are generated from human and monkey IPM 150 and IPM 200 proteins. Based on the amino acid sequences obtained from the amino-termini of each peptide, the position of the peptide within the core protein are identified, assuming the complete deduced amino acid sequences are available from cDNAs encoding IPM 150 and IPM 200. For any given peptide that contains a putative oligosaccharide or GAG attachment consensus sequence, one can determine whether that site is glycosylated.

In order to determine which CNBR peptides are glycosylated, CNBR peptides are incubated with various glycosidases (and/or other agents, such as nitrous acid, that remove oligosaccharides) in the presence of a protease inhibitor cocktail and separated by reverse phase HPLC. The resulting profiles are compared to profiles derived from non-deglycosylated CNBR peptides. A shift in any individual CNBR-derived peptide confirms that it is glycosylated. In addition, this provides information about the type of oligosaccharide and linkage involved. Subsequently, 2-4 µl of CNBR peptides in 0.1% TFA are applied to ProBlott membranes (Applied Biosystems) prewetted with methanol, followed by water, and placed on water-soaked Whitman 3M paper. Membranes are air-dried, rewetted in methanol and subsequently soaked in 15 ml of blocking buffer (50 mM Tris-HCl containing 0.5 M NaCl, and 2% polyvinylpyrrolidone-360), pH 7.5, for one hour at room temperature. The membranes are incubated for 1-2 hours, at room temperature, in blocking buffer containing 10 µl/ml of various HRP-conjugated lectins (including PNA, WGA, LFA, and Con-A) or antibodies (e.g., AC6S) followed by the appropriate HRP-conjugated secondary antibodies. In order to confirm that specific CNBR peptides are glycosylated, they are incubated in the presence of glycosidase(s) (including O-glycosidase, N-glycosidase, chondroitinase, heparanase, neuraminidase), reapplied to ProBlott, reprobed with the same lectins and/or antibodies, and compared to their nondeglycosylated precursors. These blots are utilized to determine the specificities of various monoclonal and polyclonal antibodies for core protein and/or carbohydrate epitopes.

b. Fluorophore-Assisted Carbohydrate Electrophoresis. Oligosaccharides associated with IPM 150 and IPM 200 are profiled, the monosaccharide compositions of specific oligosaccharides (or of the collective oligosaccharide composition of IPM 150 and IPM 200) are determined, and specific oligosaccharides are isolated, purified, and sequenced. This is accomplished using fluorophore-assisted carbohydrate electrophoresis (FACE), a recently developed technology based on the separation of fluorophore-derivatized carbohydrates on polyacrylamide gels (Glyko; Novato, Calif.).

c. Release of Oligosaccharides. Oligosaccharides are released from intact IPM 150 and IPM 200 and/or from CNBR peptides. O-linked sugars are released with O-glycosidase, N-linked oligosaccharides with endoglycosidase H or N-glycosidase F, and GAGs with nitrous acid. These methods preserve a free reducing end on the oligosaccharides that are labeled by reductive amination with the fluorescent tag, 1-aminoaphthalene-3, 6, 8-trisulfonic acid (ANTS). Once labeled with ANTS, all carbohydrates acquires a net negative charge that allow their separation on polyacrylamide gels. Pre-packaged kits for all these methods are used as supplied by Glyko (Novato, Calif.).

d. Separation of Oligosaccharides. Oligosaccharides (native or sialyated oligosaccharides following removal of sialic acid) as large as 100 kDa are separated based on size, in comparison with a mixture of dextran standards (or used unsaturated oligosaccharides for GAGs). Since the separation of oligosaccharides is influenced by the charge/mass ratio of the saccharide as well as its hydrodynamic volume, oligosaccharides that contain sialic acid migrate faster than larger neutral oligosaccharides. These separations provide information pertaining to the degree and type of glycosylation on individual CNBR peptides.

e. Monosaccharide Composition Analyses. Individual oligosaccharides are eluted from polyacrylamide gels and hydrolyzed into free monosaccharides using acid hydrolysis. Monosaccharides are labeled with ANTS and separated electrophoretically on 5% gels. The resulting profiles of neutral, amine and sialic acids is compared to monosaccharide standards. Gels are photographed using an electronic imaging system based on a CCD camera. Quantitative analyses of the resolved components is obtained by high-resolution, computer-assisted image analysis.

f. Oligosaccharide Sequencing. Oligosaccharides eluted from gels are exposed to a battery of specific glycosidic enzymes (including neuraminidase, β-galactosidase, hexosaminidase, α-mannosidase, β-mannosidase, and fucosidase) and rerun on polyacrylamide gels. Migration patterns of variously treated oligosaccharides provide sequence information of specific oligosaccharides. Should more specific data on linkage analysis be required, purified IPM 150 and IPM 200 and/or CNBR peptides derived from these proteoglycans can be sent to the Complex Carbohydrate Research Center (Athens, Ga.) for analyses using gas chromatography-mass spectrometry, fast atom bombardment/mass spectrometry or nuclear magnetic resonance.

Example 3

Characterization of Foveal IPMC Protein Glycoconjugates

Western blot analyses was used to characterize the size(s) and carbohydrate composition(s) of fovea-associated IPM glycoproteins and proteoglycans. 1-1.5 mm diameter punches of monkey and human foveas were homogenized in PBS containing protease inhibitors.

A portion of the homogenate was digested with chondroitinase ABC and another portion completely deglycosylated. The enzyme-treated and untreated portions were separated by SDS-PAGE and electroblotted onto nitrocellulose. The blots were probed with antibodies generated against components of the extrafoveal IPM, including IPM 150 and IPM 200. Reaction of these antibodies with fovea-derived bands of the same apparent molecular weight(s) as IPM 150 and IPM 200 indicate that the fovea contain the same, or similar, proteoglycans present in the extrafoveal IPMC protein.

In addition, the identification of IPM 150 and IPM 200 core glycoproteins in the lanes from non-chondroitinase-treated foveas provided evidence that foveal IPMC core proteins are similar to IPM 150 and/or IPM 200, except for the presence of chondroitin sulfate. Blots were also incubated with various lectins that bind to foveal IPMC protein. Various bands were excised and their N-terminal amino acid sequences determined to assess sequence homology with IPM 150 and IPM 200. Alternatively, previously undescribed glycoproteins were identified on these blots using probes that bind foveal IPMC protein. In this case, amino acid sequences of the proteins in these bands were obtained to determine whether they are unique or whether they are glycanated variants of IPM 150 and IPM 200. Should they possess the same core protein, but different carbohydrates, the CNBR strategy can be employed to characterize their oligosaccharides. Concurrent with the biochemical studies, sections of normal human foveas were hybridized with various probes, including IPM 150 and IPM 200 DNA probes, to determine whether messages encoding IPM 150 and/or IPM 200 are expressed in foveal cones.

Example 4

Characterization of Other Identified Soluble and Insoluble IPMC Protein Constituents An additional number of insoluble IPMC protein-associated glycoproteins and proteoglycans have been identified in human and monkey retinas. These include distinct 105 kDa and 80 kDa glycoproteins bound by a number of IPM-specific antibodies, a 140 kDa proteoglycan that migrates on gels without prior chondroitinase treatment, and a 150 kDa neuraminidase-resistant PHA-L-binding glycoprotein. These molecules can be characterized using procedures similar to agarose gel electrophoresis, in combination with Western blotting. Proteins are separated on one- or two-dimensional gels, transferred electrophoretically to nitrocellulose membranes and proteins or CNBR/tryptic peptides derived from them sequenced. Unique proteins are characterized further. The sequence information are then used to design degenerate oligonucleotide probes for RT-PCR of retinal RNA using a strategy similar to hat employed in isolating IPM 150-associated cDNA clones.

The HPLC-purified peak that contains 800-900 kDa molecules following chondroitinase treatment can be digested with CNBR to determine whether this high molecular weight IPM components contains glycoconjugates other than IPM 150 and IPM 200. This is accomplished by comparing the CNBR peptide profiles to those of IPM 150 and IPM 200. If these profiles suggest the existence of additional molecules, these fragments are collected and subjected to amino acid sequencing to determine potential homology to other molecules. It is also anticipated that this high molecular weight peak can contain hyaluronan; this is based on our hypothesis that IPMC hyaluronan can stabilize the IPMC protein through interactions with CD44 and/or IPM 150 and IPM 200. In order to determine the presence of hyaluronan in this peak, the peak are analyzed using FACE.

Example 5

Preparation of Anti-IPMC Antibodies a. Generation of Antibodies Directed Against IPM 150- and IPM 200-Derived Peptides. Polyclonal antibodies are generated against amino- and carboxy-termini peptides of IPM 150 and IPM 200. If the core protein amino acid sequences are strikingly similar, it is unlikely that synthetic peptide antibodies distinguish between the two proteoglycans. If this is the case, antibodies are generated against CNBR-derived peptides from IPM 150 and IPM 200 that share the same, or similar, amino acid sequences, but exhibit significant differences in their oligosaccharide compositions.

b. Synthetic and CNBr Peytides as Immunogens. Two general approaches are available for generation of synthetic peptides; these include preparation of antigens from bacterial over expression vectors or synthesis of peptides by solid-phase technology. Both approaches have their inherent advantages and disadvantages. The solid-phase approach has major advantages if the antigen is known to be highly conserved because of the way in which the peptide is displayed to the immune system, since particular regions of protein can be targeted specifically for antibody production, and because they can be prepared immediately after determining the amino acid sequence. However, the disadvantages are that the resulting antibodies may not recognize the native antigen and that they are more expensive to produce than bacterial fusion protein antigens.

c. Immunizations and Screening of Antisera. New Zealand white rabbits and chickens have been utilized for the development of heterologous antisera against IPM 150- and IPM 200-derived peptides. Synthetic and CNBr-derived IPMC peptides are coupled to keyhole limpit hemocyanin (KLH) using glutaraldehyde as a crosslinker prior to immunization. Some rabbits can be immunized with nonsense peptides of the same size; the resulting antisera are used as controls. Other carriers (including BSA, ovalbumin or PPD) and bifunctional crosslinkers, can be utilized in the event that KLH-conjugated peptides precipitate or do not elicit an immune reaction. As an alternative strategy, multiple antigen peptides (MAPS) can be synthesized on an immunologically inert lysine dendritic core using F-moc chemistry. Anti-peptide polyclonal antibodies with high titer values can be generated using this relatively new technique.

Immunogens are injected subcutaneously (500 µl/site; 10 sites/animal) and/or subscapularly (100 µl/site; 40 sites/animal). Test bleeds from the marginal ear vein (5-10 ml) are made 7-14 days following the second immunization and assayed for specific activity by immunofluorescence and immunoblotting. Rabbits producing relatively high titers of specific antibody activity are continued on "booster" immunizations every 6 weeks. These animals are bled every two weeks and the antisera stored in aliquots at −80° C. Polyclonal antibodies raised against peptides are purified from rabbit anti-serum on a column of the immunogen coupled to thiol-Sepharose 4B (Pharmacia, LKB, Biotechnology). Antibodies are eluted with 0.1 M glycine HCl (pH 2.8) into Tris-buffered saline (0.02 M Tris-HCl, pH 7.4, and 0.15 M NaCl) and dialyzed. Antibody capture assays using purified peptide of origin coupled to a solid phase (e.g. ELISA) can be used to determine antigenicity, to quantitate antibody titers, and to compare epitopes recognized by different antibodies. This approach allows one to determine rapidly whether antibodies distinguish between IPM 150- and IPM 200- derived or synthetic peptides. Chickens have been immunized using a similar protocol except that IgY is isolated from egg yolks.

Once the antibodies are generated, they can be screened on Western blots and tissue sections to determine their specificities for native IPM 150 and IPM 200. Controls include the use of preimmune sera and nonsense peptide antibodies. For immunogens coupled to KLH, positive sera are screened in assays using a second glutaraldehyde-coupled peptide since, in some cases, the glutaraldehyde bridge forms a portion of an epitope recognized by the antibody. Antibodies to carrier proteins or to the coupling reagent are removed by affinity purification of the anti-peptide antibodies on columns prepared with conjugates of the peptide to a second carrier molecule. Based on previous experiences, it is anticipated that antibodies of high titer can be produced that distinguish IPM 150 from IPM 200.

d. Generation of Monoclonal Antibodies. Monoclonal antibodies have been generated using an in vivo immunization technique known generally in the art. Balb/C mice were immunized with IPM 150 and IPM 200 peptides. Hybridomas showing high specific antibody concentrations and activity were cloned by means of limiting dilution and the monoclonal antibodies produced employed in immunohistochemical and morphological assays. Some hybridomas were propagated as ascites tumors by injection of these cells into pristane-primed Balb/C mice.

e. Lectin and Antibody Immunohistochemistry. Eyecups from normal, immature, aged and diseased humans were fixed in 4% formaldehyde in 100 mM sodium cacodylate buffer, for 2-4 hr, and then rinsed for 6 hr, embedded in acrylamide, frozen in liquid nitrogen, and sectioned to a thickness of 5-6 µM. FITC-conjugated lectins or antibodies, followed by the appropriate FITC-conjugated secondary antibodies, are applied to sections as published previously. Competitive haptens, preimmune sera and other appropriate controls are utilized in all studies.

Example 6

Substructural Localization of IPM 150 and IPM 200 in Cone Matrix Sheaths a. The CMS is not only a biochemically distinct component of the IPM, but is structurally distinct as well. Longitudinally-orientated filaments extend the entire length of the CMS and terminate in filamentous rings at its apical and basal ends. The relationship of IPM 150 and IPM 200 to the longitudinal filaments of CMSs and elucidation of their topographical association with VnR at the surface of cone inner segment ellipsoids and rod photoreceptors can be determined as follows.

Retinas were dissected from human and monkey eyes and rinsed in ice cold 10 mM PBS, pH 7.4, containing 1 mM $CaCl_2$ and 1 mM $MgCl_2$ and placed in ice-cold distilled water containing 2mM $CaCl_2$ to remove sheets of insoluble IPM. The isolated IPMC preparations were then transferred to calcium-free distilled water, which resulted in expansion of CMSs, thereby facilitating visualization of their substructural organization. IPMC protein preparations were fixed in 4% paraformaldehyde, in some cases. These preparations were subsequently exposed to one or more FITC-conjugated lectins, IPM 150/IPM 200 synthetic peptide-and CNBr-derived antibodies, and/or other IPM-binding antibodies, followed by exposure to the appropriate secondary antibody conjugated to FITC or rhodamine. Appropriate controls were utilized to confirm specificity.

The IPMC protein preparations were visualized by epifluorescence or confocal microscopy to determine the distribution of antibody-recognized epitopes. Confocal microscopy using a BioRad MRC-600 laser scanning confocal imaging system permitted visualization of thin optical sections; a Z-series of serial confocal images was recorded and computer assembled to give a three-dimensional image of the labeled IPM. Kalman averaging of confocal images was performed with at least 20 images taken at each level and images analyzed using COMOS, a windows-driven software program. If higher resolution is required, electron microscopic immunocytochemistry can be performed.

b. In Situ Hybridization. In situ hybridization was used to determine the cellular sources of specific mRNAs encoding IPMC protein molecules. Using the Riboprobe® System (Promega), $^{35}S$-labeled anti-sense and sense RNA probes were synthesized from a 605 bp fragment of the human IPM 150 cDNA, spanning from bases 1636 to 2241 in the presence of ribonuclease inhibitor and the appropriate primer (T3 or T7 depending on the desired template). Eyes and other tissues were fixed in 4% paraformaldehyde (+/− 0.5% glutaraldehyde), dehydrated in ethanol and embedded in diethylene glycol distearate. 1 µm thick tissue sections were cut, the embedding medium removed with toluene, and the tissue rehydrated with decreasing amounts of ethanol in DEPC-treated water. Sections were then incubated in 0.1 M triethanolamine and 0.25% acetic anhydride, pH 8.0, subsequently rinsed in 2×SSC and water, and then air-dried. Hybridization was conducted in 15 µl hybridization buffer composed of 50% formamide containing 10 mM Tris-HCl, 0.3M NaCl, pH 8.0, 1 mM EDTA 10% dextran sulfate, 5 µg/ml yeast tRNA, 100 mM DTT, 1×Denhardt's solution and $4 \times 10^5$ dpm of probe, at 42° C., for 14-16 hr. Evaporation was prevented by covering the sections with a NaOH-washed coverslip and sealing the edges with rubber cement. A negative control, consisting of the sense probe, was present on an adjacent tissue section on each slide.

After hybridization, the coverslips were removed and unhybridized probe rinsed off using several washes of 4×SSC, followed by a treatment with DNase free RNase A (10 µg/ml). The slides were washed twice for 15 min in 2×SSC, at room temperature, and three times for 15 min in 0.1×SSC at 45° C. followed by dehydration in increasing concentrations of ethanol. The slides were dipped in a 1:1 dilution of Kodak NTB-2 emulsion and stored in a light-tight box at 4° C. At various exposure times, slides were developed in D19, stained with 1% toluidine blue and visualized by light microscopy. Provided section thickness is constant and that control and experimental slides are processed at the same time and in replicates, quantitative date (grains/µm$^2$ of tissue) can be generated, if necessary.

c. In Situ RT-PCR. To distinguish between various populations of cells (e.g. rods versus cones) in developing, aging and/or pathologic retinas, in situ RT-PCR can be utilized. Larrick (1992), *Trends Biotechnol.* 10:146-152; Wang et al. (1989), *Proc. Natl. Acad. Sci.* USA 86:9717-9721. Fresh tissue can be fixed in 4% paraformaldehyde in PBS, washed in PBS, dehydrated in a series of graded ethanols and embedded in paraffin. Staecker et al. (1994), *Biotechniques* 16:76-80. 3 µm sections are cut and mounted on silanized slides, paraffin is removed at 55° C. and the tissue is rehydrated. The sections are digested in a solution of 1 µg/ml Pronase in 50 mM Tris-HCl, pH 7.5, and 5 mM EDTA for 30 min at 37° C. and then washed. DNA is degraded by an overnight incubation in RNase-free DNase in the presence of RNase inhibitor and the solution removed by washing the slides in a large volume of 50 mM Tris-HCl, pH 7.5.

RNA exposed on sections is reverse transcribed in 10 µl of a buffer containing 5 mM KCl, 1 mM Tris-HCl, pH 8.3, 5 mM MgCl, 10 mM dNTPs, 1 ng downstream primer, 1 µl RNase inhibitor, 8 µl DEPC-treated water and 20U M-MLV reverse transcriptase. The specimens are covered with Parafilm and incubated in a moist chamber, at 42° C., for one hr. The RT mixture is then replaced with a PCR mixture including 100 ng PCR primers and 1 µl $\alpha^{35}$S-dATP. The specimens are then coverslipped and heated to 75° C. Once this temperature is achieved the coverslip is removed and a preheated aliquot containing 1 µl Taq polymerase added for 20 cycles of amplification. Slides are washed and processed for autoradiography.

To determine absolute differences in the abundance of particular mRNAs in developing, aging or diseased tissues, e.g., retinas, quantitative competitive RT-PCR can be employed. Wang et al. (1989), *Proc. Natl. Acad. Sci.* USA 86:9717-9721; Golde et al. (1990), *Neuron* 4:253-267. This technique is accurate enough to detect differences in mRNA levels as small as 2-3 fold.

d. RNA Isolation. Total RNA was isolated from retinal, other ocular, and extraocular tissues (all major organs) based on the method of Chirgwin et al. (Chirgwin et al. (1979), *Biochemistry* 18:5294-5299), except that cesium trifluoroacetate (Pharmacia) was used instead of CsCl, or by using TRIzol (Gibco BRL) in a protocol based on the method of Chomczynski and Sacchi (Chomczynski and Sacchi (1987), *Anal. Biochem.* 162:156-159). The resulting pellet was stored at −80° C. until required for cDNA synthesis, Northern blot analyses or RT-PCR. When mRNA was required, it was isolated from total RNA using an oligo-dT cellulose-based protocol (Micro Fast-Track-mRNA Isolation kit; Invitrogen Corp.) in which poly (A)$^+$ RNA was bound to oligo(dT) cellulose, washed and subsequently eluted. This method permitted the isolation of 1-5 µg poly (A)+ RNA per human retina. The quality/integrity of RNA obtained was assessed on agarose gels and on Northern blots.

e. Northern Blot Analyses: Total RNA and/or poly (A)$^+$ RNA from various ocular and non-ocular tissues was isolated as described above and fractionated on denaturing (formaldehyde-containing) agarose gels. Prior to electrophoresis the samples were denatured by heating at 55° C., for 15 min., in 6.5% formaldehyde and 50% formamide in MOPS running buffer (40 mM morpholinopropanesulfonic acid, pH 7.0, containing 100 mM sodium acetate and 10 mM EDTA). After electrophoresis, the samples were transferred to nitrocellulose or nylon-based membranes by capillary transfer using 20×SSC. The RNA immobilized on the membranes was hybridized with a specific $^{32}$P-labeled cDNA probe (clone 70-1-1, corresponding to bp 350-899 of the human cDNA) for detection of the corresponding transcripts and a control actin cDNA to ascertain successful transfer and integrity of the sample.

f. Tissue Expression. A commercially available RNA dot-blot containing 100-500 ng poly A$^+$ RNA from various human tissue sources (Clontech Laboratories Inc., Palo Alto, Calif.) was probed with a $^{32}$P-labeled cDNA corresponding to nucleotides 817-3160 of human IPM 150. Hybridization and rinse conditions were exactly as described above.

In order to determine the cellular source(s) of IPM 150, Northern and in situ hybridization analyses have been conducted. IPM 150 cDNA probes hybridized to a 3.9 kb transcript that is present in relatively high abundance in retinal RNA. Occasionally, a larger transcript of approximately 6.5 kb was also detected, albeit at a much reduced signal strength. No signal was detected on Northern blots of RNA isolated from RPE/choroid, iris or cornea, suggesting that, in the human eye, IPM 150 was transcribed only in the neural retina. Dot blot analyses of polyA$^+$ RNA from 50 different adult and fetal human tissues indicate that IPM 150 mRNA, or transcripts with a similar nucleotide sequence are present in adult lung, liver, kidney, thymus and small intestine. Weak hybridization to fetal lung and thymus RNA as well as a number of additional adult tissues, was also observed. Distinct hybridization of IPM 150 antisense riboprobes to the human retinal outer nuclear layer (ONL) was observed on sections of human retina, RPE and choroid. IPM 150 transcripts were present within both rod and cone photoreceptor cells. No labeling of any other region was observed.

EXAMPLE 7

In Vivo Assessment of RGD-Dependent Adhesion System a. In order to determine whether adhesion is maintained by an RGD-dependent mechanism involving IPM 150, IPM 200, and/or other IPMC constituents in normal versus diseased tissue, a variety of blocking antibodies and RGD-containing peptides are injected into the subretinal space of monkeys and pigs. RGD-containing peptides and/or antibodies directed against integrins have been used to inhibit cell adhesion in culture. Akiyama et al. (1989), *J. Cell Biol.* 109:863-875; Hayashi et al. (1992), *J. Cell Biol.* 119:945-959; Ruoslahti (1988), *Annual Rev. Cell Biol.* 4:229-255; Wayner et al. (1991), *J. Cell Biol.* 113:919-929. Similarly, antibodies to various cell adhesion molecules have been utilized to perturb adhesion in the retina in vivo. Hageman et al. (1995), *Arch. Ophthalmol.* 113:655-660.

Pigs can be utilized for these studies in order to develop the assay and to provide initial information. Provided these initial studies perturb retinal adhesion, the results are confirmed in monkeys. Groups of 4 pigs each are injected subretinally with either 1) RGD-containing peptides known to inhibit VnR-based adhesion (GRGDSP (SEQ ID NO:32), GRGDTP (SEQ ID NO:33), GdRGDSP (SEQ ID NO:34), n-Me-GRGDSP (SEQ ID NO:35), GRGDSPASSK (SEQ ID NO:36), and GPenGRGDSPCA (SEQ ID NO:37)) or, 2) blocking VnR antibodies [mouse anti-human $\alpha V\beta 5$ (PVF6); mouse anti-human $\alpha V$ (VNR147 and VNR139); rabbit anti-human $\alpha V\beta 3/5$]. Initially, F(ab) or F(ab)$_2$ fragments of these antibodies can be prepared and utilized. Peptides (50 μg/ml) or antibodies (1:100) are dissolved in Hanks solution, pH 7.3, and loaded into a micropipette with tip diameter of approximately 50 μm. The micropipette is inserted through a limbal slit and passed across the vitreous until the tip penetrates the central retina. Approximately 5 μl is injected into the subretinal space, creating a small 3-4 mm diameter retinal detachment. A similar bleb is made in another quadrant using Hanks solution containing non-sense peptides or antibodies or Hanks solution alone. IPMC protein diffusion is confirmed by injecting a $^{14}C$-labeled peptide followed by tissue autoradiography.

ERG recordings are made on each of the 4 animals in each group immediately prior to euthanasia at 6 hr, 12 hr, 24 hr and 48 hr following injection and retinal adhesion estimated using an established peeling assay. Garvey et al. (1988) in Peptides: Chemistry and Biology, G. R. Marshall, ed., ESCOM, Leiden, Netherlands. In brief, eyes are enucleated rapidly (within 15-30 seconds) and the retinas are peeled manually from the RPE in the quadrant containing the retinal bleb, within 30 sec after enucleation. The peeled retinas are fixed for immunohistochemical studies to determine the effects of these peptides and antibodies on IPM structure (especially cone matrix sheaths) and to determine the percentage of retina covered with pigment (to be scored 0-100%, in increments of matrix sheaths) and to determine the percentage of retina covered with pigment (to be scored 0-100%, in increments of 10%, where 100% indicates firmest adhesion). A zone of decreased or no pigment adherence around the original injection sites indicates a loss of retinal adhesiveness beyond the site of injection, providing evidence that the VnR participates in adhesion via an RGD-dependent system. This assay is based on previous observations suggesting that the attachment of cone matrix sheaths to cells of both the RPE and the neural retina is sufficiently strong to result in layers of RPE being separated from Bruch's membrane following manual separation of the neural retina from the RPE within two minutes of death in primates. The basis for this post-mortem loss in adhesiveness is most likely related to physiological dysfunction of an adhesion receptor-ligand system, rather than to degradation of IPM (especially cone matrix sheaths) constituents since no changes in either the structure or distribution of the IPM-associated molecules is observed until approximately 3-4 hours post-mortem in human eyes. The procedures outlined above must be conducted within the first couple of minutes of death to provide meaningful data, since the molecular mechanism that mediates adhesion between the IPM and RPE is extremely sensitive to post-mortem changes. Bums and Feeney-Bums (1980), *Trans. Am. Ophth. Soc.* 78:206-225. The most straight forward result is one in which the retina easily separates from (or falls off) the RPE in a large zone surrounding the initial injection sight. In addition to the peeling assays, the effects of perturbants on retinal adhesion can be assessed anatomically. Krol et al. (1988), *BioTechniques* 6:958-976.

b. Identification of RGD Consensus Sequences in IPM 150 and IPM 200. Once obtained, the complete amino acid sequences of IPM 150, IPM 200, and other IPMC glycoprotein core proteins can be examined for the presence or absence of RGD consensus sequences. If an RGD consensus sequence(s) is identified, one can confirm that these proteoglycan core proteins are capable of binding to the VnR associated with photoreceptor and RPE cells. The techniques outlined below can be employed toward this goal.

c. IPMC Peptide Antibodies. In the event that IPM constituents contain RGD consensus sequences, antibodies can be generated against synthetic peptides containing the RGD sequence and adjacent flanking regions (or, if necessary, CNBr-derived peptides containing the RGD sequence). The specificity of these antibodies for an epitope containing RGD can be assessed using solid phase antibody capture assays. In addition, the binding of these peptide antibodies to native IPMC proteins can be assayed immunohistochemically. Provided these antibodies bind native IPMC proteins, they can be utilized in perturbation assays aimed at assessing the involvement of these constituents in retinal adhesion as outlined in above.

d. Ligand-Receptor Blotting. Isolated outer segments and cultured RPE cells (which express VnR) can be extracted for 1 hr, at 4° C., in PBS containing 2 mM PMSF, and 200 mM octylglucoside. This lysate is separated by non-denaturing PAGE and transferred electrophoretically to nitrocellulose membranes. Lazarus and Hageman (1992), *Invest. Ophthalmol. Vis. Sci.* 33:364-376. These membranes are incubated with biotinylated IPM 150 or IPM 200 core protein. The blots are washed and incubated with HRP-conjugated streptavidin and color-developed in DAB containing 0.01% hydrogen peroxide. Adjacent lanes are probed with polyclonal antibodies directed against $\alpha V$ and $\beta 3/5$ subunits and/or $\alpha V\beta 3/5$. Binding of IPM 150 or IPM 200 core proteins to these subunits indicates that IPMC proteins are capable of binding to VnR.

e. IPM Core Protein AffinitX Chromatography. IPMC protein core affinity columns are prepared by coupling 0.5 mg of proteoglycan core (either deglycosylated native proteoglycan or bacterially-expressed core) to 1 ml Sepharose CL-4B beads after CNBr activation (0.05 g/ml beads). RPE and outer segment lysates are centrifuged at 1000 g for 10 min, their supernatants subjected to the affinity column pre-equilibrated with 50 mM octylglucoside and 1 mM PMSF in PBS, pH 7.4, and eluted with a linear gradient of 0. 15-1 M sodium chloride and/or RGD-containing peptides in the presence of MgCl$_2$, CaCL$_2$ or EDTA followed by 0.1 M glycine and 8M urea. A control column is made using BSA coupled to Sepharose CL-4B. Fractions eluted from the column are analyzed on Western blots using antibodies directed against the $\alpha V$ and $\beta 3/5$ subunits of the VnR. If necessary, RPE cells are labeled with $^{125}I$ using the lactoperoxidase-catalyzed iodination for 40 min on ice to label VnR prior to chromatography.

f. Identification of Other Retinal Adhesion-Related Ligands in the IPMC Protein. Based on the observation that VnR and CD44 are associated with the plasma membranes of cells bordering the interphotoreceptor space, these adhesive receptors can mediate the linkage of photoreceptor, Muiller and RPE cells via are yet unidentified IPMC ligand(s). Since it is known that CD44 interacts specifically with hyaluronan and that the N-terminus of IPM 150 contains two potential hyaluronan binding motifs, we speculate that hyaluronan can stabilize the IPMC protein through interactions with CD44, IPM 150 and/or IPM 200. Such a system provides a framework for a molecular model of retinal adhesion, whereby IPMC proteins are bound to the extracellular domains of VnR and hyaluronan, on the one hand, and to CD44, on the other.

Hyaluronan (hyaluronic acid, hyaluronate), a high molecular mass polysaccharide secreted by many cell types, often plays a dynamic role in cell-extracellular matrix interactions. Ellison et al. (1991), *J. Biol. Chem.* 266:21150-21157. Immunohistochemical studies of normal, developing and aging primate retinas, employing antibodies directed against hyaluronan (e.g. clone N-DOG1), can be conducted to confirm the presence of hyaluronan within the IPM and to identify its distribution. The use of acrylamide embedding is advantageous in these investigations since it avoids the artifactual redistribution of normally hydrated IPMC proteins that occurs following tissue dehydration. The topographical relationship of hyaluronan to other IPMC proteins, including IPM 150 and IPM 200, can be assessed using isolated preparations of insoluble IPMC protein and the presence of hyaluronan in isolated IPMC protein can be determined biochemically using FACE. In addition, a battery of antibodies directed against various hyaluronan-binding proteins/receptors and epitopes and other ligands bound by CD44 and VnR can be screened on sections of retina, as they become available.

What is claimed is:

1. An isolated or recombinant polynucleotide comprising a nucleotide sequence or its complement, wherein said nucleotide sequence comprises at least 750 contiguous nucleotides of SEQ ID NO:1.

2. The isolated or recombinant polynucleotide of claim 1 comprising the sequence set forth in SEQ ID NO:1 or its complement.

3. The isolated or recombinant polynucleotide of claim 1, wherein said nucleotide sequence comprises at least 1000 contiguous nucleotides of SEQ ID NO:1.

4. The isolated or recombinant polynucleotide of claim 1, wherein said nucleotide sequence comprises at least 2000 contiguous nucleotides of SEQ ID NO:1.

* * * * *

SEQUENCE LISTING

```
<160> NUMBER OF SEQ ID NOS: 37

<210> SEQ ID NO 1
<211> LENGTH: 3330
<212> TYPE: DNA
<213> ORGANISM: Homo sapiens
<220> FEATURE:
<223> OTHER INFORMATION: Human IPM 150 cDNA, isoform A

<400> SEQUENCE: 1
taaaccaaga aggttatcct caatcatctg gtatcaatat ataattattt ttcacatttc      60
tgttactttt taatgagatt tgaggttgtt ctgtgattgt tatcagaatt accaatgcac     120
aaaagccaga atgtatttgg aaactagaag agctattttt gttttttgga tttttctcca     180
agttcaagga accaaagata tctccattaa catataccat tctgaaacta agacataga     240 caatccccca agaaatgaaa caactgaaag tactgaaaaa atgtacaaaa tgtcaactat     300
gagacgaata ttcgatttgg caaagcatcg aacaaaaaga tccgcatttt tcccaacggg     360
ggttaaagtc tgtccacagg aatccatgaa acagatttta gacagtcttc aagcttatta     420
tagattgaga gtgtgtcagg aagcagtatg ggaagcatat cggatctttc tggatcgcat     480
ccctgacaca ggggaatatc aggactgggt cagcatctgc cagcaggaga ccttctgcct     540 cttttgacatt ggaaaaaact tcagcaattc ccaggagcac ctggatcttc tccagcagag     600
aataaaacag agaagtttcc ctgacagaaa agatgaaata tctgcagaga agacattggg     660
agagcctggt gaaaccattg tcatttcaac agcaatctac atttcaaaga cttgggcagt     720
attctaagaa aaccctcaga agagcaaatt caagatgttg ccaacgtctc acttgggcct     780
ttccctctca ctcctgatga cacctcctc aatgaaattc tcgataatac actcaacgac     840
accaagatgc ctacaacaga aagagaaaca gaattcgctg tgttggagga gcagagggtg     900
gagctcagcg tctctctggt aaaccagaag ttcaaggcag agctcgctga ctcccagtcc     960
ccatattacc aggagctagc aggaaagtcc caacttcaga tgcaaaagat atttaagaaa    1020
cttccaggat tcaaaaaaat ccatgtgtta ggatttagac caagaaaga aaagatggc     1080 tcaagctcca cagagatgca acttacgcc atctttaaga gacacagtgc agaagcaaaa    1140
agccctgcaa gtgacctcct gtctttttgat tccaacaaaa ttgaaagtga ggaagtctat    1200
catggaacca tggaggagga caagcaacca gaaatctatc tcacagctac agacctcaaa    1260
aggctgatca gcaaagcact agaggaagaa caatcttgg atgtgggac aattcagttc    1320
```

-continued

```
actgatgaaa ttgctggatc actgccagcc tttggtcctg acacccaatc agagctgccc    1380
acatcttttg ctgttataac agaggatgct actttgagtc agaacttcc tcctgttgaa    1440
ccccagcttg agacagtgga cggagcagag catggtctac ctgacacttc ttggtctcca    1500
cctgctatgg cctctacctc cctgtcagaa gctccacctt tctttatggc atcaagcatc    1560
ttctctctga ctgatcaagg caccacagat acaatggcca ctgaccagac aatgctagta    1620
ccagggctca ccatccccac cagtgattat tctgcaatca gccaactggc tctgggaatt    1680
tcacatccac ctgcatcttc agatgacagc cgatcaagtg caggtggcga agatatggtc    1740
agacacctag atgaaatgga tctgtctgac actcctgccc catctgaggt accagagctc    1800
agcgaatatg tttctgtccc agatcatttc ttggaggata ccactcctgt ctcagcttta    1860
cagtatatca ccactagttc tatgaccatt gcccccaagg gccgagagct ggtagtgttc    1920
ttcagtctgc gtgttgctaa catggccttc tccaacgacc tgttcaacaa gagctctctg    1980
gagtaccgag ctctggagca acaattcaca cagctgctgg ttccatatct acgatccaat    2040
cttacaggat ttaagcaact tgaaatactt aacttcagaa acgggagtgt gattgtgaat    2100
agcaaaatga gtttgctaa gtctgtgccg tataacctca ccaaggctgt gcacggggtc    2160
ttggaggatt ttcgttctgc tgcagcccaa caactccatc tggaaataga cagctactct    2220
ctcaacattg aaccagctga tcaagcagat ccctgcaagt tcctggcctg cggcgaattt    2280
gcccaatgtg taaagaacga acggactgag gaagcggagt gtcgctgcaa accaggatat    2340
gacagccagg ggagcctgga cggtctggaa ccaggcctct gtggccctgg cacaaaggaa    2400
tgcgaggtcc tccagggaaa gggagctcca tgcaggttgc cagatcactc tgaaaatcaa    2460
gcatacaaaa ctagtgttaa aaagttccaa aatcaacaaa ataacaaggt aatcagtaaa    2520
agaaattctg aattactgac cgtagaatat gaagaattta accatcaaga ttgggaagga    2580
aattaaaaac tgaaaatgta caattatcac ttaggctatc tcaagagaga tgatttgcct    2640
tctcaaggaa aatggagaca ggcatattca tgggtcatca aaatccagac atacagtcaa    2700
cactgagaat cagcacacac catatttcaa atatagaaga gtcatgtact ggcaaccag    2760
taaattctga aaaaaagac acttacttat tattaaaacc ccaaatgcaa tcagcgaaac    2820
atatttttac tattcttgga tgatagtcaa aatgatcata agccaggttt gcttccacct    2880
tccctgaaaa ttttactcac agatcatttg caacaagcat agcttactta tgtttaggg    2940
actgaacaat ttattgggaa gcaaactctt tatatgctag aaagtacatt taaaagatga    3000
ctacttacgc agggagatgc aggtctctct aaacgcatga atgtatgtag tgtgtaggca    3060
ctgtagtgag tgtatatatg ctccacacta cgtctgataa acacaaacct cagtattcag    3120
ttattaggca cactagtttt atacgcaact actgcttaca tagtagactg ttttgttgcc    3180
aataatcttt gaattgttct ttaaaagaaa ctgaggttca gatacacata ccatggaaaa    3240
atcttacttt tcttgttact acacaaagct attttaaaga agatgctatg ttgggagaag    3300
ggcgaagttg tactatatga cataatcaat                                    3330
```

<210> SEQ ID NO 2
<211> LENGTH: 797
<212> TYPE: PRT
<213> ORGANISM: Homo sapiens
<220> FEATURE:
<223> OTHER INFORMATION: Human IPM 150 amino acid sequence, isoform A

<400> SEQUENCE: 2

```
Met Tyr Leu Glu Thr Arg Arg Ala Ile Phe Val Phe Trp Ile Phe Leu
 1               5                  10                  15

Gln Val Gln Gly Thr Lys Asp Ile Ser Ile Asn Ile Tyr His Ser Glu
             20                  25                  30

Thr Lys Asp Ile Asp Asn Pro Arg Asn Glu Thr Thr Glu Ser Thr
         35                  40                  45

Glu Lys Met Tyr Lys Met Ser Thr Met Arg Arg Ile Phe Asp Leu Ala
     50                  55                  60

Lys His Arg Thr Lys Arg Ser Ala Phe Phe Pro Thr Gly Val Lys Val
 65                  70                  75                  80

Cys Pro Gln Glu Ser Met Lys Gln Ile Leu Asp Ser Leu Gln Ala Tyr
                 85                  90                  95

Tyr Arg Leu Arg Val Cys Gln Glu Ala Val Trp Glu Ala Tyr Arg Ile
             100                 105                 110

Phe Leu Asp Arg Ile Pro Asp Thr Gly Glu Tyr Gln Asp Trp Val Ser
             115                 120                 125

Ile Cys Gln Gln Glu Thr Phe Cys Leu Phe Asp Ile Gly Lys Asn Phe
130                 135                 140

Ser Asn Ser Gln Glu His Leu Asp Leu Leu Gln Arg Ile Lys Gln
145                 150                 155                 160

Arg Ser Phe Pro Asp Arg Lys Asp Glu Ile Ser Ala Glu Lys Thr Leu
                 165                 170                 175

Gly Glu Pro Gly Glu Thr Ile Val Ile Ser Thr Asp Val Ala Asn Val
             180                 185                 190

Ser Leu Gly Pro Phe Pro Leu Thr Pro Asp Asp Thr Leu Leu Asn Glu
             195                 200                 205

Ile Leu Asp Asn Thr Leu Asn Asp Thr Lys Met Pro Thr Thr Glu Arg
210                 215                 220

Glu Thr Glu Phe Ala Val Leu Glu Gly Gln Arg Val Glu Leu Ser Val
225                 230                 235                 240

Ser Leu Val Asn Gln Lys Phe Lys Ala Glu Leu Ala Asp Ser Gln Ser
                 245                 250                 255

Pro Tyr Tyr Gln Glu Leu Ala Gly Lys Ser Gln Leu Gln Met Gln Lys
             260                 265                 270

Ile Phe Lys Lys Leu Pro Gly Phe Lys Lys Ile His Val Leu Gly Phe
     275                 280                 285

Arg Pro Lys Lys Glu Lys Asp Gly Ser Ser Thr Glu Met Gln Leu
     290                 295                 300

Thr Ala Ile Phe Lys Arg His Ser Ala Glu Ala Lys Ser Pro Ala Ser
305                 310                 315                 320

Asp Leu Leu Ser Phe Asp Ser Asn Lys Ile Glu Ser Glu Glu Val Tyr
                 325                 330                 335

His Gly Thr Met Glu Glu Asp Lys Gln Pro Glu Ile Tyr Leu Thr Ala
             340                 345                 350

Thr Asp Leu Lys Arg Leu Ile Ser Lys Ala Leu Glu Glu Gln Ser
             355                 360                 365

Leu Asp Val Gly Thr Ile Gln Phe Thr Asp Glu Ile Ala Gly Ser Leu
         370                 375                 380

Pro Ala Phe Gly Pro Asp Thr Gln Ser Glu Leu Pro Thr Ser Phe Ala
385                 390                 395                 400

Val Ile Thr Glu Asp Ala Thr Leu Ser Pro Glu Leu Pro Pro Val Glu
                 405                 410                 415

Pro Gln Leu Glu Thr Val Asp Gly Ala Glu His Gly Leu Pro Asp Thr
```

```
                  420                 425                 430
Ser Trp Ser Pro Pro Ala Met Ala Ser Thr Ser Leu Ser Glu Ala Pro
            435                 440                 445

Pro Phe Phe Met Ala Ser Ser Ile Phe Ser Leu Thr Asp Gln Gly Thr
        450                 455                 460

Thr Asp Thr Met Ala Thr Asp Gln Thr Met Leu Val Pro Gly Leu Thr
465                 470                 475                 480

Ile Pro Thr Ser Asp Tyr Ser Ala Ile Ser Gln Leu Ala Leu Gly Ile
                485                 490                 495

Ser His Pro Pro Ala Ser Ser Asp Asp Ser Arg Ser Ser Ala Gly Gly
            500                 505                 510

Glu Asp Met Val Arg His Leu Asp Glu Met Asp Leu Ser Asp Thr Pro
        515                 520                 525

Ala Pro Ser Glu Val Pro Glu Leu Ser Glu Tyr Val Ser Val Pro Asp
    530                 535                 540

His Phe Leu Glu Asp Thr Thr Pro Val Ser Ala Leu Gln Tyr Ile Thr
545                 550                 555                 560

Thr Ser Ser Met Thr Ile Ala Pro Lys Gly Arg Glu Leu Val Val Phe
                565                 570                 575

Phe Ser Leu Arg Val Ala Asn Met Ala Phe Ser Asn Asp Leu Phe Asn
            580                 585                 590

Lys Ser Leu Glu Tyr Arg Ala Leu Glu Gln Gln Phe Thr Gln Leu
        595                 600                 605

Leu Val Pro Tyr Leu Arg Ser Asn Leu Thr Gly Phe Lys Gln Leu Glu
    610                 615                 620

Ile Leu Asn Phe Arg Asn Gly Ser Val Ile Val Asn Ser Lys Met Lys
625                 630                 635                 640

Phe Ala Lys Ser Val Pro Tyr Asn Leu Thr Lys Ala Val His Gly Val
                645                 650                 655

Leu Glu Asp Phe Arg Ser Ala Ala Gln Gln Leu His Leu Glu Ile
            660                 665                 670

Asp Ser Tyr Ser Leu Asn Ile Glu Pro Ala Asp Gln Ala Asp Pro Cys
        675                 680                 685

Lys Phe Leu Ala Cys Gly Glu Phe Ala Gln Cys Val Lys Asn Glu Arg
    690                 695                 700

Thr Glu Glu Ala Glu Cys Arg Cys Lys Pro Gly Tyr Asp Ser Gln Gly
705                 710                 715                 720

Ser Leu Asp Gly Leu Glu Pro Gly Leu Cys Gly Pro Gly Thr Lys Glu
                725                 730                 735

Cys Glu Val Leu Gln Gly Lys Gly Ala Pro Cys Arg Leu Pro Asp His
            740                 745                 750

Ser Glu Asn Gln Ala Tyr Lys Thr Ser Val Lys Lys Phe Gln Asn Gln
        755                 760                 765

Gln Asn Asn Lys Val Ile Ser Lys Arg Asn Ser Glu Leu Leu Thr Val
    770                 775                 780

Glu Tyr Glu Glu Phe Asn His Gln Asp Trp Glu Gly Asn
785                 790                 795

<210> SEQ ID NO 3
<211> LENGTH: 2887
<212> TYPE: DNA
<213> ORGANISM: Homo sapiens
<220> FEATURE:
<223> OTHER INFORMATION: Human IPM 150 cDNA sequence, isoform B
```

```
<400> SEQUENCE: 3
gggagctatt tttgtttttt ggattttcct ccaagttcaa ggaaccaaag tgtgtcagga    60
agcagtatgg gaagcatatc ggatctttct ggatcgcatc cctgacacag gggaatatca   120
ggactgggtc agcatctgcc agcaggagac cttctgcctc tttgacattg gaaaaaactt   180
cagcaattcc caggagcacc tggatcttct ccagcagaga ataaaacaga gaagtttccc   240
tgacagaaaa gatgaaatat ctgcagagaa gacattggga gagcctggtg aaaccattgt   300
catttcaaca gatgttgcca acgtctcact tgggcctttc cctctcactc ctgatgacac   360
cctcctcaat gaaattctcg ataatacact caacgacacc aagatgccta acagagaaag   420
agaaacagaa ttcgctgtgt tggaggagca gagggtggag ctcagcgtct ctctggtaaa   480
ccagaagttc aaggcagagc tcgctgactc ccagtcccca tattaccagg agctagcagg   540
aaagtcccaa cttcagatgc aaaagatatt taagaaactt ccaggattca aaaaaatcca   600
tgtgttagga tttagaccaa agaaagaaaa agatggctca agctccacag agatgcaact   660
tacggccatc tttaagagac acagtgcaga agcaaaaagc cctgcaagtg acctcctgtc   720
ttttgattcc aacaaaattg aaagtgagga agtctatcat ggaaccatgg aggaggacaa   780
gcaaccagaa atctatctca cagctacaga cctcaaaagg ctgatcagca agcactaga    840 ggaagaacaa tctttggatg tggggacaat tcagttcact gatgaaattg ctggatcact   900
gccagccttt ggtcctgaca cccaatcaga gctgcccaca tcttttgctg ttataacaga   960
ggatgctact tgagtccag aacttcctcc tgttgaaccc cagcttgaga cagtggacgg   1020
agcagagcat ggtctacctg acacttcttg gtctccacct gctatggcct ctacctccct  1080
gtcagaagct ccacctttct ttatggcatc aagcatcttc tctctgactg atcaaggcac  1140
cacagataca atggccactg accagacaat gctagtacca gggctcacca tccccaccag  1200
tgattattct gcaatcagcc aactggctct gggaatttca catccacctg catcttcaga  1260
tgacagccga tcaagtgcag gtggcgaaga tatggtcaga cacctagatg aaatggatct  1320
gtctgacact cctgccccat ctgaggtacc agggctcagc gaatacgttt ctgtcccaga  1380
tcatttcttg gaggatacca ctcctgtctc agctttacag tatatcacca ctagttctat  1440
gaccattgcc cccaagggcc gagagctggt agtgttcttc agtctgcgtg ttgctaacat  1500
ggccttctcc aacgacctgt tcaacaagag ctctctggag taccgagctc tggagcaaca  1560
attcacacag ctgctggttc catatctacg atccaatctt acaggattta agcaacttga  1620 atacttaac ttcagaaacg ggagtgtgat tgtgaatagc aaaatgaagt ttgctaagtc  1680
tgtgccgtat aacctcacca aggctgtgca cggggtcttg gaggattttc gttctgctgc  1740
agcccaacaa ctccatctgg aaatagacag ctactctctc aacattgaac cagctgatca  1800
agcagatccc tgcaagttcc tggcctgcgg cgaatttgcc caatgtgtaa agaacgaacg  1860
gactgaggaa gcggagtgtc gctgcaaacc aggatatgca agccagggga gcctggacgg  1920
tctggaacca ggcctctgtg gccctggcac aaaggaatgc gaggtcctcc agggaagggg  1980
agctccatgc aggttgccag atcactctga aaatcaagca tacaaaacta gtgttaaaaa  2040
gttccaaaat caacaaaata caaggtaatc agtaaaaga aattctgaat tactgaccgt  2100
agaatatgaa gaatttaacc atcaagattg ggaaggaaat taaaaactga aaatgtacaa  2160
ttatcactta ggctatctca agagagatga tttgccttct caaggaaaat ggagacaggc  2220
atattcatgg gtcatcaaaa tccagacata cagtcaacac tgagaatcag cacacaccat  2280
atttcaaata tagaagagtc atgtacttgg caaccagtaa attctgaaaa aaaagacact  2340
```

-continued

```
tacttattat taaaccccca aatgcaatca gcgaaacata ttttactat tcttggatga    2400 tagtcaaaat gatcataagc caggtttgct tccaccttcc ctgaaaattt tactcacaga    2460
tcatttgcaa caagcatagc ttacttattg tttagggact gaacaattta ttgggaagca    2520
aactctttat atgctagaaa gtacatttaa aagatgacta cttacgcagg gagatgcagg    2580
tctctctaaa cgcatgaatg tatgtagtgt gtaggcactg tagtgagtgt atatatgctc    2640
cacactacgt ctgataaaca caaacctcag tattcagtta ttaggcacac tagtttata     2700 cgcaactact gcttacatag tagactgttt tgttgccaat aatctttgaa ttgttcttta    2760
aaagaaactg aggttcagat acacatacca tggaaaaatc ttacttttct tgttactaca    2820
caaagctatt ttaaagaaga tgctatgttg ggagaagggc gaagttgtac tatatgacat    2880
aatcaat                                                               2887
```

<210> SEQ ID NO 4
<211> LENGTH: 719
<212> TYPE: PRT
<213> ORGANISM: Homo sapiens
<220> FEATURE:
<223> OTHER INFORMATION: Human IPM 150 amino acid sequence, isoform B

<400> SEQUENCE: 4

```
Met Tyr Leu Glu Thr Arg Arg Ala Ile Phe Val Phe Trp Ile Phe Leu
  1               5                  10                  15

Gln Val Gln Gly Thr Lys Val Cys Gln Glu Ala Val Trp Glu Ala Tyr
                 20                  25                  30

Arg Ile Phe Leu Asp Arg Ile Pro Asp Thr Gly Glu Tyr Gln Asp Trp
             35                  40                  45

Val Ser Ile Cys Gln Gln Glu Thr Phe Cys Leu Phe Asp Ile Gly Lys
         50                  55                  60

Asn Phe Ser Asn Ser Gln Glu His Leu Asp Leu Leu Gln Gln Arg Ile
 65                  70                  75                  80

Lys Gln Arg Ser Phe Pro Asp Arg Lys Asp Glu Ile Ser Ala Glu Lys
                 85                  90                  95

Thr Leu Gly Glu Pro Gly Glu Thr Ile Val Ile Ser Thr Asp Val Ala
                100                 105                 110

Asn Val Ser Leu Gly Pro Phe Pro Leu Thr Pro Asp Asp Thr Leu Leu
            115                 120                 125

Asn Glu Ile Leu Asp Asn Thr Leu Asn Asp Thr Lys Met Pro Thr Thr
        130                 135                 140

Glu Arg Glu Thr Glu Phe Ala Val Leu Glu Glu Gln Arg Val Glu Leu
145                 150                 155                 160

Ser Val Ser Leu Val Asn Gln Lys Phe Lys Ala Glu Leu Ala Asp Ser
                165                 170                 175

Gln Ser Pro Tyr Tyr Gln Glu Leu Ala Gly Lys Ser Gln Leu Gln Met
            180                 185                 190

Gln Lys Ile Phe Lys Lys Leu Pro Gly Phe Lys Ile His Val Leu
        195                 200                 205

Gly Phe Arg Pro Lys Lys Glu Lys Asp Gly Ser Ser Thr Glu Met
    210                 215                 220

Gln Leu Thr Ala Ile Phe Lys Arg His Ser Ala Glu Ala Lys Ser Pro
225                 230                 235                 240

Ala Ser Asp Leu Leu Ser Phe Asp Ser Asn Lys Ile Glu Ser Glu Glu
                245                 250                 255
```

```
Val Tyr His Gly Thr Met Glu Glu Asp Lys Gln Pro Glu Ile Tyr Leu
            260                 265                 270

Thr Ala Thr Asp Leu Lys Arg Leu Ile Ser Lys Ala Leu Glu Glu Glu
        275                 280                 285

Gln Ser Leu Asp Val Gly Thr Ile Gln Phe Thr Asp Glu Ile Ala Gly
        290                 295                 300

Ser Leu Pro Ala Phe Gly Pro Asp Thr Gln Ser Glu Leu Pro Thr Ser
305                 310                 315                 320

Phe Ala Val Ile Thr Glu Asp Ala Thr Leu Ser Pro Glu Leu Pro Pro
                325                 330                 335

Val Glu Pro Gln Leu Glu Thr Val Asp Gly Ala Glu His Gly Leu Pro
                340                 345                 350

Asp Thr Ser Trp Ser Pro Pro Ala Met Ala Ser Thr Ser Leu Ser Glu
            355                 360                 365

Ala Pro Pro Phe Phe Met Ala Ser Ser Ile Phe Ser Leu Thr Asp Gln
370                 375                 380

Gly Thr Thr Asp Thr Met Ala Thr Asp Gln Thr Met Leu Val Pro Gly
385                 390                 395                 400

Leu Thr Ile Pro Thr Ser Asp Tyr Ser Ala Ile Ser Gln Leu Ala Leu
                405                 410                 415

Gly Ile Ser His Pro Pro Ala Ser Ser Asp Asp Ser Arg Ser Ser Ala
            420                 425                 430

Gly Gly Glu Asp Met Val Arg His Leu Asp Glu Met Asp Leu Ser Asp
        435                 440                 445

Thr Pro Ala Pro Ser Glu Val Pro Gly Leu Ser Glu Tyr Val Ser Val
    450                 455                 460

Pro Asp His Phe Leu Glu Asp Thr Thr Pro Val Ser Ala Leu Gln Tyr
465                 470                 475                 480

Ile Thr Thr Ser Ser Met Thr Ile Ala Pro Lys Gly Arg Glu Leu Val
                485                 490                 495

Val Phe Phe Ser Leu Arg Val Ala Asn Met Ala Phe Ser Asn Asp Leu
            500                 505                 510

Phe Asn Lys Ser Ser Leu Glu Tyr Arg Ala Leu Glu Gln Gln Phe Thr
        515                 520                 525

Gln Leu Leu Val Pro Tyr Leu Arg Ser Asn Leu Thr Gly Phe Lys Gln
530                 535                 540

Leu Glu Ile Leu Asn Phe Arg Asn Gly Ser Val Ile Val Asn Ser Lys
545                 550                 555                 560

Met Lys Phe Ala Lys Ser Val Pro Tyr Asn Leu Thr Lys Ala Val His
                565                 570                 575

Gly Val Leu Glu Asp Phe Arg Ser Ala Ala Gln Gln Leu His Leu
            580                 585                 590

Glu Ile Asp Ser Tyr Ser Leu Asn Ile Glu Pro Ala Asp Gln Ala Asp
        595                 600                 605

Pro Cys Lys Phe Leu Ala Cys Gly Glu Phe Ala Gln Cys Val Lys Asn
    610                 615                 620

Glu Arg Thr Glu Glu Ala Glu Cys Arg Cys Lys Pro Gly Tyr Asp Ser
625                 630                 635                 640

Gln Gly Ser Leu Asp Gly Leu Glu Pro Gly Leu Cys Gly Pro Gly Thr
                645                 650                 655

Lys Glu Cys Glu Val Leu Gln Gly Lys Gly Ala Pro Cys Arg Leu Pro
            660                 665                 670

Asp His Ser Glu Asn Gln Ala Tyr Lys Thr Ser Val Lys Lys Phe Gln
```

-continued

```
                 675                 680                 685
Asn Gln Gln Asn Asn Lys Val Ile Ser Lys Arg Asn Ser Glu Leu Leu
        690                 695                 700

Thr Val Glu Tyr Glu Glu Phe Asn His Gln Asp Trp Glu Gly Asn
705                 710                 715

<210> SEQ ID NO 5
<211> LENGTH: 2244
<212> TYPE: DNA
<213> ORGANISM: Homo sapiens
<220> FEATURE:
<223> OTHER INFORMATION: Human IPM 150 cDNA sequence, isoform C
<220> FEATURE:
<221> NAME/KEY: misc_feature
<222> LOCATION: (1)..(2244)
<223> OTHER INFORMATION: n is a, c, g, or t.

<400> SEQUENCE: 5
aaattaacac cctcataaag gtaaaccaag aaggttatcc tcaatcatct ggtatcaata      60
tataattatt tttcacattt ctgttacttt ttaatgagat ttgaggttgt ctgtgattgt     120
tatcagaatt accaatgcac aaaagccaga atgtatttgg aaactagaag agctattttt     180
gttttttgga tttttctcca agttcaagga accaaagata tctccattaa catataccat     240
tctgaaacta aagacataga caatnccccca agaaatgaaa caactgaaag tactgaaaaa    300
atgtacaaaa tgtcaactat gagacgaata ttcgatttgg caaagnatcg aacaaaaaga     360
tccgcatttt tcccaacggg ggttaaagtc tgtccacagg aatccatgaa acagattttta    420 gacagtcttc aagcttatta tagattgaga gtgtgtcagg aagcagcatg ggaagcatat     480
cggatctttc tggatcgcat ccctgacaca ggggaatatc aggactgggt cagcatctgc     540
cagcaggaga ccttctgcct ctttgacatt ggaaaaaact tcagcaattc ccaggagcac     600
ctggatcttc tccagcagag aataaaacag agaagtttcc ctgacagaaa agatgaaata     660
tctgcagaga agacattggg agagcctggt gaaaccattg tcatttcaac agcaatctac     720
atttcaaaga cttgggcagt attctaagaa acccctcaga gagcaaatt caagatgttg      780 ccaacgtctc acttgggcct ttccctctca ctcctgatga caccctcctc aatggaattc     840
tcgataatac actcaacgac accaagatgc tacaacaga aagagaaaca gaattcgctg      900
tgttggagga gcagagggtg gagctcagcg tctctctggt aaaccagaag ttcaaggcag     960
agctcgctga ctcccagtcc ccatattacc aggagctagc aggaaagtcc caacttcaga    1020
tgcaaaagat atttaagaaa cttccaggat tcaaaaaaat ccatgtgtta ggatttagac    1080
caaagaaaga aaaagatggc tcaagctcca cagagatgca acttacggcc atcttttaaga   1140 gacacagtgc agaagcaaaa agccctgcaa gtgacctcct gtcttttgat tccaacaaaa    1200
ttgaaagtga ggaagtctat catggaacca tggaggagga caagcaacca gaaatctatc    1260
tcacagctac agacctcaaa aggctgatca gcaaagcact agaggaagaa caatctttgg    1320
atgtggggac aattcagttc actgatgaaa ttgctggatc actgccagcc tttggtcctg    1380
acacccaatc agagctgccc acatcttttg ctgttataac agaggatgct actttgagtc    1440
cagaacttcc tcctgttgaa ccccagcttg agacagtgga cggagcagag catggtctac    1500
ctgacacttt tggtctcca cctgctatgg ccctacctcc ctgtcagaag ctccaccttt     1560
ctttatggca tcaagcatct tctctctgac tgatcaaggc accacagata caatggccac    1620
tgaccagaca atgctagtac cagggctcac catccccacc agtgattatt ctgcaatcag    1680
ccaactggct ctgggaattt cacatccacc tgcatcttca gatgacagcc gatcaagtgc    1740
```

```
aggtggcgaa ggtatggaca gagacctaga tgaaatggat ctgtctgaca ctcctgcccc    1800
atctgaggta ccagagctca gcgaatatgt ttctgtccca gatcatttct tggaggatac    1860
cactcctgtc tcagctttac agtatatcac cactagttct atgaccattg cccccaaggg    1920
ccgagagctg gtagtgttct tcagtctgcg tgttgctaac atggccttct ccaacgacct    1980
gttcaacaag agctatttgg agtaccgagc tctggagcaa caattcacac agctgctggt    2040
tccatatcta cgatccaatc ttacaggatt taagcaactt gaaatactta acttcagaaa    2100
cgggagtgtg attgtgaata gcaaaatgaa gtttgctaag tcagtgccgt ataacctcac    2160
caaggctgtg cacggggtct tggaggattt tcgttctgct gcagcccaac aactccatct    2220
ggaaatagac agctactctc tccc                                           2244
```

<210> SEQ ID NO 6
<211> LENGTH: 198
<212> TYPE: PRT
<213> ORGANISM: Homo sapiens
<220> FEATURE:
<223> OTHER INFORMATION: Human IPM 150 amino acid sequence, isoform C

<400> SEQUENCE: 6

```
Met Tyr Leu Glu Thr Arg Arg Ala Ile Phe Val Phe Trp Ile Phe Leu
  1               5                  10                  15

Gln Val Gln Gly Thr Lys Asp Ile Ser Ile Asn Ile Tyr His Ser Glu
             20                  25                  30

Thr Lys Asp Ile Asp Asn Pro Pro Arg Asn Glu Thr Thr Glu Ser Thr
         35                  40                  45

Glu Lys Met Tyr Lys Met Ser Thr Met Arg Arg Ile Phe Asp Leu Ala
     50                  55                  60

Lys His Arg Thr Lys Arg Ser Ala Phe Phe Pro Thr Gly Val Lys Val
 65                  70                  75                  80

Cys Pro Gln Glu Ser Met Lys Gln Ile Leu Asp Ser Leu Gln Ala Tyr
                 85                  90                  95

Tyr Arg Leu Arg Val Cys Gln Glu Ala Ala Trp Glu Ala Tyr Arg Ile
            100                 105                 110

Phe Leu Asp Arg Ile Pro Asp Thr Gly Glu Tyr Gln Asp Trp Val Ser
        115                 120                 125

Ile Cys Gln Gln Glu Thr Phe Cys Leu Phe Asp Ile Gly Lys Asn Phe
    130                 135                 140

Ser Asn Ser Gln Glu His Leu Asp Leu Leu Gln Gln Arg Ile Lys Gln
145                 150                 155                 160

Arg Ser Phe Pro Asp Arg Lys Asp Glu Ile Ser Ala Glu Lys Thr Leu
                165                 170                 175

Gly Glu Pro Gly Glu Thr Ile Val Ile Ser Thr Ala Ile Tyr Ile Ser
            180                 185                 190

Lys Thr Trp Ala Val Phe
        195
```

<210> SEQ ID NO 7
<211> LENGTH: 1858
<212> TYPE: DNA
<213> ORGANISM: Homo sapiens
<220> FEATURE:
<223> OTHER INFORMATION: Human IMPG1 gene, regulatory region
<220> FEATURE:
<221> NAME/KEY: misc_feature
<222> LOCATION: (1)..(1858)
<223> OTHER INFORMATION: n is a, c, g, or t.

<400> SEQUENCE: 7

```
agggtgtagg cttttgaacc aggactcttt aggtttaaat cctagctctg ccacatatac      60
tttattctcc tcaaatttaa aagagatagt attaacagtg tttatattgt catattgagg     120
aatctatgga taatctatgg acatctctaa gaacaatgtc tatccacaac acaagagctc     180
aatatacagt agtagttgca gtgtgtttca tgactcagca atatgtagca tgtatagtca     240
aaataatata aaatcaaata ttcaaaaact gaaattacaa taatactgat gaagaaagat     300
ggaaagatgt ttacaatgag tagaaagggt atgtgtggaa gtgaagttat tctcaatatc     360
tattatttga taatacctaa aagtgaaaac ctccaaaata gtaatagagg catgttattt     420
agaagtgcaa atgagactac tagaagaatt aggttgatga agtaaaaatg gctcccctttt    480
gaaagaaggc atgggtagaa gaaaggcaca attttttctt acaaactttg tagaaaaaaa     540
gtatttgacc ccttaaacac agtgcataca gattttaaac attaaaacca gacttaaatc     600
aaaaaagcca cctgtatgta attccaaatc aaaagcaatt tataaagcag aacatagaag     660
agaatggaga cagtttcgct atctgtggag actaatacat attggataac catatacttt     720
cagggacaga aattaagctc ttttaatgga tgtttcttgt acatgtcatt ttagaaaaca     780
tctgacccta actgtcagcc ttattctctg tttggcagaa cttcccctgg ctctctgtgt     840
cactgtaaca ggtgaataac taagaaaaaa ctgtgtctgt agacacttgt ttataatggc     900
attcagggtc ctggagctag gctgacagat gctcctccag aaggttaatg agataaaggt     960
tcctccagct ggcccttaag cagagattac acctgaggga aagacaagca gattattcca    1020
gaaacagaca ctgctacatg ttcttcataa attaacaccc tcataaaggt aaaccaagaa    1080
ggttatcctc aatcatctgg tatcaatata taattatttt tcacatttct gttactttt     1140
aatgagattt gaggttgttc tgtgattgtt atcagaatta ccaatgcaca aaagccagaa    1200
tgtatttgga aactagaaga gctatttttg ttttttggat ttttctccaa gttcaaggaa    1260
ccaaaggtaa gttacttaaa tgtttacttt taaattgctt atctataaaa tctaccgata    1320
gaagtgaata tttagaacca acaaggctac caatttatct cacgggctag tatatagtag    1380
gccttgaata atatattgctt gattgattga ataattaact atcagaaatg attttcactt    1440
gatttaatat ttactacatg gtcttaagtg cagtgaagat taacaaaata ggagagatga    1500
atgcatccta tttgctgttc taaaacattc attgaaaatt cttattatta aatgtaaata    1560
ntattagtag atctggtgaa aactaaactc catttatcca cccgaaattc aaccaaataa    1620
aacctaaagg ataaaagtaa tgttttaagt catttatggt cagacaaaaa aaagtaagta    1680
tttcttacct tctcacaatg aaatcatgag ttgctttccc ttagaaaata gcaaacattc    1740
ttcatcttca gggttcatga tgacaaccac ttcaaaattt ggttgttttt gaaagttgta    1800
cgcataaaag aactaggcaa tgtatgttct tatggcaaat ctgcatctga atatgaaa     1858
```

<210> SEQ ID NO 8
<211> LENGTH: 3668
<212> TYPE: DNA
<213> ORGANISM: Mus sp.
<220> FEATURE:
<223> OTHER INFORMATION: Mouse IPM 150 cDNA sequence, isoform A
<220> FEATURE:
<221> NAME/KEY: misc_feature
<222> LOCATION: (1)..(3668)
<223> OTHER INFORMATION: n is a, c, g, or t.

<400> SEQUENCE: 8

-continued

```
acaagattat tccaggaact gacctgcttc cggatcctcg agaattagca ccttcatagg      60
gtaaaccagg gaggtcgtct gtactcagcc ggcacctgga tttgattatt tttcatattt     120
cagtcacctt atttctttaa gtgtgacttg gtattgttct gtgattttc agaattacca      180
gtatacagaa ccagaatgaa ttttcaaatt aaacatgcta tctttgtttt tgggattttt     240
ctccaagttc aaggaatcaa agatacctct attaaaatat tcagttctga aattaaaaac     300
atagacaaaa ccccaagaat cgaaacaatt gaaagtactt caacagtgca caaagtgtca     360
accatgaaac gaatattcga tttgccaaag cttcgaacca aaagatcagc acttttccca     420
gctgctaaca tctgtccaca ggaatccttg agacagattt tagcaagtct tcaagaatat     480
tatagactga gagtatgtca agaagtcgtg tgggaagcat atcgtatctt tctggaccga     540
attcctgaca cagaggaata tcaagactgg gtcagcctct gccagaaaga aaccttctgc     600
ctctttgaca ttgggaaaaa cttcagcaac tcccaggagc acctagatct tcttcagcag     660
agaataaaac agagaagctt ccctgggagg aaagatgaga cagcctccat ggagacactg     720
gaagcaccta ctgaagcccc tgtggtaccc acagatgttt ccaggatgtc cctggggccc     780
ttcccacttc cttctgatga cacagacctc aaggagattc tcagtgtcac cctcaaggac     840
attcaaaagc ccacaacaga aagtaaaaca gaacctattc acgtgtctga attctcatca     900
gaggagaagg tggaattcag catctctctg ccaaaccaca ggttcaaggc agagctcacc     960
aactctgggt caccatacta ccaggaactg gtgggacagt cccaactgca gttgcaaaag    1020
atatttaaga aacttccagg attcggagaa atccgtgtat taggatttag accaaagaaa    1080
gaagaagatg gttcaagctc cacagaaata cagcttatgg ccatctttaa gagggaccat    1140
gcagaagcaa aaagccctga tagtcatcta ctgtctcttg attccaacaa aattgaaagt    1200
gaaagaatcc atcatggagt catagaagac aaacaaccag aaacctacct cacagctaca    1260
gacctcaaaa aactcatcat acaactacta gatggagacc tgtccttggt agaagggaaa    1320
attccattcg gtgatgaagt tactgggaca ctcttcagac ctgtcactga accagatctg    1380
cccaagcccc ttgctgatgt cacagaggat gccactttga gtccagaact tcctttcgtt    1440
gagcctaggc ttgaggcagt ggacagagaa ggatctgagc tgcctggaat gtcctccaaa    1500
gacagttctt ggtctccacc tgtatcagcc tcaatttccc gatcagaaaa tctaccttcg    1560
tttacaccta gcatcttctc tctagatgct caaagcccc ctccccttgat gaccactggc    1620
ccaacagcac tcatccccaa gcccactctc cccactatcg attattctac catccgccaa    1680
ttgcctctgg aatcgtcaca ttggcctgca tcctccagtg acagagagct gatcacaagc    1740
agccatgaca caatccgaga cctagatggc atggatgtgt ctgacacgcc agccttgtca    1800
gaaatatcag aactgagtgg atacgattct gcctcgggtc agttcttgga gatgaccaca    1860
cccatcccaa cagtacggtt catcaccacc agctccgaga ccattgccac caagggccag    1920
gagctagtgg tattcttcag cctgcgtgtt gctaacatgc gttctcccta tgacctgttc    1980
aacaagagtt ctctggagta tcaagccctg aacaacgat tcacagacct gctggttccc    2040
tatctacgat cgaatcttac gggatttaag caactgaaa tactcagctt cagaaacgga    2100
agtgtgatcg tgaacagcaa agtgcggttt gcaaaggcgg taccctacaa cctcacccag    2160
gccgtgcgcg gggtcttgga ggatcttcgg tccaccgcag ctcaagggct caatctggaa    2220
atcgaaagct actccctcga cattgaacca gctgatcagg cggatccctg caaactccta    2280
gactgtggca aatttgccca gtgtgtaaag aatgagtgga cagaggaagc agagtgtcgc    2340
tgcagacagg gacatgagag ccacgggacc ctggactacc agaccctgaa cctctgtccc    2400
```

```
cctggaaaga cttgtgtggc cggccgagaa caagcaactc catgcaggcc accagatcac    2460
tctacaaacc aagctcagga acctggtgtt aaaaagctac gtcagcaaaa taaggtagtc    2520
aagaaaagaa attctaaact atcagctata ggatttgaag aatttgaaga ccaggactgg    2580
gagggaaatt aaaagctgga atcatatgca ttatgttgca aactctgttg aaaggaaact    2640
ttatttctta aagaaaggtg tatctgttct gttaacttct gaaaaacaga gggagagatt    2700
cagtggtcat tggaatacag gcatgtaatc aactttgaga ctcagcatgc ttgaacaaga    2760
gcacaggcgt gtatttgatg acagttaagc ctggttgggg cggggggcac atatttttag    2820
tcaaaactca aagcaatcat tggaacacat ttgactattt ttggacagta ctcaagtagc    2880
aaagataagg ttagcttttt tctttcttta aattattaca taaarcttat ttcaaataaa    2940
tacaacttgt ttagtgggtt gtacaatatt gaggatctga ttcttttata tgttagaata    3000
tacagttaaa agattatcat ttgggccaga gagatagcta agtggttaag agtatatact    3060
gctcttccag aagccctggg tttaccgtcc aacagccac attgactggc tcacacacac    3120
ctgtaagtca ggctccagag aacaaacacc ctcctctggc ctttgtaccc acgtgcacat    3180
aaccgcaaac agacacaccc acgctatttt tttagaagtc attgattttt ttaattaggg    3240
gtggaaaakc aggctggaga gatgactccg tggttaagaa cagttgttgt tcttccagag    3300
gacccaggtt cagttcccag aacccacaag gcnagtctcc caactattca taattctagt    3360
tcaagtggat ccagcaccct cttctaactg atactgccag taccaggcag ccatgtggtg    3420
catatgcatt tgggcaggta aaacactcag acacgcaaaa aattttaaat ctaaattttg    3480
aaaatatttt agttttaagg atgatcactg tgtgagggtc aggtctctta tgtatgaatg    3540
tagtaccaag aactgtgatg agtatatgta tgctccattc tatagtctcc tctctctctc    3600
tctctctctc tctctctctc tctctctctc tctctggaat tccggaattc cggaattccg    3660
gaattccg                                                             3668
```

<210> SEQ ID NO 9
<211> LENGTH: 798
<212> TYPE: PRT
<213> ORGANISM: Mus sp.
<220> FEATURE:
<223> OTHER INFORMATION: Mouse IPM 150 amino acid sequence, isoform A

<400> SEQUENCE: 9

```
Met Asn Phe Gln Ile Lys His Ala Ile Phe Val Phe Gly Ile Phe Leu
  1               5                  10                  15

Gln Val Gln Gly Ile Lys Asp Thr Ser Ile Lys Ile Phe Ser Ser Glu
             20                  25                  30

Ile Lys Asn Ile Asp Lys Thr Pro Arg Ile Glu Thr Ile Glu Ser Thr
         35                  40                  45

Ser Thr Val His Lys Val Ser Thr Met Lys Arg Ile Phe Asp Leu Pro
     50                  55                  60

Lys Leu Arg Thr Lys Arg Ser Ala Leu Phe Pro Ala Ala Asn Ile Cys
 65                  70                  75                  80

Pro Gln Glu Ser Leu Arg Gln Ile Leu Ala Ser Leu Gln Glu Tyr Tyr
                 85                  90                  95

Arg Leu Arg Val Cys Gln Glu Val Val Trp Glu Ala Tyr Arg Ile Phe
            100                 105                 110

Leu Asp Arg Ile Pro Asp Thr Glu Glu Tyr Gln Asp Trp Val Ser Leu
        115                 120                 125
```

```
Cys Gln Lys Glu Thr Phe Cys Leu Phe Asp Ile Gly Lys Asn Phe Ser
130                 135                 140

Asn Ser Gln Glu His Leu Asp Leu Leu Gln Gln Arg Ile Lys Gln Arg
145                 150                 155                 160

Ser Phe Pro Gly Arg Lys Asp Glu Thr Ala Ser Met Glu Thr Leu Glu
                165                 170                 175

Ala Pro Thr Glu Ala Pro Val Val Pro Thr Asp Val Ser Arg Met Ser
            180                 185                 190

Leu Gly Pro Phe Pro Leu Pro Ser Asp Thr Asp Leu Lys Glu Ile
        195                 200                 205

Leu Ser Val Thr Leu Lys Asp Ile Gln Lys Pro Thr Thr Glu Ser Lys
210                 215                 220

Thr Glu Pro Ile His Val Ser Glu Phe Ser Glu Glu Lys Val Glu
225                 230                 235                 240

Phe Ser Ile Ser Leu Pro Asn His Arg Phe Lys Ala Glu Leu Thr Asn
                245                 250                 255

Ser Gly Ser Pro Tyr Tyr Gln Glu Leu Val Gly Gln Ser Gln Leu Gln
                260                 265                 270

Leu Gln Lys Ile Phe Lys Lys Leu Pro Gly Phe Gly Glu Ile Arg Val
        275                 280                 285

Leu Gly Phe Arg Pro Lys Lys Glu Glu Asp Gly Ser Ser Ser Thr Glu
        290                 295                 300

Ile Gln Leu Met Ala Ile Phe Lys Arg Asp His Ala Glu Ala Lys Ser
305                 310                 315                 320

Pro Asp Ser His Leu Leu Ser Leu Asp Ser Asn Lys Ile Glu Ser Glu
                325                 330                 335

Arg Ile His His Gly Val Ile Glu Asp Lys Gln Pro Glu Thr Tyr Leu
                340                 345                 350

Thr Ala Thr Asp Leu Lys Lys Leu Ile Ile Gln Leu Leu Asp Gly Asp
            355                 360                 365

Leu Ser Leu Val Glu Gly Lys Ile Pro Phe Gly Asp Glu Val Thr Gly
        370                 375                 380

Thr Leu Phe Arg Pro Val Thr Glu Pro Asp Leu Pro Lys Pro Leu Ala
385                 390                 395                 400

Asp Val Thr Glu Asp Ala Thr Leu Ser Pro Glu Leu Pro Phe Val Glu
                405                 410                 415

Pro Arg Leu Glu Ala Val Asp Arg Glu Gly Ser Glu Leu Pro Gly Met
            420                 425                 430

Ser Ser Lys Asp Ser Ser Trp Ser Pro Val Ser Ala Ser Ile Ser
        435                 440                 445

Arg Ser Glu Asn Leu Pro Ser Phe Thr Pro Ser Ile Phe Ser Leu Asp
        450                 455                 460

Ala Gln Ser Pro Pro Leu Met Thr Thr Gly Pro Thr Ala Leu Ile
465                 470                 475                 480

Pro Lys Pro Thr Leu Pro Thr Ile Asp Tyr Ser Thr Ile Arg Gln Leu
                485                 490                 495

Pro Leu Glu Ser Ser His Trp Pro Ala Ser Ser Ser Asp Arg Glu Leu
                500                 505                 510

Ile Thr Ser Ser His Asp Thr Ile Arg Asp Leu Asp Gly Met Asp Val
        515                 520                 525

Ser Asp Thr Pro Ala Leu Ser Glu Ile Ser Glu Leu Ser Gly Tyr Asp
530                 535                 540

Ser Ala Ser Gly Gln Phe Leu Glu Met Thr Thr Pro Ile Pro Thr Val
```

```
                545                 550                 555                 560
Arg Phe Ile Thr Thr Ser Ser Glu Thr Ile Ala Thr Lys Gly Gln Glu
                    565                 570                 575
Leu Val Val Phe Phe Ser Leu Arg Val Ala Asn Met Pro Phe Ser Tyr
                580                 585                 590
Asp Leu Phe Asn Lys Ser Ser Leu Glu Tyr Gln Ala Leu Glu Gln Arg
            595                 600                 605
Phe Thr Asp Leu Leu Val Pro Tyr Leu Arg Ser Asn Leu Thr Gly Phe
        610                 615                 620
Lys Gln Leu Glu Ile Leu Ser Phe Arg Asn Gly Ser Val Ile Val Asn
625                 630                 635                 640
Ser Lys Val Arg Phe Ala Lys Ala Val Pro Tyr Asn Leu Thr Gln Ala
                645                 650                 655
Val Arg Gly Val Leu Glu Asp Leu Arg Ser Thr Ala Ala Gln Gly Leu
                660                 665                 670
Asn Leu Glu Ile Glu Ser Tyr Ser Leu Asp Ile Glu Pro Ala Asp Gln
            675                 680                 685
Ala Asp Pro Cys Lys Leu Leu Asp Cys Gly Lys Phe Ala Gln Cys Val
        690                 695                 700
Lys Asn Glu Trp Thr Glu Glu Ala Glu Cys Arg Cys Arg Gln Gly His
705                 710                 715                 720
Glu Ser His Gly Thr Leu Asp Tyr Gln Thr Leu Asn Leu Cys Pro Pro
                725                 730                 735
Gly Lys Thr Cys Val Ala Gly Arg Glu Gln Ala Thr Pro Cys Arg Pro
                740                 745                 750
Pro Asp His Ser Thr Asn Gln Ala Gln Glu Pro Gly Val Lys Lys Leu
            755                 760                 765
Arg Gln Gln Asn Lys Val Val Lys Lys Arg Asn Ser Lys Leu Ser Ala
        770                 775                 780
Ile Gly Phe Glu Glu Phe Glu Asp Gln Asp Trp Glu Gly Asn
785                 790                 795

<210> SEQ ID NO 10
<211> LENGTH: 1726
<212> TYPE: DNA
<213> ORGANISM: Mus sp.
<220> FEATURE:
<223> OTHER INFORMATION: Mouse IPM 150 cDNA sequence, isoform D

<400> SEQUENCE: 10
ggctttaaac cagggaggtc gtctgtactc agccggcacc tggatttgat tattttcat      60
atttcagtca ccttatttct ttaagtgtga cttggtattg ttctgtgatt tttcagaatt    120
accagtatac agaaccagaa tgaattttca aattaaacat gctatctttg tttttgggat    180
ttttctccaa gttcaaggaa tcaaagtatg tcaagaagtc gtgtgggaag catatcgtat    240
ctttctggac cgaattcctg acacagagga atatcaagac tgggtcagcc tctgccagaa    300
agaaaccttc tgcctctttg acattgggaa aaacttcagc aactcccagg agcacctaga    360
tcttcttcag cagagaataa aacagagaag cttccctggg aggaaagatg agacagcctc    420
catggagaca ctggaagcac ctactgaagc ccctgtggta cccacagatg tttccaggat    480
gtccctgggg ccattcccac ttccttctga tgacacagac ctcaaggaga ttctcagtgt    540
caccctcaag gacattcaaa agcccacaac agaaagtata acagaaccta ttcacgtgtc    600
tgaattctca tcagaggaga aggtggagtt cagcatctct ctgccaaacc acaggttcaa    660
```

-continued

```
ggcagagctc accaactctg ggtcaccata ctaccaggaa ctggtgggac agtcccaact    720
gcagttgcaa aagatattta agaaacttcc aggattcgga gaaatccgtg tattaggatt    780
tagaccaaag aaagaagaag atggttcaag ctccacagaa atacagctta tggccatctt    840
taagagggac catgcagaag caaaaagccc tgatagtcat ctactgtctc ttgattccaa    900
caaaattgaa agtgaaagaa tccatcatgg agtcatagaa acaaacaac cagaaaccta    960
cctcacagct acagacctca aaaaactcat catacaacta ctagatggag acctgtcctt   1020
ggtagaaggg aaaattccat tcggtgatga agttactggg acactcttca gacctgtcac   1080
tgaaccagat ctgcccaagc cccttgctga tgtcacagag gatgccactt tgagtccaga   1140
acttcctttc gttgagccta ggcttgaggc agtggacaga aaggatctg agctgcctgc   1200
tgatcaggcg gatccctgca aacttctaga ctgtggcaaa tttgcccagt gtgtaaagaa   1260
tgagtggaca gaggaagcag agtgtcgctg cagacaggga catgagagcc acgggaccct   1320
ggactaccag accctgaacc tctgtccccc tggaaagact tgtgtggccg ccgagaaca   1380
agcaactcca tgcaggccaa cagatcactc tacaaaccaa gctcaggaac ctggtgttaa   1440
aaagctacgt cagcaaaata aggtagtcaa gaaaagaaat tctaaactat cagctatagg   1500
atttgaagaa tttgaagacc aggactggga gggaaattaa agctggaat catatgcatt   1560
atgttgcaaa ctctgttgaa aggaaacttt atttcttaaa gaaaggtgta tctgttctgt   1620
taacttctga aaaacagagg gagagattca gtggtcattg gaatacaggc atgtaatcaa   1680
ctttgagact cagcatgctt gaacaagagc acaggcgtgt atttga               1726
```

<210> SEQ ID NO 11
<211> LENGTH: 466
<212> TYPE: PRT
<213> ORGANISM: Mus sp.
<220> FEATURE:
<223> OTHER INFORMATION: Mouse IPM 150 amino acid sequence, isoform D

<400> SEQUENCE: 11

```
Met Asn Phe Gln Ile Lys His Ala Ile Phe Val Phe Gly Ile Phe Leu
  1               5                  10                  15

Gln Val Gln Gly Ile Lys Val Cys Gln Glu Val Val Trp Glu Ala Tyr
             20                  25                  30

Arg Ile Phe Leu Asp Arg Ile Pro Asp Thr Glu Glu Tyr Gln Asp Trp
         35                  40                  45

Val Ser Leu Cys Gln Lys Glu Thr Phe Cys Leu Phe Asp Ile Gly Lys
     50                  55                  60

Asn Phe Ser Asn Ser Gln Glu His Leu Asp Leu Leu Gln Gln Arg Ile
 65                  70                  75                  80

Lys Gln Arg Ser Phe Pro Gly Arg Lys Asp Glu Thr Ala Ser Met Glu
                 85                  90                  95

Thr Leu Glu Ala Pro Thr Glu Ala Pro Val Val Pro Thr Asp Val Ser
            100                 105                 110

Arg Met Ser Leu Gly Pro Phe Pro Leu Pro Ser Asp Asp Thr Asp Leu
        115                 120                 125

Lys Glu Ile Leu Ser Val Thr Leu Lys Asp Ile Gln Lys Pro Thr Thr
    130                 135                 140

Glu Ser Ile Thr Glu Pro Ile His Val Ser Phe Ser Ser Glu Glu
145                 150                 155                 160

Lys Val Glu Phe Ser Ile Ser Leu Pro Asn His Arg Phe Lys Ala Glu
                165                 170                 175
```

-continued

```
Leu Thr Asn Ser Gly Ser Pro Tyr Tyr Gln Glu Leu Val Gly Gln Ser
            180                 185                 190
Gln Leu Gln Leu Gln Lys Ile Phe Lys Lys Leu Pro Gly Phe Gly Glu
        195                 200                 205
Ile Arg Val Leu Gly Phe Arg Pro Lys Lys Glu Asp Gly Ser Ser
    210                 215                 220
Ser Thr Glu Ile Gln Leu Met Ala Ile Phe Lys Arg Asp His Ala Glu
225                 230                 235                 240
Ala Lys Ser Pro Asp Ser His Leu Leu Ser Leu Asp Ser Asn Lys Ile
                245                 250                 255
Glu Ser Glu Arg Ile His His Gly Val Ile Glu Asp Lys Gln Pro Glu
            260                 265                 270
Thr Tyr Leu Thr Ala Thr Asp Leu Lys Lys Leu Ile Ile Gln Leu Leu
        275                 280                 285
Asp Gly Asp Leu Ser Leu Val Glu Gly Lys Ile Pro Phe Gly Asp Glu
    290                 295                 300
Val Thr Gly Thr Leu Phe Arg Pro Val Thr Glu Pro Asp Leu Pro Lys
305                 310                 315                 320
Pro Leu Ala Asp Val Thr Glu Asp Ala Thr Leu Ser Pro Glu Leu Pro
                325                 330                 335
Phe Val Glu Pro Arg Leu Glu Ala Val Asp Arg Glu Gly Ser Glu Leu
            340                 345                 350
Pro Ala Asp Gln Ala Asp Pro Cys Lys Leu Leu Asp Cys Gly Lys Phe
        355                 360                 365
Ala Gln Cys Val Lys Asn Glu Trp Thr Glu Glu Ala Glu Cys Arg Cys
    370                 375                 380
Arg Gln Gly His Glu Ser His Gly Thr Leu Asp Tyr Gln Thr Leu Asn
385                 390                 395                 400
Leu Cys Pro Pro Gly Lys Thr Cys Val Ala Gly Arg Glu Gln Ala Thr
                405                 410                 415
Pro Cys Arg Pro Thr Asp His Ser Thr Asn Gln Ala Gln Glu Pro Gly
            420                 425                 430
Val Lys Lys Leu Arg Gln Gln Asn Lys Val Val Lys Arg Asn Ser
        435                 440                 445
Lys Leu Ser Ala Ile Gly Phe Glu Glu Phe Glu Asp Gln Asp Trp Glu
    450                 455                 460
Gly Asn
465
```

<210> SEQ ID NO 12
<211> LENGTH: 1321
<212> TYPE: DNA
<213> ORGANISM: Mus sp.
<220> FEATURE:
<223> OTHER INFORMATION: Mouse IPM 150 cDNA sequence, isoform E

<400> SEQUENCE: 12

| | | | | |
|---|---|---|---|---|
| tctgcagaat tcggcttaac cagggaggtc gtctgtactc agccggcacc tggatttgat | | | | 60 |
| tattttcat atttcagtca ccttatttct ttaagtgtga cttggtattg ttctgtgatt | | | | 120 |
| tttcagaatt accagtatac agaaccagaa tgaatttca aattaaacat gctatctttg | | | | 180 |
| tttttgggat tttctccaa gttcaaggaa tcaaagatac ctctattaaa atattcagtt | | | | 240 |
| ctgaaattaa aaacatagac aaaaccccaa gaatcgaaac aattgaaagt acttcaacag | | | | 300 |
| tgcacaaagt gtcaaccatg aaacgccagc cttgtcagaa atatcagaac tgagtggata | | | | 360 |

```
cgattctgcc tcgggtcagt tcttggagat gaccacaccc atcccaacag tacggttcat    420
caccaccagc tccgagacca ttgccaccaa gggccaggag ctagtggtat tcttcagcct    480
gcgtgttgtt aacatgccgt tctcctatga cctgttcaac aagagttctc tggagtatca    540
agccctggaa caacgattca cagacctgct ggttccctat cwacgatcga atcttacggg    600
atttaagcaa ctggaaatac tcagcttcag aaacggaagt gtgatcgtga acagcaaagt    660
gcggtttgca aaggcggtac cctacaacct cacccaggcc gtgcgcgggg tcttggagga    720
tcttcggtcc accgcagctc aagggctcaa tctggaaatc gaaagctact ccctcgacat    780
tgaaccagct gatcaggcgg atccctgcaa acttctagac tgtggcaaat ttgcccagtg    840
tgtaaagaat gagtggacag aggaagcaga gtgtcgctgc agacagggac atgagagcca    900
cgggaccctg gactaccaga ccctgaacct ctgtccccct ggaaagactt gtgtggccgg    960
ccgagaacaa gcaactccat gcaggccacc agatcactct acaaaccaag ctcaggaacc   1020
tggtgttaaa aagctacgtc agcaaaataa ggtagtcaag aaacgaaatt ctaaactatc   1080
agctatagga tttgaaaaat ttgaagacca ggactgggag ggaaattaaa agctggaatc   1140
atatgcatta tgttgcaaac tctgttgaaa ggaaacttta tttcttaaag aaaggtgtat   1200
ctgttctgtt aacttctgaa aaacagaggg agagattcag tggtcattgg aatacaggca   1260
tgtaatcaac tttgagactc agcatgcttg aacaagagca caggcgtgta tttgataagc   1320
c                                                                   1321

<210> SEQ ID NO 13
<211> LENGTH: 67
<212> TYPE: PRT
<213> ORGANISM: Mus sp.
<220> FEATURE:
<223> OTHER INFORMATION: Mouse IPM 150 amino acid sequence, isoform E

<400> SEQUENCE: 13

Met Asn Phe Gln Ile Lys His Ala Ile Phe Val Gly Ile Phe Leu
  1               5                  10                  15

Gln Val Gln Gly Ile Lys Asp Thr Ser Ile Lys Ile Phe Ser Ser Glu
             20                  25                  30

Ile Lys Asn Ile Asp Lys Thr Pro Arg Ile Glu Thr Ile Glu Ser Thr
         35                  40                  45

Ser Thr Val His Lys Val Ser Thr Met Lys Arg Gln Pro Cys Gln Lys
     50                  55                  60

Tyr Gln Asn
 65

<210> SEQ ID NO 14
<211> LENGTH: 555
<212> TYPE: DNA
<213> ORGANISM: Unknown Organism
<220> FEATURE:
<223> OTHER INFORMATION: Monkey IPM 150 cDNA (partial)
<220> FEATURE:
<223> OTHER INFORMATION: Description of Unknown Organism: Monkey species
<400> SEQUENCE: 14
attttctttc cgaacggggt taaagtctgt ccacaggaat ccatgaaaca gattttagcc     60
agtcttcaag cttattatag attgagagtg tgtcaggaag cagtatggga agcatatcgg    120
atctttctgg atcgcatccc tgacacaggg gaatatcagg actgggtcag cttctgccag    180
caggagacct tctgcctctt tgacatcgga caaaacttca gcaattccca ggagcacctg    240
gatcttctcc agcagagaat aaaacagaga agtttccctg agagaaaaga tgaagtatct    300
```

```
acagagaaga cattgggaga gcctagtgaa accattgtgg tttcaacaga tgttgccagc    360
gtctcacttg ggccttttcc tgtcactcct gatgacaccc tcctcaatga aattctcgat    420
aatgcactca acgacaccaa gatgcctaca acagaaagag aaacagaact cgctgtgtct    480
gaggagcaga gggtggagct cagcatctct ctgataaacc agaggttcaa ggcagagctc    540
gctgactctc agtca                                                     555
```

```
<210> SEQ ID NO 15
<211> LENGTH: 185
<212> TYPE: PRT
<213> ORGANISM: Unknown Organism
<220> FEATURE:
<223> OTHER INFORMATION: Description of Unknown Organism: Monkey species
<220> FEATURE:
<223> OTHER INFORMATION: Monkey IPM 150 amino acid sequence (partial).

<400> SEQUENCE: 15

Ile Phe Phe Pro Asn Gly Val Lys Val Cys Pro Gln Glu Ser Met Lys
 1               5                  10                  15

Gln Ile Leu Ala Ser Leu Gln Ala Tyr Tyr Arg Leu Arg Val Cys Gln
             20                  25                  30

Glu Ala Val Trp Glu Ala Tyr Arg Ile Phe Leu Asp Arg Ile Pro Asp
         35                  40                  45

Thr Gly Glu Tyr Gln Asp Trp Val Ser Phe Cys Gln Gln Glu Thr Phe
     50                  55                  60

Cys Leu Phe Asp Ile Gly Gln Asn Phe Ser Asn Ser Gln Glu His Leu
 65                  70                  75                  80

Asp Leu Leu Gln Gln Arg Ile Lys Gln Arg Ser Phe Pro Glu Arg Lys
                 85                  90                  95

Asp Glu Val Ser Thr Glu Lys Thr Leu Gly Glu Pro Ser Glu Thr Ile
            100                 105                 110

Val Val Ser Thr Asp Val Ala Ser Val Ser Leu Gly Pro Phe Pro Val
        115                 120                 125

Thr Pro Asp Asp Thr Leu Leu Asn Glu Ile Leu Asp Asn Ala Leu Asn
    130                 135                 140

Asp Thr Lys Met Pro Thr Thr Glu Arg Glu Thr Glu Leu Ala Val Ser
145                 150                 155                 160

Glu Glu Gln Arg Val Glu Leu Ser Ile Ser Leu Ile Asn Gln Arg Phe
                165                 170                 175

Lys Ala Glu Leu Ala Asp Ser Gln Ser
            180                 185
```

```
<210> SEQ ID NO 16
<211> LENGTH: 4166
<212> TYPE: DNA
<213> ORGANISM: Homo sapiens
<220> FEATURE:
<223> OTHER INFORMATION: Human IPM 200 (isoform A) cDNA

<400> SEQUENCE: 16
cgggctactt tgaaaggaca accattttc tttccgctaa tttataatgg ttttgaagtg     60
gttgttcatt ctcaaacata gacttttaaa tgttaggtct ttcctataac tctttgttat    120
tggaagtttc aaggatttgg acactcaatt aaggattctg tcctctcctc attcctttgg    180
ttttggccca atgattatg tttcctcttt tgggaagat ttctctgggt attttgatat      240
ttgtcctgat agaaggagac tttccatcat taacagcaca aacctactta tctatagagg    300
```

-continued

```
agatccaaga acccaagagt gcagtttctt ttctcctgcc tgaagaatca acagacccttt    360 ctctagctac caaaaagaaa cagcctctgg accgcagaga aactgaaaga cagtggttaa    420
tcagaaggcg gagatctatt ctgtttccta atggagtgaa atctgccca gatgaaagtg     480 ttgcagaggc tgtggcaaat catgtgaagt attttaaagt ccgagtgtgt caggaagctg    540
tctgggaagc cttcaggact ttttgggatc gacttcctgg gcgtgaggaa tatcattact    600
ggatgaattt gtgtgaggat ggagtcacaa gtatatttga atgggcaca aattttagtg     660 aatctgtgga acatagaagc ttaatcatga agaaactgac ttatgcaaag gaaactgtaa    720
gcagctctga actgtcttct ccagttcctg ttggtgatac ttcaacattg ggagacacta    780
ctctcagtgt tccacatcca gaggtggacg cctatgaagg tgcctcagag agcagcttgg    840
aaaggccaga ggagagtatt agcaatgaaa ttgagaatgt gatagaagaa gccacaaaac    900
cagcaggtga acagattgca gaattcagta tccacctttt ggggaagcag tacagggaag    960
aactacagga ttcctccagc tttcaccacc agcaccttga agaagaattt atttcagagg    1020
ttgaaaatgc atttactggg ttaccaggct acaaggaaat tcgtgtactt gaatttaggt    1080
cccccaagga aaatgacagt ggcgtagatg tttactatgc agttaccttc aatggtgagg    1140
ccatcagcaa taccacctgg gacctcatta gccttcactc caacaaggtg gaaaaccatg    1200
gccttgtgga actggatgat aaacccactg ttgtttatac aatcagtaac ttcagagatt    1260
atattgctga gacattgcag cagaattttt tgctggggaa ctcttccttg aatccagatc    1320
ctgattccct gcagcttatc aatgtgagag gagttttgcg tcaccaaact gaagatctag    1380
tttggaacac ccaaagttca agtcttcagg caacgccgtc atctattctg gataatacct    1440
ttcaagctgc atggccctca gcagatgaat ccatcaccag cagtattcca ccacttgatt    1500
tcagctctgg tcctccctca gccactggca gggaactctg gtcagaaagt cctttgggtg    1560
atttagtgtc tacacacaaa ttagccttc cctcgaagat gggcctcagc tcttccccag     1620
aggttttaga ggttagcagc ttgactcttc attctgtcac cccggcagtg cttcagactg    1680
gcttgcctgt ggcttctgag gaaaggactt ctggatctca cttggtagaa gatggattag    1740
ccaatgttga agagtcagaa gattttcttt ctattgattc attgccttca agttcattca    1800
ctcaacctgt gccaaaagaa acaataccat ccatggaaga ctctgatgtg tccttaacat    1860
cttcaccata tctgacctct tctataacct ttggcttgga ctccttgacc tccaaagtca    1920
aagaccaatt aaaagtgagc ccttttcctgc cagatgcatc catggaaaaa gagttaatat    1980
ttgacggtgg tttaggttca gggtctgggc aaaaggtaga tctgattact tggccatgga    2040
gtgagacttc atcagagaag agcgccgaac cactgtccaa gccgtggctt gaagatgatg    2100
attcactttt gccagctgag attgaagaca agaaactagt tttagttgac aaaatggatt    2160
ccacagacca aattagtaag cactcaaaat atgaacatga tgacagatcc acacactttc    2220
cagaggaaga gcctcttagt gggcctgctg tgcccatctt cgcagatact gcagctgaat    2280
ctgcgtctct aaccctcccc aagcacatat cagaagtacc tggtgttgat gattgctcag    2340
ttaccaaagc acctcttata ctgacatctg tagcaatctc tgcctctact gataaatcag    2400
atcaggcaga tgccatccta agggaggata tggaacaaat tactgagtca tccaactatg    2460
aatggtttga cagtgagggtt tcaatggtaa agccagatat gcaaactttg tggactatat    2520
tgccagaatc agagagagtt tggacaagaa cttcttccct agagaaattg tccagagaca    2580
tattggcaag tacaccacag agtgctgaca ggctctggtt atctgtgaca cagtctacca    2640
aattgcctcc aaccacaatc tccaccctgc tagaggatga agtaattatg ggtgtacagg    2700
```

```
atatttcgtt agaactggac cggataggca cagattacta tcagcctgag caagtccaag   2760
agcaaaatgg caaggttggt agttatgtgg aaatgtcaac aagtgttcac tccacagaga   2820
tggttagtgt ggcttggccc acagaaggag agatgactt gagttatacc cagacttcag    2880
gagctttggt ggttttcttc agcctccgag tgactaacat gatgttttca gaagatctgt   2940
ttaataaaaa ctccttggag tataaagccc tggagcaaag attcttagaa ttgctggttc   3000
cctatctcca gtcaaatctc acggggttcc agaacttaga aatcctcaac ttcagaaatg   3060
gcagcattgt ggtgaacagt cgaatgaagt ttgccaattc tgtccctcct aacgtcaaca   3120
atgcggtgta catgattctg gaagactttt gtaccactgc ctacaatacc atgaacttgg   3180
ctattgataa atactctctt gatgtggaat caggtgatga agccaaccct tgcaagtttc   3240
aggcctgtaa tgaattttca gagtgtctgg tcaacccctg gagtggagaa gcaaagtgca   3300
gatgcttccc tggatacctg agtgtggaag aacggccctg tcagagtctc tgtgacctac   3360
agcctgactt ctgcttgaat gatggaaagt gtgacattat gcctgggcac ggggccattt   3420
gtaggtgccg ggtgggtgag aactggtggt accgaggcaa gcactgtgag gaatttgtgt   3480
ctgagcccgt gatcataggc atcactattg cctccgtggt tggacttctt gtcatctttt   3540
ctgctatcat ctacttcttc atcaggactc ttcaagcaca ccatgacagg agtgaaagag   3600
agagtccctt cagtggctcc agcaggcagc ctgacagcct ctcatctatt gagaatgctg   3660
tgaagtacaa ccccgtgtat gaaagtcaca gggctggatg tgagaagtat gagggaccct   3720
atcctcagca tcccttctac agctctgcta gcggagacgt gattggtggg ctgagcagag   3780
aagaaatcag acagatgtat gagagcagtg agctttccag agaggaaatt caagagagaa   3840
tgagagtttt ggaactgtat gccaatgatc ctgagtttgc agcttttgtg agagagcaac   3900
aagtggaaga ggtttaacca aaactcctgt tctgaaactg attagaagcc tggagaagat   3960
ggagattact tgttacttat gtcatataat taacctggat tttaaacact gttggaagaa   4020
gagtttctta tgaaaaaatt aaatataggg cacactgttt ttttttcagc ttaagttttc   4080
agaatgtagt aagagatgtt accatttta tttctataaa gactgaatgc tgtgtttaaa    4140
taaattgaaa actacgtaaa aaaaaa                                         4166
```

<210> SEQ ID NO 17
<211> LENGTH: 1241
<212> TYPE: PRT
<213> ORGANISM: Homo sapiens
<220> FEATURE:
<223> OTHER INFORMATION: Human IPM 200 amino acid sequence, isoform A

<400> SEQUENCE: 17

```
Met Ile Met Phe Pro Leu Phe Gly Lys Ile Ser Leu Gly Ile Leu Ile
1               5                   10                  15

Phe Val Leu Ile Glu Gly Asp Phe Pro Ser Leu Thr Ala Gln Thr Tyr
            20                  25                  30

Leu Ser Ile Glu Glu Ile Gln Glu Pro Lys Ser Ala Val Ser Phe Leu
        35                  40                  45

Leu Pro Glu Glu Ser Thr Asp Leu Ser Leu Ala Thr Lys Lys Lys Gln
    50                  55                  60

Pro Leu Asp Arg Arg Glu Thr Glu Arg Gln Trp Leu Ile Arg Arg Arg
65                  70                  75                  80

Arg Ser Ile Leu Phe Pro Asn Gly Val Lys Ile Cys Pro Asp Glu Ser
                85                  90                  95
```

-continued

```
Val Ala Glu Ala Val Ala Asn His Val Lys Tyr Phe Lys Val Arg Val
            100                 105                 110

Cys Gln Glu Ala Val Trp Glu Ala Phe Arg Thr Phe Trp Asp Arg Leu
            115                 120                 125

Pro Gly Arg Glu Glu Tyr His Tyr Trp Met Asn Leu Cys Glu Asp Gly
            130                 135                 140

Val Thr Ser Ile Phe Glu Met Gly Thr Asn Phe Ser Glu Ser Val Glu
145                 150                 155                 160

His Arg Ser Leu Ile Met Lys Lys Leu Thr Tyr Ala Lys Glu Thr Val
                165                 170                 175

Ser Ser Ser Glu Leu Ser Ser Pro Val Pro Val Gly Asp Thr Ser Thr
            180                 185                 190

Leu Gly Asp Thr Thr Leu Ser Val Pro His Pro Glu Val Asp Ala Tyr
            195                 200                 205

Glu Gly Ala Ser Glu Ser Ser Leu Glu Arg Pro Glu Glu Ser Ile Ser
            210                 215                 220

Asn Glu Ile Glu Asn Val Ile Glu Glu Ala Thr Lys Pro Ala Gly Glu
225                 230                 235                 240

Gln Ile Ala Glu Phe Ser Ile His Leu Leu Gly Lys Gln Tyr Arg Glu
            245                 250                 255

Glu Leu Gln Asp Ser Ser Ser Phe His His Gln His Leu Glu Glu Glu
            260                 265                 270

Phe Ile Ser Glu Val Glu Asn Ala Phe Thr Gly Leu Pro Gly Tyr Lys
            275                 280                 285

Glu Ile Arg Val Leu Glu Phe Arg Ser Pro Lys Glu Asn Asp Ser Gly
            290                 295                 300

Val Asp Val Tyr Ala Val Thr Phe Asn Gly Glu Ala Ile Ser Asn
305                 310                 315                 320

Thr Thr Trp Asp Leu Ile Ser Leu His Ser Asn Lys Val Glu Asn His
                325                 330                 335

Gly Leu Val Glu Leu Asp Asp Lys Pro Thr Val Val Tyr Thr Ile Ser
            340                 345                 350

Asn Phe Arg Asp Tyr Ile Ala Glu Thr Leu Gln Gln Asn Phe Leu Leu
            355                 360                 365

Gly Asn Ser Ser Leu Asn Pro Asp Pro Asp Ser Leu Gln Leu Ile Asn
            370                 375                 380

Val Arg Gly Val Leu Arg His Gln Thr Glu Asp Leu Val Trp Asn Thr
385                 390                 395                 400

Gln Ser Ser Ser Leu Gln Ala Thr Pro Ser Ser Ile Leu Asp Asn Thr
                405                 410                 415

Phe Gln Ala Ala Trp Pro Ser Ala Asp Glu Ser Ile Thr Ser Ser Ile
            420                 425                 430

Pro Pro Leu Asp Phe Ser Ser Gly Pro Pro Ser Ala Thr Gly Arg Glu
            435                 440                 445

Leu Trp Ser Glu Ser Pro Leu Gly Asp Leu Val Ser Thr His Lys Leu
            450                 455                 460

Ala Phe Pro Ser Lys Met Gly Leu Ser Ser Pro Glu Val Leu Glu
465                 470                 475                 480

Val Ser Ser Leu Thr Leu His Ser Val Thr Pro Ala Val Leu Gln Thr
                485                 490                 495

Gly Leu Pro Val Ala Ser Glu Glu Arg Thr Ser Gly Ser His Leu Val
            500                 505                 510

Glu Asp Gly Leu Ala Asn Val Glu Glu Ser Glu Asp Phe Leu Ser Ile
```

-continued

```
             515                 520                 525
Asp Ser Leu Pro Ser Ser Phe Thr Gln Pro Val Pro Lys Glu Thr
         530                 535                 540
Ile Pro Ser Met Glu Asp Ser Asp Val Ser Leu Thr Ser Ser Pro Tyr
545                 550                 555                 560
Leu Thr Ser Ser Ile Pro Phe Gly Leu Asp Ser Leu Thr Ser Lys Val
                 565                 570                 575
Lys Asp Gln Leu Lys Val Ser Pro Phe Leu Pro Asp Ala Ser Met Glu
             580                 585                 590
Lys Glu Leu Ile Phe Asp Gly Gly Leu Gly Ser Gly Ser Gly Gln Lys
         595                 600                 605
Val Asp Leu Ile Thr Trp Pro Trp Ser Glu Thr Ser Ser Glu Lys Ser
610                 615                 620
Ala Glu Pro Leu Ser Lys Pro Trp Leu Glu Asp Asp Ser Leu Leu
625                 630                 635                 640
Pro Ala Glu Ile Glu Asp Lys Lys Leu Val Leu Val Asp Lys Met Asp
                 645                 650                 655
Ser Thr Asp Gln Ile Ser Lys His Ser Lys Tyr Glu His Asp Asp Arg
             660                 665                 670
Ser Thr His Phe Pro Glu Glu Pro Leu Ser Gly Pro Ala Val Pro
         675                 680                 685
Ile Phe Ala Asp Thr Ala Ala Glu Ser Ala Ser Leu Thr Leu Pro Lys
     690                 695                 700
His Ile Ser Glu Val Pro Gly Val Asp Asp Cys Ser Val Thr Lys Ala
705                 710                 715                 720
Pro Leu Ile Leu Thr Ser Val Ala Ile Ser Ala Ser Thr Asp Lys Ser
                 725                 730                 735
Asp Gln Ala Asp Ala Ile Leu Arg Glu Asp Met Glu Gln Ile Thr Glu
             740                 745                 750
Ser Ser Asn Tyr Glu Trp Phe Asp Ser Glu Val Ser Met Val Lys Pro
         755                 760                 765
Asp Met Gln Thr Leu Trp Thr Ile Leu Pro Glu Ser Glu Arg Val Trp
     770                 775                 780
Thr Arg Thr Ser Ser Leu Glu Lys Leu Ser Arg Asp Ile Leu Ala Ser
785                 790                 795                 800
Thr Pro Gln Ser Ala Asp Arg Leu Trp Leu Ser Val Thr Gln Ser Thr
                 805                 810                 815
Lys Leu Pro Pro Thr Thr Ile Ser Thr Leu Leu Glu Asp Glu Val Ile
             820                 825                 830
Met Gly Val Gln Asp Ile Ser Leu Glu Leu Asp Arg Ile Gly Thr Asp
         835                 840                 845
Tyr Tyr Gln Pro Glu Gln Val Gln Glu Gln Asn Gly Lys Val Gly Ser
     850                 855                 860
Tyr Val Glu Met Ser Thr Ser Val His Ser Thr Glu Met Val Ser Val
865                 870                 875                 880
Ala Trp Pro Thr Glu Gly Gly Asp Asp Leu Ser Tyr Thr Gln Thr Ser
                 885                 890                 895
Gly Ala Leu Val Val Phe Phe Ser Leu Arg Val Thr Asn Met Met Phe
             900                 905                 910
Ser Glu Asp Leu Phe Asn Lys Asn Ser Leu Glu Tyr Lys Ala Leu Glu
         915                 920                 925
Gln Arg Phe Leu Glu Leu Leu Val Pro Tyr Leu Gln Ser Asn Leu Thr
     930                 935                 940
```

Gly Phe Gln Asn Leu Glu Ile Leu Asn Phe Arg Asn Gly Ser Ile Val
945                 950                 955                 960

Val Asn Ser Arg Met Lys Phe Ala Asn Ser Val Pro Pro Asn Val Asn
            965                 970                 975

Asn Ala Val Tyr Met Ile Leu Glu Asp Phe Cys Thr Thr Ala Tyr Asn
        980                 985                 990

Thr Met Asn Leu Ala Ile Asp Lys Tyr Ser Leu Asp Val Glu Ser Gly
    995                 1000                1005

Asp Glu Ala Asn Pro Cys Lys Phe Gln Ala Cys Asn Glu Phe Ser Glu
1010                1015                1020

Cys Leu Val Asn Pro Trp Ser Gly Glu Ala Lys Cys Arg Cys Phe Pro
1025                1030                1035                1040

Gly Tyr Leu Ser Val Glu Glu Arg Pro Cys Gln Ser Leu Cys Asp Leu
            1045                1050                1055

Gln Pro Asp Phe Cys Leu Asn Asp Gly Lys Cys Asp Ile Met Pro Gly
            1060                1065                1070

His Gly Ala Ile Cys Arg Cys Arg Val Gly Glu Asn Trp Trp Tyr Arg
    1075                1080                1085

Gly Lys His Cys Glu Glu Phe Val Ser Glu Pro Val Ile Gly Ile
1090                1095                1100

Thr Ile Ala Ser Val Val Gly Leu Leu Val Ile Phe Ser Ala Ile Ile
1105                1110                1115                1120

Tyr Phe Phe Ile Arg Thr Leu Gln Ala His His Asp Arg Ser Glu Arg
            1125                1130                1135

Glu Ser Pro Phe Ser Gly Ser Ser Arg Gln Pro Asp Ser Leu Ser Ser
            1140                1145                1150

Ile Glu Asn Ala Val Lys Tyr Asn Pro Val Tyr Glu Ser His Arg Ala
    1155                1160                1165

Gly Cys Glu Lys Tyr Glu Gly Pro Tyr Pro Gln His Pro Phe Tyr Ser
    1170                1175                1180

Ser Ala Ser Gly Asp Val Ile Gly Gly Leu Ser Arg Glu Glu Ile Arg
1185                1190                1195                1200

Gln Met Tyr Glu Ser Ser Glu Leu Ser Arg Glu Glu Ile Gln Glu Arg
            1205                1210                1215

Met Arg Val Leu Glu Leu Tyr Ala Asn Asp Pro Glu Phe Ala Ala Phe
            1220                1225                1230

Val Arg Glu Gln Gln Val Glu Glu Val
            1235                1240

<210> SEQ ID NO 18
<211> LENGTH: 2964
<212> TYPE: DNA
<213> ORGANISM: Homo sapiens
<220> FEATURE:
<223> OTHER INFORMATION: Human IPM 200 cDNA sequence, isoform C

<400> SEQUENCE: 18
aaacttaagc ttggagtttg gaagtttcaa ggatttggac actcaattaa ggattctgtc    60
ctctcctcat tcctttggtt ttggcccaaa tgattatgtt tcctcttttt gggaagattt   120
ctctgggtat tttgatattt gtcctgatag aaggagactt ccatcatta acagcacaaa    180 cctacttatc tatagaggag atccaagaac ccaagagtgc agtttctttt ctcctgcctg    240
aagaatcaac agacctttct ctagctacca aaaagaaaca gcctctggac cgcagagaaa    300
ctgaaagaca gtggttaatc agaaggcgga gatctattct gtttcctaat ggagtgaaaa    360

-continued

```
tctgcccaga tgaaagtgtt gcagaggctg tggcaaatca tgtgaagtat tttaaagtcc    420
gagtgtgtca ggaagctgtc tgggaagcct tcaggacttt ttgggatcsa cttcctgggc    480
gtgaggaata tcattactgg atgaatttgt gtgaggatgg agtcacaagt atatttgaaa    540
tgggcacaaa ttttagtgaa tctgtggaac atagaagctt aatcatgaag aaactgactt    600
atgcaaagga aactgtaagc agctctgaac tgtcttctcc agttcctgtt ggtgatactt    660
caacatthgg agacactact ctcagtgttc cacatccaga ggtggacgcc tatgaaggtg    720
cctcagagag cagcttggaa aggccagagg agagtattag caatgaaatt gagaatgtga    780
tagaagaagc cacaaaacca gcaggtgaac agattgcaga attcagtatc cacctttttgg   840 ggaagcagta cagggaagaa ctacaggatt cctccagctt tcaccaccag cacctttgaag    900 aagaatttat ttcagaggtt gaaaatgcat ttactgggtt accaggctac aaggaaattc    960
gtgtacttga atttaggtcc cccaaggaaa atgacagtgg cgtagatgtt tactatgcag   1020
ttaccttcaa tggtgaggcc atcagcaata ccacctggga cctcattagc cttcactcca   1080
acaaggtgga aaaccatggc cttgtggaac tggatgataa acccactgtt gtttatacaa   1140
tcagtaactt cagagattat attgctgaga cattgcagca gaattttttg ctggggaact   1200
cttccttgaa tccagatcct gattccctgc agcttatcaa tgtgagagga gttttgcgtc   1260
accaaactga agatctagtt tggaacaccc aaagttcaag tcttcaggca acgccgtcat   1320
ctattctgtg cttcaractg gcttgcctgt ggcttctgag gaaaggactt ctggatctca   1380
cttggtagaa gatggattag ccaatgttga agagtcagaa gattttcttt ctattgattc   1440
attgccttca agttcattca ctcaacctgt gccaaaagaa acaataccat ccatggaaga   1500
ctctgatgtg tccttaacat cttcaccata tctgacctct tctatacctt ttggcttgga   1560
ctccttgacc tccaaagtca agaccaatt aaaagtgagc cctttcctgc cagatgcatc   1620
catgaaaaaa gagttaatat ttgacggtgg tttaggttca gggtctgggc aaaaggtaga   1680
tctgattact tggccatgga gtgagacttc atcagagaag agcgctgaac cactgtccaa   1740
gccgtggctt gaagatgatg attcacttttt gccagctgag attgaagaca gaaaactagt   1800
tttagttgac aaaatggatt ccacagacca aattagtaag cactcaaaat atgaacatga   1860
tgacagatcc atacactttc agaggaagaa gcctcttagt gggcctgctg tgcccatctt   1920
cgcagatact gcagctgaat ctgcgtctct aaccctcccc aagcacatat cagaagtacc   1980
tggtgttgat gattactcag ttaccaaagc acctcttata ctgacatctg tagcaatctc   2040
tgcctctact gataaatcag atcaggcaga tgccatccta agggaggata tggaacaaat   2100
tactgagtca tccaactatg aatggtttga cagtgaggtt tcaatggtaa agccagatat   2160
gcaaactttg tggactatat tgccagaatc agagagagtt tggacaagaa cttcttccct   2220
agagaaattg tccagagaca tattggcaag tacaccacag agtgctgaca ggctctggtt   2280
atctgtgaca cagtctacca aattgcctcc aaccacaatc tccaccctgc tagaggatga   2340
agtaattatg ggtgtacagg atatttcgtt agaactggac cggataggca cagattacta   2400
tcagcctgag caagtccaag agcaaaatgg caaggttggt agtatgtgg aaatgtcaac   2460 aagtgttcac tccacagaga tggttagtgt ggcttggccc acagaaggag agatgactt   2520 gagttatacc cagacttcag gagctttggt ggttttcttc agcctccgag tgactaacat   2580
gatgttttca gaagatctgt ttaataaaaa ctccttggag tataaagccc tggagcaaag   2640
attcttagaa ttgctggttc cctatctcca gtcaaatctc acggggttcc agaacttaga   2700
```

-continued

```
aatcctcaac ttcagaaatg gcagcattgt ggtgaacagt cgaatgaagt ttgccaattc    2760
tgtccctcct aacgtcaaca atgcggtgta catgattctg aagactttt gtaccactgc     2820 ctacaatacc atgaacttgg ctattgataa atactctctt gatgtggaat caggtgatga    2880
agccaaccct tgcaagtttc aggcctgtaa tgaattttca gaagtgtctg gtcaacccct    2940
ggagtggaga aacaaaagtg caga                                            2964
```

<210> SEQ ID NO 19
<211> LENGTH: 432
<212> TYPE: PRT
<213> ORGANISM: Homo sapiens
<220> FEATURE:
<223> OTHER INFORMATION: Human IPM 200 amino acid sequence, isoform C
<220> FEATURE:
<221> NAME/KEY: UNSURE
<222> LOCATION: (1)..(432)
<223> OTHER INFORMATION: Xaa is any amino acid.

<400> SEQUENCE: 19

```
Met Ile Met Phe Pro Leu Phe Gly Lys Ile Ser Leu Gly Ile Leu Ile
 1               5                  10                  15

Phe Val Leu Ile Glu Gly Asp Phe Pro Ser Leu Thr Ala Gln Thr Tyr
            20                  25                  30

Leu Ser Ile Glu Glu Ile Gln Glu Pro Lys Ser Ala Val Ser Phe Leu
        35                  40                  45

Leu Pro Glu Glu Ser Thr Asp Leu Ser Leu Ala Thr Lys Lys Lys Gln
    50                  55                  60

Pro Leu Asp Arg Arg Glu Thr Glu Arg Gln Trp Leu Ile Arg Arg Arg
65                  70                  75                  80

Arg Ser Ile Leu Phe Pro Asn Gly Val Lys Ile Cys Pro Asp Glu Ser
                85                  90                  95

Val Ala Glu Ala Val Ala Asn His Val Lys Tyr Phe Lys Val Arg Val
            100                 105                 110

Cys Gln Glu Ala Val Trp Glu Ala Phe Arg Thr Phe Trp Asp Xaa Leu
        115                 120                 125

Pro Gly Arg Glu Glu Tyr His Tyr Trp Met Asn Leu Cys Glu Asp Gly
    130                 135                 140

Val Thr Ser Ile Phe Glu Met Gly Thr Asn Phe Ser Glu Ser Val Glu
145                 150                 155                 160

His Arg Ser Leu Ile Met Lys Lys Leu Thr Tyr Ala Lys Glu Thr Val
                165                 170                 175

Ser Ser Ser Glu Leu Ser Ser Pro Val Pro Val Gly Asp Thr Ser Thr
            180                 185                 190

Leu Gly Asp Thr Thr Leu Ser Val Pro His Pro Glu Val Asp Ala Tyr
        195                 200                 205

Glu Gly Ala Ser Glu Ser Ser Leu Glu Arg Pro Glu Glu Ser Ile Ser
    210                 215                 220

Asn Glu Ile Glu Asn Val Ile Glu Glu Ala Thr Lys Pro Ala Gly Glu
225                 230                 235                 240

Gln Ile Ala Glu Phe Ser Ile His Leu Leu Gly Lys Gln Tyr Arg Glu
                245                 250                 255

Glu Leu Gln Asp Ser Ser Ser Phe His His Gln His Leu Glu Glu Glu
            260                 265                 270

Phe Ile Ser Glu Val Glu Asn Ala Phe Thr Gly Leu Pro Gly Tyr Lys
        275                 280                 285

Glu Ile Arg Val Leu Glu Phe Arg Ser Pro Lys Glu Asn Asp Ser Gly
```

```
              290                 295                 300
Val Asp Val Tyr Tyr Ala Val Thr Phe Asn Gly Glu Ala Ile Ser Asn
305                 310                 315                 320

Thr Thr Trp Asp Leu Ile Ser Leu His Ser Asn Lys Val Glu Asn His
                325                 330                 335

Gly Leu Val Glu Leu Asp Asp Lys Pro Thr Val Tyr Thr Ile Ser
            340                 345                 350

Asn Phe Arg Asp Tyr Ile Ala Glu Thr Leu Gln Gln Asn Phe Leu Leu
                355                 360                 365

Gly Asn Ser Ser Leu Asn Pro Asp Pro Asp Ser Leu Gln Leu Ile Asn
370                 375                 380

Val Arg Gly Val Leu Arg His Gln Thr Glu Asp Leu Val Trp Asn Thr
385                 390                 395                 400

Gln Ser Ser Ser Leu Gln Ala Thr Pro Ser Ser Ile Leu Cys Phe Xaa
                405                 410                 415

Leu Ala Cys Leu Trp Leu Leu Arg Lys Gly Leu Leu Asp Leu Thr Trp
                420                 425                 430

<210> SEQ ID NO 20
<211> LENGTH: 861
<212> TYPE: DNA
<213> ORGANISM: Homo sapiens
<220> FEATURE:
<223> OTHER INFORMATION: Human IPM 200 cDNA sequence, isoform F

<400> SEQUENCE: 20
tggaagtttc aaggatttgg acactcaatt aaggattctg tcctctcctc attcctttgg      60
ttttggccca atgattatg tttcctcttt tgggaagat ttctctgggt attttgatat       120
ttgtcctgat agaaggagac tttccatcat taacagcaca aacctactta tctatagagg     180
agatccaagc actgtgagga aatttgtgtct gagcccgtga tcataggcat cactattgcc    240
tccgtggttg gacttcttgt catctttct gctatcatct acttcttcat caggactctt     300
caagcacacc atgacaggag tgaaagagag agtcccttca gtggctccag caggcagcct    360
gacagcctct catctattga gaatgctgtg aagtacaacc ccgtgtatga aagtcacagg    420
gctggatgtg agaagtatga gggaccctat cctcagcatc ccttctacag ctctgctagc    480
ggagacgtga ttggtgggct gagcagagaa gaaatcagac agatgtatga gagcagtgag    540
ctttccagag aggaaattca agagagaatg agagttttgg aactgtatgc caatgatcct    600
gagtttgcag cttttgtgag agagcaacaa gtggaagagg tttaaccaaa actcctgttc    660
tgaaactgat tagaagcctg gagaagatgg agattacttg ttacttatgt catataatta    720
acctggattt taaacactgt tggaagaaga gttttctatg aaaaaattaa atataggcca    780
cactgttttt ttttcagctt aagttttcag aatgtagtaa gagatgttac cattttatt    840 tctataaaga ctgaatgctg t                                              861

<210> SEQ ID NO 21
<211> LENGTH: 41
<212> TYPE: PRT
<213> ORGANISM: Homo sapiens
<220> FEATURE:
<223> OTHER INFORMATION: Human IPM 200 amino acid sequence, isoform F

<400> SEQUENCE: 21

Met Ile Met Phe Pro Leu Phe Gly Lys Ile Ser Leu Gly Ile Leu Ile
1               5                   10                  15
```

Phe Val Leu Ile Glu Gly Asp Phe Pro Ser Leu Thr Ala Gln Thr Tyr
            20                  25                  30

Leu Ser Ile Glu Glu Ile Gln Ala Leu
        35                  40

<210> SEQ ID NO 22
<211> LENGTH: 3011
<212> TYPE: DNA
<213> ORGANISM: Homo sapiens
<220> FEATURE:
<223> OTHER INFORMATION: Human IPM 200, regulatory region
<220> FEATURE:
<221> NAME/KEY: misc_feature
<222> LOCATION: (1)..(3011)
<223> OTHER INFORMATION: n ia a, c, g, or t.

<400> SEQUENCE: 22

| | | | | | |
|---|---|---|---|---|---|
| gaacacttgt | aatacaaaac | aattcctatt | tacaaagttt | actggtaata | caaatacagt | 60 |
| agtttacaga | gaactttcat | gtctcttaat | tcttaacaac | gaccctgtga | tacaggtaga | 120 |
| gattatcaca | tgtaatttct | ttggtgagta | aaccggctca | aagagcttag | gttatttacc | 180 |
| aaaatcaaat | attaagtgat | aaaaccaaga | tttgagtcca | gggtttctca | atcttaaata | 240 |
| caggaatctt | tctagattac | tatgattctc | agaagttttt | tttagctttt | tggtcaaggc | 300 |
| tgtcaaaaag | aataattgcc | aacttaatat | ttgttaccta | agagttgtcc | cttgttctga | 360 |
| attgtcaata | tgaagctttt | cttaagatta | aactttgact | cagctaataa | aattttcggc | 420 |
| tttttttctcc | tactcataca | ataaatttgg | caagtaagtt | tcttataagc | ttaccagtat | 480 |
| tttgcaaata | caactatgca | aatatattta | atggtcattt | aggtttatta | gcttttataa | 540 |
| aggctgaaaa | tgtggtttat | ttgaggctgt | attgaaaaaa | tatacttgag | cttttcctaa | 600 |
| agcataaaat | aacattgagg | gtgatttagc | taacacaatt | agtcaaggat | tctcaagagg | 660 |
| aatgtggttt | agatctttac | aatacacttt | ttttcagaga | attttgccag | agataacatg | 720 |
| aaataaaata | taatttcatt | gctatttgat | agtaaatcca | agcttccaca | gggattctga | 780 |
| tgaattgctt | tctactaggt | ttacttgatt | taaaaaactg | ttctaatata | gagaatttca | 840 |
| tctgcaggga | aaatgttttc | ttggttaaga | gttcctcatg | tagataaaca | cactgggcct | 900 |
| cacatttaat | ggcaaattaa | gcaacaaagt | tatcgcacag | ctatcattta | tattaagtgc | 960 |
| ttaatatgtt | ccgggcacta | ctctaagcaa | agtgaagatt | gaattagtta | attagttaat | 1020 |
| ttaatcctca | cattagctct | accatgagtt | tactatttct | attccatttt | atacgtaagg | 1080 |
| aaggagacaa | agtaagtgat | ttttctatca | aggaaggaaa | tttgcaagag | aatagtttca | 1140 |
| ttacaaaaac | taaatttgta | cgtagctctg | tattattgaa | ataggtagat | atagtcagtc | 1200 |
| tggacttttt | atgcttatac | atcttagtcc | ctaggaaaac | ccagaactaa | cagattcaga | 1260 |
| aaagttggaa | aaatcagtga | attatatgtg | aaacacatta | ttcttagtgg | actgcttgtt | 1320 |
| aaaggcaagg | agagtgttag | taaagagctt | aggtagatta | gaataaagaa | attgtctctc | 1380 |
| tccatctgct | ctaattagct | tatctcacca | gcttttatag | catgctggtt | atttcagaaa | 1440 |
| agaagtgaga | gctactttga | aaggacaacc | attttcttt | ccgctaattt | ataatggttt | 1500 |
| tgaagtggtt | gttcattctc | aaacatagac | ttttaaatgt | taggtctttc | ctataactct | 1560 |
| ttgttattgg | aagtttcaag | gatttggaca | ctcaattaag | gattctgtcc | tctcctcatt | 1620 |
| cctttggttt | tggcccaaat | gattatgttt | cctcttttg | ggaagatttc | tctgggtatt | 1680 |
| ttgatatttg | tcctgataga | aggagacttt | ccatcattaa | caggtattta | aaaatctaca | 1740 |
| tttgtttgta | tcttttccata | tctgtagtat | atgttcttca | aaaataggat | tatttgatgt | 1800 |

-continued

```
gattgctgta agaaatggaa tcaaatactt tattaatctt tgatatggct tcatttaaac    1860
cgttttaaaa tatctcccaa taattttggt tttccctcat tagtaatttc tggtttaaac    1920
cttactttta tttattttgt tgaaattgga tgtgtattta cttgattttg ataacaatct    1980
tgaatgaaag gagtgggagt taaatggaaa aagatggact gcctcactcc tcttttcctt    2040
agatatgcat gcctgcctat gatttgggca ctggcttctc tatcttaatg tagcccaagt    2100
gtcagttttt ctttagttgt tacctttgt actgtatctt cattatcgaa gacttgacta    2160
tactttcact ctgtagcaca aacctactta tctatagagg agatccaaga acccaagagt    2220
gcagtttctt ttctcctgcc tgaagaatca acagaccttt ctctagctac caaaaagaaa    2280
cagcctctgg accgcagaga aactgaaaga cagtggttaa tcagaaggcg agatctatt    2340 ctgtttccta atggagtgaa atctgccca gatgaaagtg ttgcagaggc tgtggcaaat    2400
catgtgaagt attttaaagt ccgaggtaag cgaacatcca aatccttcag ctccataatg    2460
aaattcaaac atagtttaat catttgttag gtaacattgt aaatcaaaat ttatgataat    2520
ttagacagga ctgagccaaa actacctttc tactgttaag aatatagtgt taatggtaac    2580
ttcagagaac agtttacatt aagagaggag gtttgttttt tttccagtgc cctccagtta    2640
aggcaataat atcatttaat aatgacatgc actttgaacc aaaggaagaa cgctttcatg    2700
atttgagttt gtagcttttg gtgcgttatg taagaaactt ttttcacatg agggcagtca    2760
caataagatg tctttcatta atttcaacaa catattcaga gaggaaatgt cttaaatctt    2820
tttaagcact tcaaaaatac cagtttatgt tttgggctac attaattta attttttactt    2880 cttcattaca gtaaatgcct aagtwtaccc acaaaatagc tttaccaaag ntatactcac    2940
ctgcttgcct atttaattaa tagttattat atatacaaat ataatgtttc tatatttat    3000 agtttagata t                                                         3011
```

<210> SEQ ID NO 23
<211> LENGTH: 4204
<212> TYPE: DNA
<213> ORGANISM: Mus sp.
<220> FEATURE:
<223> OTHER INFORMATION: Mouse IPM 200 cDNA sequence (partial)
<220> FEATURE:
<221> NAME/KEY: misc_feature
<222> LOCATION: (1)..(4204)
<223> OTHER INFORMATION: n is a, c, g, or t.

<400> SEQUENCE: 23

```
ccgtggcaaa ccatgtgaag tattttaaag cccgagtgtg ccaggaagcc atctgggaag     60
ccttcaggac gttttgggat cgacttcctg ggcgtgatga atatcgtcac tgatgaatt    120 tatgtgagga tggagtcaca agtgtatttg aaatgggcgc ccattttagt cagtctgtgg    180
aacatagaaa cctaatcatg aagaaactgg cttacacaag ggaagctgag agcagctcct    240
gcaaggatca gtcctgtggg cctgagttgt cctttccagt tcctattggt gagacctcaa    300
cactgacagg tgctgtctcc agtgcttcct atccagggtt ggcttcggag agcagcgcag    360
cgtcaccgca ggagagtatc agcaatgaaa ttgagaatgt gacagaggag cccacacaac    420
cagctgctga acagattgcg gaattcagca tccaacttct ggggaagcga tacagtgaag    480
aactgcggga tccctccagc gccctctacc ggctcctcgt ggaagagttt atttcagagg    540
ttgaaaaagc attcacaggg ttacctggct acaagggcat ccgtgttctg gaattcaggg    600 cccccggagga aaatgacagt gggatagatg ttcactatgc agttacccttc aatggcgaag    660
```

```
ccatcagcaa taccacctgg gacctcataa gccttcactc caacaaggta gaaaaccatg    720
gccttgtaga gatggatgat aaacccactg ctgtctatac aattagtaac ttcagagatt    780
atatcgctga gacgctgcac cagaacttttt tgatgggaaa ttcctctttg aatccagatc    840
ccaagcctct ccagctcatc aatgtgagag gagttttgct cccccaaaca gaagacatag    900
tttggaacac ccaaagttca agtcttcagg tgacaacatc ctctattttn gtgcttcagc    960
ctgacctgcc tgtggctcct gagggaagga cttctggatc gttcatatta gaagatgggt   1020
tagccagcac tgaagaatta gaagatactt ctattgatgg attgccttca agcccattaa   1080
ttcaacctgt gccaaaagaa acagtaccac ctatggaaga ctctgacacg ctctcttgt    1140 ccacaccaca tctgacctct tctgctatag aagaccttac taaagacata gggacacctt   1200
ctggcttgga gtccttggct tcaaacatct cagaccagtt ggaagtgatc ccatggtttc   1260
cagacacctc tgtggaaaaa gacttcattt ttgaaagtgg cttgggttct gggtctggga   1320
aagatgtaga tgtgattgat tggccatgga gtgagcttc attagagaag accactaaac   1380
cactgtcaaa gtcatggtct gaagaacagg atgcactatt accaactgag ggtagagaaa   1440
aattacatat agatggcaga gtagattcca cagaacaaat tattgaatca tcagaacata   1500
gatatggaga taggcccata cattttatag aggaagantc ccatgttaga tctactatac   1560
ccatctttgt agagtccgca actccaccta catctccaat cttttcaaaa cacacttcag   1620
atgtaccaga cattgattct tactcactta ccaaaccacc cttcttaccg gtaactatag   1680
caatccctgc ttccactaag aaaacagatg aggtactcaa ggaagatatg gtacatacag   1740
aatcatccag tcacaaagaa cttgacagtg aggttccagt gtcaaggcca gatatgcagc   1800
ctgtgtggac catgttgcca gaatcagata cagtttggac aagaacttct tccttaggga   1860
aattgtccag agacacattg gcaagtacac cagagagcac tgacagactc tggttgaaag   1920
cttccatgac acagtccact gaattgcctt caaccaccca ctccacccag ctagaggagg   1980
aagtaataat ggcggtccag gatatttcat tagaactaga tcaggtaggc acagattatt   2040
atcagtccga gctaactgaa gaacaacatg gcaaggctga cagctatgtg gaaatgtcta   2100
ccagtgttca ctacacagag atgcctattg tggctctgcc cacaaaagga ggtgttctga   2160
gtcacaccca gactgcagga gcattggtgg ttttcttcag cctccgcgtg acaaacatgt   2220 tgtttttcaga agacttgttt aacaaaaact ctttggaata taaagccctg gaacaaagat   2280
tcttagaact gctggctccc tatctccagt caaatctgtc agggttccag aacctagaaa   2340
tcctgagttt cagaaacggc agcattgtgg tgaacagccg agtgaggttc gccgagtctg   2400
cccctcctaa tgtcaacaag gccatgtata ggattctgga agacttttgt accactgcct   2460
accaaaccat gaacttggat atcgataagt actccctgga cgtggaatca ggtgatgagg   2520
ccaacccttg caagtttcag gcctgtaatg aattttctga gtgtttggta aatccatgga   2580
gtggagaagc aaagtgcaaa tgctaccctg ggtacctgag tgtggatgaa ctgccttgtc   2640
aaagtctctg tgatctacag cctgacttct gcttgaacga tggaaagtgt gacattatgc   2700
ctgggcatga agccatttgt agatgccggg ttggttcaaa ctggtggtat cgaggccaac   2760
actgtgagga gtttgtgtct gagcccttttg tcataggcat cactatagcc tctgtggtta   2820
gctttctcct tgttgcttct gctgtcgtct tcttccttgt gaagatgctt caagctcaga   2880
atgtcaggag agaaaggcag aggcccacca gctccagcag gcaccctgac agtctgtcat   2940
ctgttgagaa tgctatgaag tataaccctg catatgagag ccacttggct ggatgtgaac   3000
tgtatgagaa atcctatagc caacatccct tctatagctc tgctagtgaa gaggtgattg   3060
```

-continued

```
gtggtctgag cagagaagaa atcagacaga tgtatgaaag tagcgacctt tccaaagagg    3120
aaattcaaga gagaatgagg attttggaac tctatgctaa tgatcctgag tttgcagctt    3180
ttgtgagaga gcatcaaatg gaggagcttt aacttaaatg cctgattctt gacaccaatc    3240
agaagcttgg agaagatgga gaaggcttgt tctctctgct gtttaactaa tccagaagaa    3300
gagtttgtat tgaagaataa ataaggaaac atgggacgca cttctcattc aacactgca     3360 gcttaatttt ttggaatgga gcaaaaaaaa ataagtgat gtattttatt tcttacatta     3420
agagatgtgt caaagaaaaa ttaaagtggt gtgaactctg attttgtaac atattctaaa    3480
agcaaacaaa taaaacagaa ccaaaccaaa agcttaaagc cagaccttgg agttggggct    3540
gcagtgcctc tgactctgac tttttgagag catctctaag aactatggcc caggcttttct   3600 agtaagaaca taaagtgaga ctaatgagta agcttagaa tgcgactgtt ttgtgacata     3660
ctcgttaaag tcgaatgaga tagaggaagc tttgaagtaa ttttaatata gtttaaactc    3720
aaacactcat ctaaataaaa attaggcttt tggaacagat tgctgagtca ggcaatcttt    3780
aggtgcagta tatcttgttt atgtttgatg cttgcttcct atctgttctt gagcttcttg    3840
agcccataga tcaagactac aatgctctta aattagttat gtcaatattt gccacagttt    3900
ggtcctcaat taggcaccct taagaggaag caaattgagg aattncnntt catcagcttg    3960
gtttgtggac ataccagtgg gcctttttct tgattattaa ttgatgtaga aaggcccagc    4020
tcactatggg tggtactatc cttaggcagg ggtttgggga gttaagttgc aaaagaaagg    4080
taaagccagc tacaagaagc cagccaataa gcactttcct ttgtggtttc ttcttcaaac    4140
tcctgtcttg gcttctctct atggtagact ataacctata agccaaataa actctttctt    4200
ggaa                                                                4204
```

<210> SEQ ID NO 24
<211> LENGTH: 1069
<212> TYPE: PRT
<213> ORGANISM: Mus sp.
<220> FEATURE:
<223> OTHER INFORMATION: Mouse IPM 200 amino acid sequence (partial)
<220> FEATURE:
<221> NAME/KEY: UNSURE
<222> LOCATION: (1)..(1069)
<223> OTHER INFORMATION: Xaa is any amino acid.

<400> SEQUENCE: 24

```
Val Ala Asn His Val Lys Tyr Phe Lys Ala Arg Val Cys Gln Glu Ala
  1               5                  10                  15

Ile Trp Glu Ala Phe Arg Thr Phe Trp Asp Arg Leu Pro Gly Arg Asp
             20                  25                  30

Glu Tyr Arg His Trp Met Asn Leu Cys Glu Asp Gly Val Thr Ser Val
         35                  40                  45

Phe Glu Met Gly Ala His Phe Ser Gln Ser Val Glu His Arg Asn Leu
     50                  55                  60

Ile Met Lys Lys Leu Ala Tyr Thr Arg Glu Ala Glu Ser Ser Ser Cys
 65                  70                  75                  80

Lys Asp Gln Ser Cys Gly Pro Glu Leu Ser Phe Pro Val Pro Ile Gly
                 85                  90                  95

Glu Thr Ser Thr Leu Thr Gly Ala Val Ser Ser Ala Ser Tyr Pro Gly
            100                 105                 110

Leu Ala Ser Glu Ser Ser Ala Ala Ser Pro Gln Glu Ser Ile Ser Asn
        115                 120                 125
```

```
Glu Ile Glu Asn Val Thr Glu Pro Thr Gln Pro Ala Ala Glu Gln
    130                 135                 140

Ile Ala Glu Phe Ser Ile Gln Leu Leu Gly Lys Arg Tyr Ser Glu
145                 150                 155                 160

Leu Arg Asp Pro Ser Ser Ala Leu Tyr Arg Leu Leu Val Glu Glu Phe
                165                 170                 175

Ile Ser Glu Val Glu Lys Ala Phe Thr Gly Leu Pro Gly Tyr Lys Gly
            180                 185                 190

Ile Arg Val Leu Glu Phe Arg Ala Pro Glu Glu Asn Asp Ser Gly Ile
        195                 200                 205

Asp Val His Tyr Ala Val Thr Phe Asn Gly Glu Ala Ile Ser Asn Thr
    210                 215                 220

Thr Trp Asp Leu Ile Ser Leu His Ser Asn Lys Val Glu Asn His Gly
225                 230                 235                 240

Leu Val Glu Met Asp Asp Lys Pro Thr Ala Val Tyr Thr Ile Ser Asn
                245                 250                 255

Phe Arg Asp Tyr Ile Ala Glu Thr Leu His Gln Asn Phe Leu Met Gly
                260                 265                 270

Asn Ser Ser Leu Asn Pro Asp Pro Lys Pro Leu Gln Leu Ile Asn Val
            275                 280                 285

Arg Gly Val Leu Leu Pro Gln Thr Glu Asp Ile Val Trp Asn Thr Gln
    290                 295                 300

Ser Ser Ser Leu Gln Val Thr Thr Ser Ser Ile Xaa Val Leu Gln Pro
305                 310                 315                 320

Asp Leu Pro Val Ala Pro Glu Gly Arg Thr Ser Gly Ser Phe Ile Leu
                325                 330                 335

Glu Asp Gly Leu Ala Ser Thr Glu Glu Leu Glu Asp Thr Ser Ile Asp
            340                 345                 350

Gly Leu Pro Ser Ser Pro Leu Ile Gln Pro Val Pro Lys Glu Thr Val
        355                 360                 365

Pro Pro Met Glu Asp Ser Asp Thr Ala Leu Leu Ser Thr Pro His Leu
    370                 375                 380

Thr Ser Ser Ala Ile Glu Asp Leu Thr Lys Asp Ile Gly Thr Pro Ser
385                 390                 395                 400

Gly Leu Glu Ser Leu Ala Ser Asn Ile Ser Asp Gln Leu Glu Val Ile
                405                 410                 415

Pro Trp Phe Pro Asp Thr Ser Val Glu Lys Asp Phe Ile Phe Glu Ser
                420                 425                 430

Gly Leu Gly Ser Gly Ser Gly Lys Asp Val Asp Val Ile Asp Trp Pro
            435                 440                 445

Trp Ser Glu Thr Ser Leu Glu Lys Thr Thr Lys Pro Leu Ser Lys Ser
        450                 455                 460

Trp Ser Glu Glu Gln Asp Ala Leu Leu Pro Thr Glu Gly Arg Glu Lys
465                 470                 475                 480

Leu His Ile Asp Gly Arg Val Asp Ser Thr Glu Gln Ile Ile Glu Ser
                485                 490                 495

Ser Glu His Arg Tyr Gly Asp Arg Pro Ile His Phe Ile Glu Glu Xaa
            500                 505                 510

Ser His Val Arg Ser Thr Ile Pro Ile Phe Val Glu Ser Ala Thr Pro
        515                 520                 525

Pro Thr Ser Pro Ile Phe Ser Lys His Thr Ser Asp Val Pro Asp Ile
    530                 535                 540

Asp Ser Tyr Ser Leu Thr Lys Pro Pro Phe Leu Pro Val Thr Ile Ala
```

-continued

```
            545                 550                 555                 560
        Ile Pro Ala Ser Thr Lys Lys Thr Asp Glu Val Leu Lys Glu Asp Met
                        565                 570                 575

Val His Thr Glu Ser Ser Ser His Lys Glu Leu Asp Ser Glu Val Pro
                        580                 585                 590

Val Ser Arg Pro Asp Met Gln Pro Val Trp Thr Met Leu Pro Glu Ser
                        595                 600                 605

Asp Thr Val Trp Thr Arg Thr Ser Ser Leu Gly Lys Leu Ser Arg Asp
                        610                 615                 620

Thr Leu Ala Ser Thr Pro Glu Ser Thr Asp Arg Leu Trp Leu Lys Ala
        625                 630                 635                 640

Ser Met Thr Gln Ser Thr Glu Leu Pro Ser Thr Thr His Ser Thr Gln
                        645                 650                 655

Leu Glu Glu Glu Val Ile Met Ala Val Gln Asp Ile Ser Leu Glu Leu
                        660                 665                 670

Asp Gln Val Gly Thr Asp Tyr Tyr Gln Ser Glu Leu Thr Glu Glu Gln
                        675                 680                 685

His Gly Lys Ala Asp Ser Tyr Val Glu Met Ser Thr Ser Val His Tyr
                        690                 695                 700

Thr Glu Met Pro Ile Val Ala Leu Pro Thr Lys Gly Gly Val Leu Ser
        705                 710                 715                 720

His Thr Gln Thr Ala Gly Ala Leu Val Val Phe Phe Ser Leu Arg Val
                        725                 730                 735

Thr Asn Met Leu Phe Ser Glu Asp Leu Phe Asn Lys Asn Ser Leu Glu
                        740                 745                 750

Tyr Lys Ala Leu Glu Gln Arg Phe Leu Glu Leu Leu Ala Pro Tyr Leu
                        755                 760                 765

Gln Ser Asn Leu Ser Gly Phe Gln Asn Leu Glu Ile Leu Ser Phe Arg
                        770                 775                 780

Asn Gly Ser Ile Val Val Asn Ser Arg Val Arg Phe Ala Glu Ser Ala
        785                 790                 795                 800

Pro Pro Asn Val Asn Lys Ala Met Tyr Arg Ile Leu Glu Asp Phe Cys
                        805                 810                 815

Thr Thr Ala Tyr Gln Thr Met Asn Leu Asp Ile Asp Lys Tyr Ser Leu
                        820                 825                 830

Asp Val Glu Ser Gly Asp Glu Ala Asn Pro Cys Lys Phe Gln Ala Cys
                        835                 840                 845

Asn Glu Phe Ser Glu Cys Leu Val Asn Pro Trp Ser Gly Glu Ala Lys
                        850                 855                 860

Cys Lys Cys Tyr Pro Gly Tyr Leu Ser Val Asp Glu Leu Pro Cys Gln
        865                 870                 875                 880

Ser Leu Cys Asp Leu Gln Pro Asp Phe Cys Leu Asn Asp Gly Lys Cys
                        885                 890                 895

Asp Ile Met Pro Gly His Gly Ala Ile Cys Arg Cys Arg Val Gly Ser
                        900                 905                 910

Asn Trp Trp Tyr Arg Gly Gln His Cys Glu Glu Phe Val Ser Glu Pro
                        915                 920                 925

Phe Val Ile Gly Ile Thr Ile Ala Ser Val Val Ser Phe Leu Leu Val
                        930                 935                 940

Ala Ser Ala Val Val Phe Phe Leu Val Lys Met Leu Gln Ala Gln Asn
        945                 950                 955                 960

Val Arg Arg Glu Arg Gln Arg Pro Thr Ser Ser Arg His Pro Asp
                        965                 970                 975
```

Ser Leu Ser Ser Val Glu Asn Ala Met Lys Tyr Asn Pro Ala Tyr Glu
            980                 985                 990

Ser His Leu Ala Gly Cys Glu Leu Tyr Glu Lys Ser Tyr Ser Gln His
        995                 1000                1005

Pro Phe Tyr Ser Ser Ala Ser Glu Glu Val Ile Gly Gly Leu Ser Arg
    1010                1015                1020

Glu Glu Ile Arg Gln Met Tyr Glu Ser Ser Asp Leu Ser Lys Glu Glu
1025                1030                1035                1040

Ile Gln Glu Arg Met Arg Ile Leu Glu Leu Tyr Ala Asn Asp Pro Glu
            1045                1050                1055

Phe Ala Ala Phe Val Arg Glu His Gln Met Glu Glu Leu
            1060                1065

<210> SEQ ID NO 25
<211> LENGTH: 546
<212> TYPE: DNA
<213> ORGANISM: Macaca fascicularis
<220> FEATURE:
<223> OTHER INFORMATION: Monkey IPM 200 cDNA sequence (partial)

<400> SEQUENCE: 25
gaattcggct tggacaacca ttttctttc cgctaattta taatggtttt gaagtggttg      60
ttcattctca acatagact tttaaatgtt aggtctttcc tataacttgt tgttattgga     120
agtttcaagg atttggacgc tcagttaagg attttgtcct ctcctcattc ctttggtttt    180
ggcccaaatg attatgtttc ctcttttgg gaagatttct ctgggtattt tgatatttgt     240
cctgatagga gactttccat cgttaacagc acaaacctac ttatctttag aggagatcca    300
agaacccaag agtgcagttt cttttctcct gcctgaagaa tcaacagacc tttctctagc    360
taccaaaaag aaacagcctc tggacctcag agaaactgaa agacagtggt tactcagaag    420
gcggagatct attctgtttc ctaatggagt aaaaatctgc ccagatgaaa gtgttacaga    480
ggctgtggca atcatgtga agtattttaa agtccgagtg tgtcaggaag ctgtctggga    540
aaagcc                                                                 546

<210> SEQ ID NO 26
<211> LENGTH: 119
<212> TYPE: PRT
<213> ORGANISM: Macaca fascicularis
<220> FEATURE:
<223> OTHER INFORMATION: Monkey IPM 200 amino acid sequence (partial)

<400> SEQUENCE: 26

Met Ile Met Phe Pro Leu Phe Gly Lys Ile Ser Leu Gly Ile Leu Ile
  1               5                  10                  15

Phe Val Leu Ile Gly Asp Phe Pro Ser Leu Thr Ala Gln Thr Tyr Leu
            20                  25                  30

Ser Leu Glu Glu Ile Gln Pro Lys Ser Ala Val Ser Phe Leu Leu
        35                  40                  45

Pro Glu Glu Ser Thr Asp Leu Ser Leu Ala Thr Lys Lys Lys Gln Pro
    50                  55                  60

Leu Asp Leu Arg Glu Thr Glu Arg Gln Trp Leu Leu Arg Arg Arg Arg
 65                  70                  75                  80

Ser Ile Leu Phe Pro Asn Gly Val Lys Ile Cys Pro Asp Glu Ser Val
            85                  90                  95

Thr Glu Ala Val Ala Asn His Val Lys Tyr Phe Lys Val Arg Val Cys
            100                 105                 110

```
<210> SEQ ID NO 27
<211> LENGTH: 3261
<212> TYPE: DNA
<213> ORGANISM: Homo sapiens
<220> FEATURE:
<223> OTHER INFORMATION: Human IPM 150 isoform A variant cDNA sequence
<220> FEATURE:
<221> NAME/KEY: CDS
<222> LOCATION: (128)..(2440)

<400> SEQUENCE: 27
```

```
taaaccaaga aggttatcct caatcatctg gtatcaatat ataattattt ttcctttntg      60
ttacttttta atgagatttg aggttgttct gtgattgtta tcagaattac catgcacaaa     120 agccaga atg tat ttg gaa act aga aga gct att ttt gtt ttt tgg att      169
        Met Tyr Leu Glu Thr Arg Arg Ala Ile Phe Val Phe Trp Ile
          1               5                  10 ttt ctc caa gtt caa gga act aaa gat atc tcc att aac ata tac cat      217
Phe Leu Gln Val Gln Gly Thr Lys Asp Ile Ser Ile Asn Ile Tyr His
 15                  20                  25                  30 tct gaa act aaa gac ata gac aat ccc cca aga aat gaa aca act gaa      265
Ser Glu Thr Lys Asp Ile Asp Asn Pro Pro Arg Asn Glu Thr Thr Glu
                 35                  40                  45 agt act gaa aaa atg tac aaa atg tca act atg aga cga ata ttc gat      313
Ser Thr Glu Lys Met Tyr Lys Met Ser Thr Met Arg Arg Ile Phe Asp
             50                  55                  60 ttg gca aag cat cga aca aaa aga tcc gca ttt ttc cca acg ggg gtt      361
Leu Ala Lys His Arg Thr Lys Arg Ser Ala Phe Phe Pro Thr Gly Val
         65                  70                  75 aaa gtc tgt cca cag gaa tcc atg aaa cag att tta gac agt ctt caa      409
Lys Val Cys Pro Gln Glu Ser Met Lys Gln Ile Leu Asp Ser Leu Gln
     80                  85                  90 gct tat tat aga ttg aga gtg tgt cag gaa gca gta tgg gaa gca tat      457
Ala Tyr Tyr Arg Leu Arg Val Cys Gln Glu Ala Val Trp Glu Ala Tyr
 95                 100                 105                 110 cgg atc ttt ctg gat cgc atc cct gac aca ggg gaa tat cag gac tgg      505
Arg Ile Phe Leu Asp Arg Ile Pro Asp Thr Gly Glu Tyr Gln Asp Trp
                115                 120                 125 gtc agc atc tgc cag cag gag acc ttc tgc ctc ttt gac att gga aaa      553
Val Ser Ile Cys Gln Gln Glu Thr Phe Cys Leu Phe Asp Ile Gly Lys
            130                 135                 140 aac ttc agc aat tcc cag gag cac ctg gat ctt ctc cag cag aga ata      601
Asn Phe Ser Asn Ser Gln Glu His Leu Asp Leu Leu Gln Gln Arg Ile
        145                 150                 155 aaa cag aga agt ttc cct gac aga aaa gat gaa ata tct gca gag aag      649
Lys Gln Arg Ser Phe Pro Asp Arg Lys Asp Glu Ile Ser Ala Glu Lys
    160                 165                 170 aca ttg gga gag cct ggt gaa acc att gtc att tca aca gat gtt gcc      697
Thr Leu Gly Glu Pro Gly Glu Thr Ile Val Ile Ser Thr Asp Val Ala
175                 180                 185                 190 aac gtc tca ctt ggg cct ttc cct ctc act cct gat gac acc ctc ctc      745
Asn Val Ser Leu Gly Pro Phe Pro Leu Thr Pro Asp Asp Thr Leu Leu
                195                 200                 205 aat gaa att ctc gat aat aca ctc aac gac acc aag atg cct aca aca      793
Asn Glu Ile Leu Asp Asn Thr Leu Asn Asp Thr Lys Met Pro Thr Thr
            210                 215                 220 gaa aga gaa aca gaa ttc gct gtg ttg gag gag cag agg gtg gag ctc      841
Glu Arg Glu Thr Glu Phe Ala Val Leu Glu Glu Gln Arg Val Glu Leu
```

```
                    225                 230                 235
agc gtc tct ctg gta aac cag aag ttc aag gca gag ctc gct gac tcc        889
Ser Val Ser Leu Val Asn Gln Lys Phe Lys Ala Glu Leu Ala Asp Ser
    240                 245                 250 cag tcc cca tat tac cag gag cta gca gga aag tcc caa ctt cag atg        937
Gln Ser Pro Tyr Tyr Gln Glu Leu Ala Gly Lys Ser Gln Leu Gln Met
255                 260                 265                 270 caa aag ata ttt aag aaa ctt cca gga ttc aaa aaa atc cat gtg tta        985
Gln Lys Ile Phe Lys Lys Leu Pro Gly Phe Lys Lys Ile His Val Leu
                275                 280                 285 gga ttt aga cca aag aaa gaa aaa gat ggc tca agc tcc aca gag atg       1033
Gly Phe Arg Pro Lys Lys Glu Lys Asp Gly Ser Ser Ser Thr Glu Met
                    290                 295                 300 caa ctt acg gcc atc ttt aag aga cac agt gca gaa gca aaa agc cct       1081
Gln Leu Thr Ala Ile Phe Lys Arg His Ser Ala Glu Ala Lys Ser Pro
            305                 310                 315 gca agt gac ctc ctg tct ttt gat tcc aac aaa att gaa agt gag gaa       1129
Ala Ser Asp Leu Leu Ser Phe Asp Ser Asn Lys Ile Glu Ser Glu Glu
        320                 325                 330 gtc tat cat gga acc atg gag gag gac aag caa cca gaa atc tat ctc       1177
Val Tyr His Gly Thr Met Glu Glu Asp Lys Gln Pro Glu Ile Tyr Leu
335                 340                 345                 350 aca gct aca gac ctc aaa agg ctg atc agc aaa gca cta gag gaa gaa       1225
Thr Ala Thr Asp Leu Lys Arg Leu Ile Ser Lys Ala Leu Glu Glu Glu
                355                 360                 365 caa tct ttg gat gtg ggg aca att cag ttc act gat gaa att gct gga       1273
Gln Ser Leu Asp Val Gly Thr Ile Gln Phe Thr Asp Glu Ile Ala Gly
            370                 375                 380 tca ctg cca gcc ttt ggt cct gac acc caa tca gag ctg ccc aca tct       1321
Ser Leu Pro Ala Phe Gly Pro Asp Thr Gln Ser Glu Leu Pro Thr Ser
        385                 390                 395 ttt gct gtt ata aca gag gat gct act ttg agt cca gaa ctt cct cct       1369
Phe Ala Val Ile Thr Glu Asp Ala Thr Leu Ser Pro Glu Leu Pro Pro
400                 405                 410 gtt gaa ccc cag ctt gag aca gtg gac gga gca gag cat ggt cta cct       1417
Val Glu Pro Gln Leu Glu Thr Val Asp Gly Ala Glu His Gly Leu Pro
415                 420                 425                 430 gac act tct tgg tct cca cct gct atg gcc tct acc tcc ctg tca gaa       1465
Asp Thr Ser Trp Ser Pro Pro Ala Met Ala Ser Thr Ser Leu Ser Glu
                435                 440                 445 gct cca cct ttc ttt atg gca tca agc atc ttc tct ctg act gat caa       1513
Ala Pro Pro Phe Phe Met Ala Ser Ser Ile Phe Ser Leu Thr Asp Gln
            450                 455                 460 ggc acc aca gat aca atg gcc act gac cag aca atg cta gta cca ggg       1561
Gly Thr Thr Asp Thr Met Ala Thr Asp Gln Thr Met Leu Val Pro Gly
        465                 470                 475 ctc acc atc ccc acc agt gat tat tct gca atc agc caa ctg gct ctg       1609
Leu Thr Ile Pro Thr Ser Asp Tyr Ser Ala Ile Ser Gln Leu Ala Leu
480                 485                 490 gga att tca cat cca cct gca tct tca gat gac agc cga tca agt gca       1657
Gly Ile Ser His Pro Pro Ala Ser Ser Asp Asp Ser Arg Ser Ser Ala
495                 500                 505                 510 ggt ggc gaa gat atg gtc aga cac cta gat gaa atg gat ctg tct gac       1705
Gly Gly Glu Asp Met Val Arg His Leu Asp Glu Met Asp Leu Ser Asp
                515                 520                 525 act cct gcc cca tct gag gta cca gag ctc agc gaa tat gtt tct gtc       1753
Thr Pro Ala Pro Ser Glu Val Pro Glu Leu Ser Glu Tyr Val Ser Val
            530                 535                 540 cca gat cat ttc ttg gag gat acc act cct gtc tca gct tta cag tat       1801
```

-continued

```
                Pro Asp His Phe Leu Glu Asp Thr Thr Pro Val Ser Ala Leu Gln Tyr
                        545                 550                 555 atc acc act agt tct atg acc att gcc ccc aag ggc cga gag ctg gta         1849
Ile Thr Thr Ser Ser Met Thr Ile Ala Pro Lys Gly Arg Glu Leu Val
        560                 565                 570 gtg ttc ttc agt ctg cgt gtt gct aac atg gcc ttc tcc aac gac ctg         1897
Val Phe Phe Ser Leu Arg Val Ala Asn Met Ala Phe Ser Asn Asp Leu
575                 580                 585                 590 ttc aac aag agc tct ctg gag tac cga gct ctg gag caa caa ttc aca         1945
Phe Asn Lys Ser Ser Leu Glu Tyr Arg Ala Leu Glu Gln Gln Phe Thr
                595                 600                 605 cag ctg ctg gtt cca tat cta cga tcc aat ctt aca gga ttt aag caa         1993
Gln Leu Leu Val Pro Tyr Leu Arg Ser Asn Leu Thr Gly Phe Lys Gln
        610                 615                 620 ctt gaa ata ctt aac ttc aga aac ggg agt gtg att gtg aat agc aaa         2041
Leu Glu Ile Leu Asn Phe Arg Asn Gly Ser Val Ile Val Asn Ser Lys
625                 630                 635 atg aag ttt gct aag tct gtg ccg tat aac ctc acc aag gct gtg cac         2089
Met Lys Phe Ala Lys Ser Val Pro Tyr Asn Leu Thr Lys Ala Val His
                640                 645                 650 ggg gtc ttg gag gat ttt cgt tct gct gca gcc caa caa ctc cat ctg         2137
Gly Val Leu Glu Asp Phe Arg Ser Ala Ala Ala Gln Gln Leu His Leu
655                 660                 665                 670 gaa ata gac agc tac tct ctc aac att gaa cca gct gat caa gca gat         2185
Glu Ile Asp Ser Tyr Ser Leu Asn Ile Glu Pro Ala Asp Gln Ala Asp
                675                 680                 685 ccc tgc aag ttc ctg gcc tgc ggc gaa ttt gcc caa tgt gta aag aac         2233
Pro Cys Lys Phe Leu Ala Cys Gly Glu Phe Ala Gln Cys Val Lys Asn
        690                 695                 700 gaa cgg act gag gaa gcg gag tgt cgc tgc aaa cca gga tat gac agc         2281
Glu Arg Thr Glu Glu Ala Glu Cys Arg Cys Lys Pro Gly Tyr Asp Ser
705                 710                 715 cag ggg agc ctg gac ggt ctg gaa cca ggc ctc tgt ggc ctg gca caa         2329
Gln Gly Ser Leu Asp Gly Leu Glu Pro Gly Leu Cys Gly Leu Ala Gln
        720                 725                 730 agg aat gcg agg tcc tcc agg gaa agg gag ctc cat gcg gtt cca gat         2377
Arg Asn Ala Arg Ser Ser Arg Glu Arg Glu Leu His Ala Val Pro Asp
735                 740                 745                 750 cac tct gaa aat caa gca tac aaa act agt gtt aaa agt tcc aaa atc         2425
His Ser Glu Asn Gln Ala Tyr Lys Thr Ser Val Lys Ser Ser Lys Ile
                755                 760                 765 aac aaa ata aca agg taatcagtaa agaaattct gaattactga ccgtagaata         2480
Asn Lys Ile Thr Arg
                770 tgaagaattt aaccatcaag attgggaagg aaattaaaaa ctgaaaatgt acaattatca      2540 cttaggctat ctcaagagag atgatttgcc ttctcaagga aaatggagac aggcatattc      2600 atgggtcatc aaaatccaga catacagtca acactgagaa tcagcacaca ccatatttca      2660 aatatagaag agtcatgtac ttggcaacca gtaaattctg aaaaaaaga cacttactta       2720 ttattaaaac cccaaatgca atcagcgaaa catatttta ctattcttgg atgatagtca       2780 aaatgatcat aagccaggtt tgcttccacc ttccctgaaa attttactca cagatcattt      2840 gcaacaagca tagcttactt attgtttagg gactgaacaa tttattggga agcaaactct      2900 ttatatgcta gaaagtacat ttaaaagatg actacttacg cagggagatg caggtctctc      2960 taaacgcatg aatgtatgta gtgtgtaggc actgtagtga gtgtatatat gctccacact      3020 acgtctgata aacacaaacc tcagtattca gttattaggc acactagttt tatacgcaac      3080
```

-continued

```
tactgcttac atagtagact gttttgttgc caataatctt tgaattgttc tttaaaagaa    3140
actgaggttc agatacacat accatggaaa aatcttactt ttcttgttac tacacaaagc    3200
tattttaaag aagatgctat gttgggagaa gggcgaagtt gtactatatg acataatcaa    3260
t                                                                    3261
```

<210> SEQ ID NO 28
<211> LENGTH: 771
<212> TYPE: PRT
<213> ORGANISM: Homo sapiens
<223> OTHER INFORMATION: Human IPM 150 isoform A variant cDNA sequence

<400> SEQUENCE: 28

```
Met Tyr Leu Glu Thr Arg Arg Ala Ile Phe Val Phe Trp Ile Phe Leu
 1               5                  10                  15

Gln Val Gln Gly Thr Lys Asp Ile Ser Ile Asn Ile Tyr His Ser Glu
            20                  25                  30

Thr Lys Asp Ile Asp Asn Pro Arg Asn Glu Thr Thr Glu Ser Thr
        35                  40                  45

Glu Lys Met Tyr Lys Met Ser Thr Met Arg Arg Ile Phe Asp Leu Ala
 50                  55                  60

Lys His Arg Thr Lys Arg Ser Ala Phe Phe Pro Thr Gly Val Lys Val
 65                  70                  75                  80

Cys Pro Gln Glu Ser Met Lys Gln Ile Leu Asp Ser Leu Gln Ala Tyr
                85                  90                  95

Tyr Arg Leu Arg Val Cys Gln Glu Ala Val Trp Glu Ala Tyr Arg Ile
            100                 105                 110

Phe Leu Asp Arg Ile Pro Asp Thr Gly Glu Tyr Gln Asp Trp Val Ser
        115                 120                 125

Ile Cys Gln Gln Glu Thr Phe Cys Leu Phe Asp Ile Gly Lys Asn Phe
130                 135                 140

Ser Asn Ser Gln Glu His Leu Asp Leu Leu Gln Arg Ile Lys Gln
145                 150                 155                 160

Arg Ser Phe Pro Asp Arg Lys Asp Glu Ile Ser Ala Glu Lys Thr Leu
                165                 170                 175

Gly Glu Pro Gly Glu Thr Ile Val Ile Ser Thr Asp Val Ala Asn Val
            180                 185                 190

Ser Leu Gly Pro Phe Pro Leu Thr Pro Asp Thr Leu Leu Asn Glu
        195                 200                 205

Ile Leu Asp Asn Thr Leu Asn Asp Thr Lys Met Pro Thr Thr Glu Arg
210                 215                 220

Glu Thr Glu Phe Ala Val Leu Glu Glu Gln Arg Val Glu Leu Ser Val
225                 230                 235                 240

Ser Leu Val Asn Gln Lys Phe Lys Ala Glu Leu Ala Asp Ser Gln Ser
                245                 250                 255

Pro Tyr Tyr Gln Glu Leu Ala Gly Lys Ser Gln Leu Gln Met Gln Lys
            260                 265                 270

Ile Phe Lys Lys Leu Pro Gly Phe Lys Ile His Val Leu Gly Phe
        275                 280                 285

Arg Pro Lys Lys Glu Lys Asp Gly Ser Ser Thr Glu Met Gln Leu
290                 295                 300

Thr Ala Ile Phe Lys Arg His Ser Ala Glu Ala Lys Ser Pro Ala Ser
305                 310                 315                 320

Asp Leu Leu Ser Phe Asp Ser Asn Lys Ile Glu Ser Glu Glu Val Tyr
                325                 330                 335
```

```
His Gly Thr Met Glu Glu Asp Lys Gln Pro Glu Ile Tyr Leu Thr Ala
            340                 345                 350

Thr Asp Leu Lys Arg Leu Ile Ser Lys Ala Leu Glu Glu Glu Gln Ser
            355                 360                 365

Leu Asp Val Gly Thr Ile Gln Phe Thr Asp Glu Ile Ala Gly Ser Leu
            370                 375                 380

Pro Ala Phe Gly Pro Asp Thr Gln Ser Glu Leu Pro Thr Ser Phe Ala
385                 390                 395                 400

Val Ile Thr Glu Asp Ala Thr Leu Ser Pro Glu Leu Pro Pro Val Glu
                405                 410                 415

Pro Gln Leu Glu Thr Val Asp Gly Ala Glu His Gly Leu Pro Asp Thr
            420                 425                 430

Ser Trp Ser Pro Pro Ala Met Ala Ser Thr Ser Leu Ser Glu Ala Pro
            435                 440                 445

Pro Phe Phe Met Ala Ser Ser Ile Phe Ser Leu Thr Asp Gln Gly Thr
            450                 455                 460

Thr Asp Thr Met Ala Thr Asp Gln Thr Met Leu Val Pro Gly Leu Thr
465                 470                 475                 480

Ile Pro Thr Ser Asp Tyr Ser Ala Ile Ser Gln Leu Ala Leu Gly Ile
                485                 490                 495

Ser His Pro Pro Ala Ser Ser Asp Asp Ser Arg Ser Ser Ala Gly Gly
            500                 505                 510

Glu Asp Met Val Arg His Leu Asp Glu Met Asp Leu Ser Asp Thr Pro
            515                 520                 525

Ala Pro Ser Glu Val Pro Glu Leu Ser Glu Tyr Val Ser Val Pro Asp
            530                 535                 540

His Phe Leu Glu Asp Thr Thr Pro Val Ser Ala Leu Gln Tyr Ile Thr
545                 550                 555                 560

Thr Ser Ser Met Thr Ile Ala Pro Lys Gly Arg Glu Leu Val Val Phe
                565                 570                 575

Phe Ser Leu Arg Val Ala Asn Met Ala Phe Ser Asn Asp Leu Phe Asn
            580                 585                 590

Lys Ser Ser Leu Glu Tyr Arg Ala Leu Glu Gln Gln Phe Thr Gln Leu
            595                 600                 605

Leu Val Pro Tyr Leu Arg Ser Asn Leu Thr Gly Phe Lys Gln Leu Glu
            610                 615                 620

Ile Leu Asn Phe Arg Asn Gly Ser Val Ile Val Asn Ser Lys Met Lys
625                 630                 635                 640

Phe Ala Lys Ser Val Pro Tyr Asn Leu Thr Lys Ala Val His Gly Val
                645                 650                 655

Leu Glu Asp Phe Arg Ser Ala Ala Gln Gln Leu His Leu Glu Ile
            660                 665                 670

Asp Ser Tyr Ser Leu Asn Ile Glu Pro Ala Asp Gln Ala Asp Pro Cys
            675                 680                 685

Lys Phe Leu Ala Cys Gly Glu Phe Ala Gln Cys Val Lys Asn Glu Arg
            690                 695                 700

Thr Glu Glu Ala Glu Cys Arg Cys Lys Pro Gly Tyr Asp Ser Gln Gly
705                 710                 715                 720

Ser Leu Asp Gly Leu Glu Pro Gly Leu Cys Gly Leu Ala Gln Arg Asn
            725                 730                 735

Ala Arg Ser Ser Arg Glu Arg Glu Leu His Ala Val Pro Asp His Ser
            740                 745                 750
```

```
Glu Asn Gln Ala Tyr Lys Thr Ser Val Lys Ser Ser Lys Ile Asn Lys
        755                 760                 765

Ile Thr Arg
    770

<210> SEQ ID NO 29
<211> LENGTH: 20
<212> TYPE: PRT
<213> ORGANISM: Rattus sp.
<220> FEATURE:
<223> OTHER INFORMATION: Rat IPM 200 N-terminal amino acid sequence

<400> SEQUENCE: 29

Ser Ile Leu Phe Pro Asn Gly Val Arg Ile Cys Pro Ser Asp Thr Val
  1               5                  10                  15

Ala Glu Ala Val
            20

<210> SEQ ID NO 30
<211> LENGTH: 10
<212> TYPE: PRT
<213> ORGANISM: Pig species
<220> FEATURE:
<221> NAME/KEY: UNSURE
<222> LOCATION: (1)..(10)
<223> OTHER INFORMATION: Xaa is any  amino acid.

<400> SEQUENCE: 30

Xaa Val Leu Phe Pro Asn Gly Val Lys Ile
  1               5                  10

<210> SEQ ID NO 31
<211> LENGTH: 20
<212> TYPE: PRT
<213> ORGANISM: Pig species
<220> FEATURE:
<221> NAME/KEY: MOD_RES
<222> LOCATION: (1)..(20)
<223> OTHER INFORMATION: Xaa is any amino acid

<400> SEQUENCE: 31

Xaa Val Phe Phe Pro Thr Gly Val Lys Val Xaa Pro Gln Glu Ser Met
  1               5                  10                  15

Lys Gln Ile Leu
            20

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: RGD-
      containing peptide

<400> SEQUENCE: 32

Gly Arg Gly Asp Ser Pro
  1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:
      RGD-containing peptide

<400> SEQUENCE: 33
```

```
Gly Arg Gly Asp Thr Pro
1               5

<210> SEQ ID NO 34
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Xaa is d-Arginine

<400> SEQUENCE: 34

Gly Xaa Gly Asp Ser Pro
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: RGD-
      containing peptide
<220> FEATURE:
<221> NAME/KEY: MOD_RES
<222> LOCATION: (1)
<223> OTHER INFORMATION: MeGly

<400> SEQUENCE: 35

Gly Arg Gly Asp Ser Pro
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: RGD-
      containing peptide

<400> SEQUENCE: 36

Gly Arg Gly Asp Ser Pro Ala Ser Ser Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Inhibitor
<220> FEATURE:
<221> NAME/KEY: MOD_RES
<222> LOCATION: (2)
<223> OTHER INFORMATION: Xaa is pencillamine

<400> SEQUENCE: 37

Gly Xaa Gly Arg Gly Asp Ser Pro Cys Ala
1               5                   10
```